US011759777B2

United States Patent
Sparks et al.

(10) Patent No.: US 11,759,777 B2
(45) Date of Patent: *Sep. 19, 2023

(54) CENTRIFUGE TUBE COMPRISING A FLOATING BUOY, AND METHODS FOR USING THE SAME

(71) Applicant: ARTERIOCYTE MEDICAL SYSTEMS, INC., St. Louis, MO (US)

(72) Inventors: Rodney Sparks, Sacramento, CA (US); John Raymond Chapman, Sacramento, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/678,633

(22) Filed: Feb. 23, 2022

(65) Prior Publication Data

US 2022/0241776 A1 Aug. 4, 2022

Related U.S. Application Data

(62) Division of application No. 15/508,038, filed as application No. PCT/US2015/057599 on Oct. 27, 2015, now Pat. No. 11,278,884.

(Continued)

(51) Int. Cl.
*B01L 3/00* (2006.01)
*A61M 1/02* (2006.01)
(Continued)

(52) U.S. Cl.
CPC ......... *B01L 3/50215* (2013.01); *A61M 1/029* (2013.01); *B04B 5/0414* (2013.01);
(Continued)

(58) Field of Classification Search
CPC ......... B01L 3/50215; B01L 2200/0647; B01L 2200/0684; B01L 2300/042;
(Continued)

(56) References Cited

U.S. PATENT DOCUMENTS 60,036 A * 11/1866 Moore ............... B05B 1/18
239/437
4,057,148 A * 11/1977 Meyer ............... B01L 9/06
211/74

(Continued)

FOREIGN PATENT DOCUMENTS

DE 19543088 C1 3/1997
EP 1005910 A2 6/2000
(Continued)

OTHER PUBLICATIONS

Vernay http://www.vernay.com/Markets/Medical/Product-Categories/Umbrella-Check-Valves.aspx (Year: 2012).*

(Continued)

*Primary Examiner* — Liam Royce

(74) *Attorney, Agent, or Firm* — Polsinelli PC; Tara A. Nealey

(57) ABSTRACT

Multi-component separation devices configured to separate components of a liquid sample by centrifugation are provided. Aspects of the separation devices include a container having a distal end and a proximal end and a buoy configured to be displaced along a longitudinal axis within the container where the buoy includes one or more sealed chambers. Also provided are methods of using the subject devices to separate components of a multi-component liquid sample such as whole blood, bone marrow aspirate or stromal vascular fraction as well as systems suitable for practicing the subject methods.

24 Claims, 19 Drawing Sheets

Related U.S. Application Data

(60) Provisional application No. 62/069,783, filed on Oct. 28, 2014.

(51) Int. Cl.

| | |
|---|---|
| *B04B 5/04* | (2006.01) |
| *B04B 7/12* | (2006.01) |
| *G01N 1/38* | (2006.01) |
| *G01N 1/40* | (2006.01) |
| *G01N 33/49* | (2006.01) |
| *A61M 1/36* | (2006.01) |

(52) U.S. Cl.
CPC ............... *B04B 7/12* (2013.01); *G01N 1/38* (2013.01); *G01N 1/4077* (2013.01); *G01N 33/491* (2013.01); *A61M 1/3693* (2013.01); *B01L 2200/0647* (2013.01); *B01L 2200/0684* (2013.01); *B01L 2300/042* (2013.01); *B01L 2300/048* (2013.01); *B01L 2400/0409* (2013.01); *B01L 2400/0616* (2013.01); *G01N 2001/386* (2013.01); *G01N 2001/4083* (2013.01)

(58) Field of Classification Search
CPC ....... B01L 2300/048; B01L 2400/0409; B01L 2400/0616; A61M 1/029; A61M 1/3693; B04B 5/0414; B04B 7/12; G01N 1/38; G01N 1/4077; G01N 33/491; G01N 2001/386; G01N 2001/4083
See application file for complete search history.

(56) References Cited

U.S. PATENT DOCUMENTS

| | | | |
|---|---|---|---|
| 4,189,385 A | | 2/1980 | Greenspan |
| 4,332,351 A | | 6/1982 | Kellogg et al. |
| 4,464,254 A | | 8/1984 | Dojki et al. |
| 4,675,117 A | * | 6/1987 | Neumann ........... A61M 1/3696 210/194 |
| 4,824,560 A | | 4/1989 | Alspector |
| 4,946,601 A | | 8/1990 | Fiehler |
| 5,318,748 A | | 6/1994 | Babson et al. |
| 5,393,674 A | | 2/1995 | Levine et al. |
| 5,538,493 A | | 7/1996 | Gerken et al. |
| 5,840,502 A | | 11/1998 | Van Vlasselaer |
| 5,895,346 A | | 4/1999 | Wells et al. |
| 6,162,400 A | | 12/2000 | Schembri |
| 6,251,291 B1 | | 6/2001 | Lamphere et al. |
| 6,398,972 B1 | | 6/2002 | Blasetti et al. |
| 6,537,503 B1 | | 3/2003 | Conway |
| 6,544,162 B1 | | 4/2003 | Van Wei et al. |
| 7,060,018 B2 | | 6/2006 | Skinkle et al. |
| 7,077,273 B2 | | 7/2006 | Ellsworth et al. |
| 7,188,734 B2 | | 3/2007 | Konrad |
| 7,220,593 B2 | | 5/2007 | Haubert et al. |
| 7,329,534 B2 | | 2/2008 | Haubert et al. |
| 7,374,678 B2 | | 5/2008 | Leach et al. |
| 7,470,371 B2 | | 12/2008 | Dorian et al. |
| 7,547,272 B2 | | 6/2009 | Ellsworth et al. |
| 7,837,884 B2 | | 11/2010 | Dorian et al. |
| 7,919,049 B2 | | 4/2011 | Haubert et al. |
| 7,976,796 B1 | | 7/2011 | Smith et al. |
| 7,992,725 B2 | | 8/2011 | Leach et al. |
| 8,187,477 B2 | | 5/2012 | Dorian et al. |
| 8,361,417 B2 | | 1/2013 | Hatamian et al. |
| 8,632,736 B2 | | 1/2014 | Spatafore et al. |
| 9,011,800 B2 | * | 4/2015 | Leach ................ B01D 21/262 422/506 |
| 9,095,798 B2 | | 8/2015 | Chapman et al. |
| 9,101,925 B2 | | 8/2015 | Chapman et al. |
| 9,101,926 B2 | | 8/2015 | Chapman et al. |
| 11,278,884 B2 | * | 3/2022 | Sparks ............... B01L 3/50215 |
| 2002/0042335 A1 | * | 4/2002 | Anderson ........... B01L 3/50215 494/37 |
| 2003/0159999 A1 | * | 8/2003 | Oakey ............... B01L 3/502753 210/243 |
| 2005/0123456 A1 | | 6/2005 | Eichacker |
| 2005/0247715 A1 | | 11/2005 | Ellsworth et al. |
| 2006/0175242 A1 | | 8/2006 | Dorian et al. |
| 2008/0164204 A1 | | 7/2008 | Hatamian et al. |
| 2008/0171645 A1 | | 7/2008 | Borgstrom et al. |
| 2009/0215998 A1 | * | 8/2009 | Antman ............. B01L 3/50853 422/400 |
| 2010/0140182 A1 | * | 6/2010 | Chapman ............ B01D 21/307 210/741 |
| 2010/0163493 A1 | | 7/2010 | Hein et al. |
| 2011/0014705 A1 | * | 1/2011 | Leach ................. B01D 21/307 435/379 |
| 2011/0021332 A1 | | 1/2011 | Akatsu et al. |
| 2011/0143905 A1 | | 6/2011 | Kolenbrander et al. |
| 2012/0153207 A1 | | 6/2012 | Hatamian et al. |
| 2013/0017130 A1 | | 1/2013 | Haubert |
| 2013/0072903 A1 | | 3/2013 | Chapman |
| 2013/0327688 A1 | | 12/2013 | Chapman et al. |

FOREIGN PATENT DOCUMENTS

| | | |
|---|---|---|
| EP | 1509326 B1 | 6/2007 |
| EP | 1289618 B1 | 1/2008 |
| JP | S4964864 U | 6/1974 |
| JP | H0947649 A | 2/1997 |
| JP | H09103707 A | 4/1997 |
| JP | 2005279507 A | 10/2005 |
| JP | 2010527912 A | 8/2010 |
| RU | 2164172 C1 | 3/2001 |
| RU | 2179893 C2 | 2/2002 |
| SU | 644545 A1 | 1/1979 |
| SU | 948459 A2 | 8/1982 |
| WO | 1993024213 A1 | 12/1993 |
| WO | 2010065018 A1 | 6/2010 |
| WO | 2011008836 A1 | 1/2011 |
| WO | 2012026970 A2 | 3/2012 |
| WO | 2012037942 A1 | 3/2012 |

OTHER PUBLICATIONS

Office Action from related Japanese Application No. 2017523447, dated Jun. 11, 2019; 4 pgs.

Vernay Medical, https://www.vernay.com/Markets/Medical/Product-Categories/Umbrella-Check-Valves.aspx, 2012.

* cited by examiner

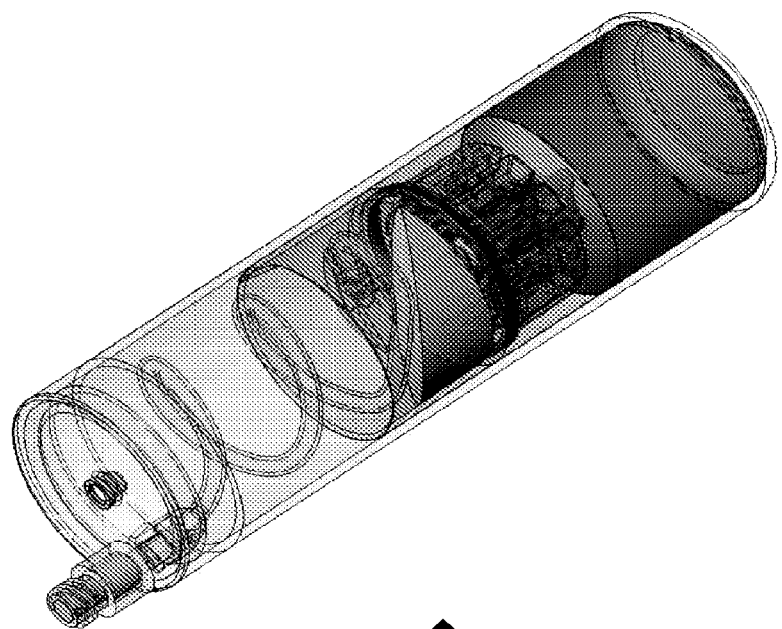
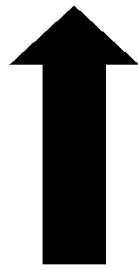
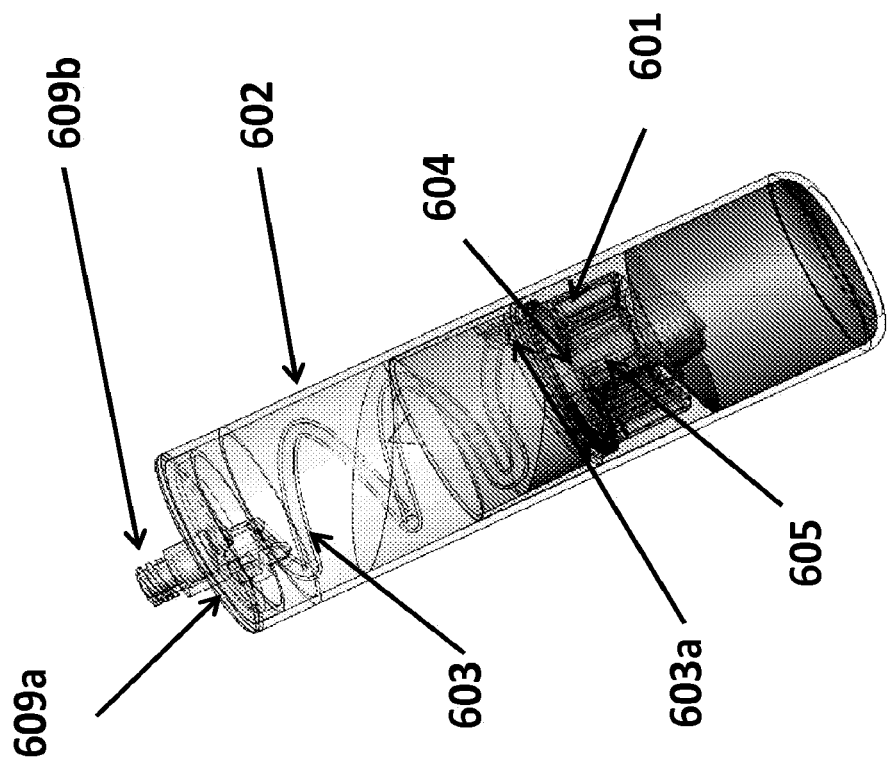
FIG. 6A
FIG. 6B

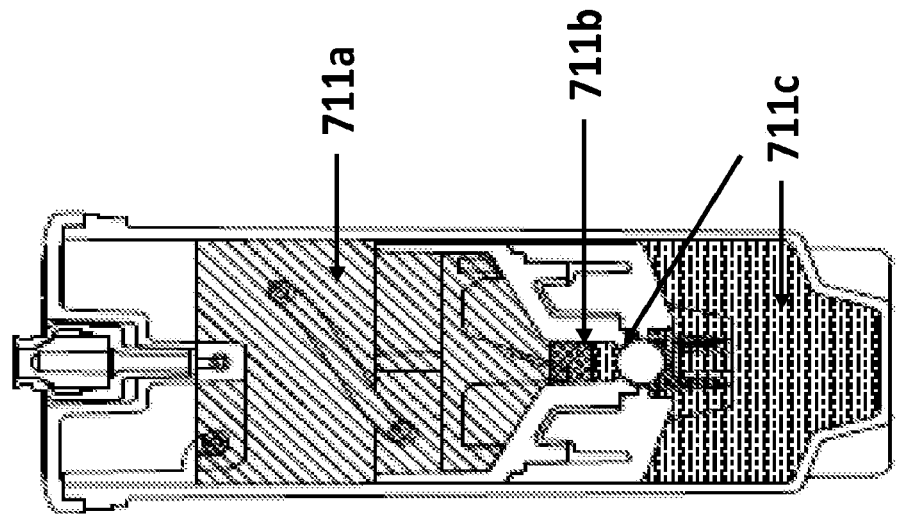
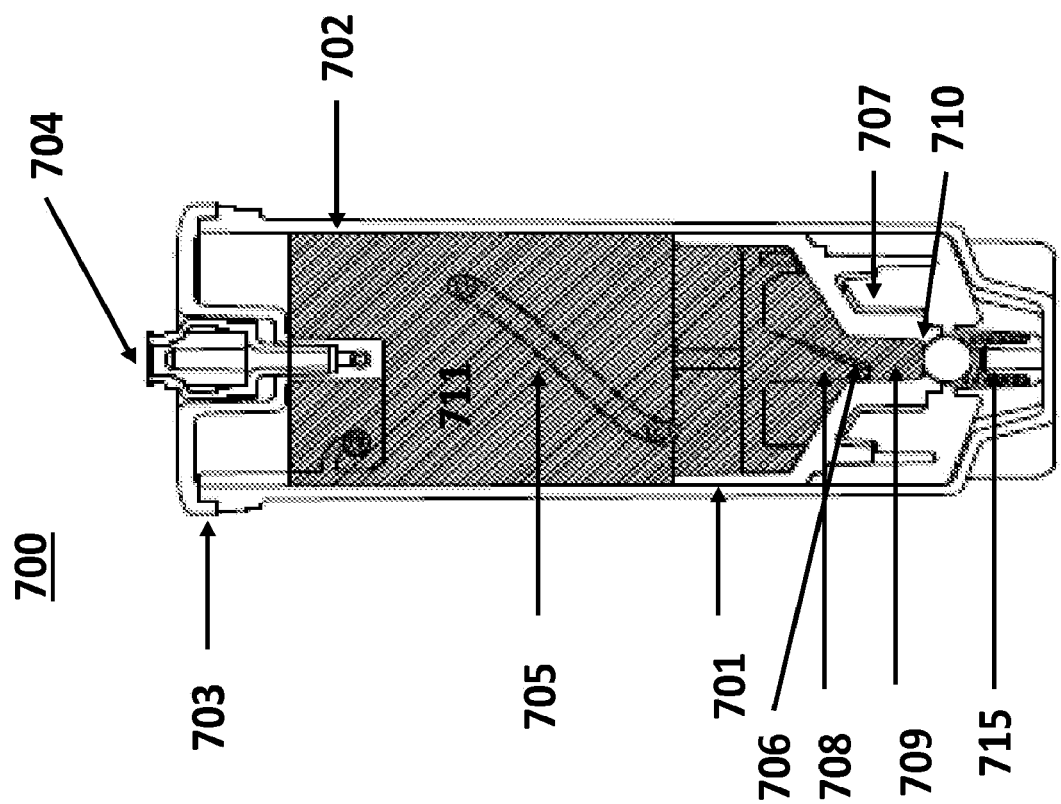
FIG. 7B
FIG. 7A

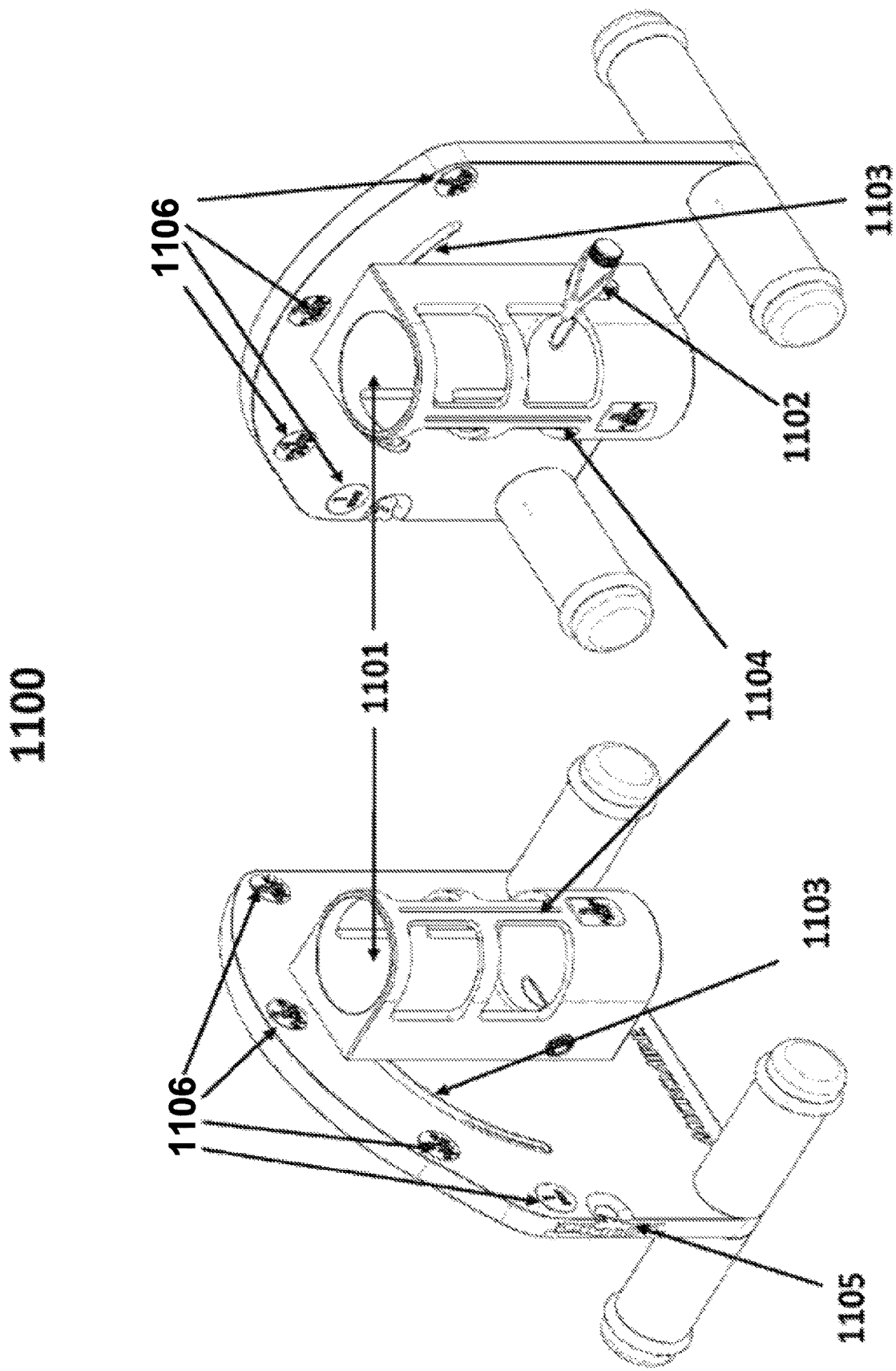

CENTRIFUGE TUBE COMPRISING A FLOATING BUOY, AND METHODS FOR USING THE SAME

CROSS-REFERENCE TO RELATED APPLICATIONS

This application is a divisional application of U.S. application Ser. No. 15/508,038, filed Mar. 1, 2017, which is a National Stage Entry of PCT Application No. PCT/US2015/057599, filed Oct. 27, 2015, which claims priority from U.S. Provisional Patent Application No. 62/069,783, filed Oct. 28, 2014, the disclosures of which are herein incorporated by reference.

INTRODUCTION

Centrifugation has been used in the separation of components in a suspended medium to obtain cells, organelles or macromolecules contained in multi-component biologic fluids including bone marrow, whole blood, peripheral blood, urine, phlegm, synovial semen, milk, saliva, mucus, sputum, exudates, cerebrospinal fluid, amniotic fluid, cord blood, intestinal fluid, cell suspensions, tissue digests, tumor cell containing cell suspensions, microbe containing cell suspensions, radiolabelled cell suspensions and cell culture fluid which may or may not contain additional substances (e.g., anticoagulants to prevent clotting). Centrifugation of a medium having suspended particles causes the particles to sediment in the direction outward from the axis of rotation. The force generated by centrifugation is proportional to the speed of rotation and the radius of the rotor. At a fixed force and medium viscosity, the sedimentation rate of the particle is proportional to the molecular weight of the particle and the difference between its density and the density of the medium.

Components from biological fluids are used in a variety of therapeutic, diagnostic and research applications. Many biological fluid chemistry tests require separation of the components in the biological fluid. For example, when the biological fluid is blood, white blood cells, red blood cells, platelets and plasma components are often separated for testing. Enriched preparation of biological samples having sufficient concentration of components for the desired therapeutic, diagnostic or research use, can often require numerous and lengthy manipulations which often degrades the recovered materials or diminish the amount of recoverable biological sample components. For example, multiple iterations of separation and washing of biological samples can be deleterious to components such as white blood cells, red blood cells and platelets due to over-processing.

SUMMARY

Multi-component separation devices configured to separate components of a liquid sample by centrifugation are provided. Aspects of the separation devices may include a container having a distal end and a proximal end and a buoy configured to be displaced along a longitudinal axis within the container where the buoy includes one or more sealed chambers containing a vacuum or a fluidic, e.g., gaseous or liquid, composition. Also provided are methods of using the subject devices to separate components of a multi-component liquid sample, as well as systems suitable for practicing the subject methods.

Aspects of the disclosure include devices for separating components of a multi-component liquid sample by centrifugation. Devices for separating a multi-component liquid sample (e.g., whole blood or bone marrow aspirate) according to certain embodiments include a container having a distal end and a proximal end and a buoy configured to be displaced along a longitudinal axis within the container, where the buoy includes one or more sealed chambers containing a vacuum or a fluidic, e.g., gaseous or liquid, composition. The buoy, in some embodiments, includes a distal frustoconical shaped component and a proximal end having an outer surface, which surface may be a concave or convex outer surface. In certain instances, the buoy includes an orifice at the base of the outer surface at the buoy proximal end and a centrifuge activated suspension floor (e.g., in the form of a check valve) having an open position and a closed position such that the suspension floor is configured to fluidically seal the orifice at the base of the outer surface when in the closed position. In other instances, the buoy includes a first orifice at the base of the outer surface of the buoy proximal end, a second orifice at a position distal to the first orifice along the longitudinal axis of the buoy, a channel that extends from the first orifice to the second orifice and a centrifuge activated valve (i.e., check valve) having an open position and a closed position such that the valve is configured to fluidically seal the second orifice when in the closed position. Where the buoy includes a centrifuge activated valve, in some instances, the valve is a ball and spring valve, such as a stainless steel ball and spring valve. In certain embodiments, the container includes a cap positioned at the proximal end of the container having one or more ports into the interior cavity of the container. In some embodiments, the cap positioned at the proximal end of the container consists of a single port. In some instances, the separation device also includes a conduit that extends from the port to the proximal end of the buoy, such as at a position along the outer edge of the buoy proximal end (i.e., adjacent to the inner walls of the container). The conduit may be releasably attached to or fully integrated with one or more of the port and the buoy. In certain embodiments, the conduit is coupled to a stream modulator at the buoy proximal end. The stream modulator may also be attached to the buoy. Predetermined volume measurement markings may also, in certain instances, be present on the outer walls of the container.

Aspects of the disclosure also include methods for separating components of a multi-component liquid sample. Methods according to certain embodiments include introducing a multi-component liquid sample (e.g., blood) into a container of a separation device having a buoy configured to be displaced along a longitudinal axis within the container where the buoy includes one or more sealed chambers containing a fluidic, e.g., gaseous or liquid, composition, subjecting the sample to a force of centrifugation to produce two or more fractions in the sample, each fraction having a component from the sample of a different density and collecting one or more components of the sample. Where the container includes a cap at the proximal end having only a single port, the sample is introduced into the container and one or more fractions may be collected from the container after centrifugation through the single port. For example, where the single port is coupled to a conduit, the sample may be introduced into the container through the port and conduit and one or more fractions from the multicomponent sample may be collected after centrifugation through the conduit and single port. In some embodiments, the container includes a cap at the proximal end having more than one port. In some instances, the container includes a second opening in the cap to allow air to vent during sample introduction and removal.

In certain embodiments, the sample is a biological sample (e.g., blood or bone marrow aspirate) and methods include introducing a biological sample into the container of a separation device having a buoy configured to be displaced along a longitudinal axis within the container where the buoy includes one or more sealed chambers containing a fluidic composition, subjecting the blood sample to a force of centrifugation to produce two or more fractions in the biological sample, each fraction having a biological component of a different density and collecting one or more of the separated components. In some instances, subjecting the biological sample to a force of centrifugation is sufficient to displace the buoy proximally along a longitudinal axis within the container from the bottom of the container to a position at the interface between a first fraction and a second fraction of the biological sample. In certain embodiments, collecting one or more components of the biological sample includes removing a portion of a first separated fraction of the biological sample, mixing the remaining portion of the first separated fraction with a second separated fraction within the buoy to produce a mixture of the first separated fraction and the second separated fraction and removing the mixture from the container.

In other embodiments, the present invention provides a means of collecting varying volumes of one or more components of the sample by a step comprising positioning the container of the separation device at a first angle (e.g., 20 degrees or more) with respect to an axis orthogonal to the ground, removing a portion of a first separated fraction of the sample through a conduit which extends from a port in the cap to the proximal end of the buoy, rotating the container by a second angle (e.g., 180 degrees) along the longitudinal axis of the container, aspirating the remaining portion of the first separated fraction of the sample through the conduit, mixing the remaining portion of the first separated fraction with a second separated fraction within the buoy to produce a mixture of the first separated fraction and the second separated fraction and removing the mixture from the container. In some instances, the first fraction contains platelet poor plasma and the second fraction contains white blood cells and platelet rich plasma.

In still other embodiments, the present invention provides means of collecting varying volumes of one or more components of the sample by a step that includes positioning the device at a first angle with respect to an axis orthogonal to the ground (e.g., in a tilter stand); removing a portion of a first fraction of the biological sample; tilting the device to a second angular position with respect to the axis orthogonal to the ground; aspirating the remaining portion of the first fraction of the biological sample; mixing the remaining portion of the first fraction with a second fraction within the buoy to produce a mixture of the first fraction and the second fraction; and removing the mixture from the container. In some instances, the first fraction contains platelet poor plasma and the second fraction contains white blood cells and platelet rich plasma.

Aspects of the disclosure also include systems for practicing the subject methods. Systems according to certain embodiments include a centrifuge and one or more of the subject separation devices that include a container having a distal end and a proximal end and a buoy configured to be displaced along a longitudinal axis within the container where the buoy includes one or more sealed chambers containing a fluidic, e.g., gaseous or liquid, composition.

BRIEF DESCRIPTION OF THE FIGURES

The invention may be best understood from the following detailed description when read in conjunction with the accompanying drawings. Included in the drawings are the following figures:

FIG. 6A illustrates a step of removing in an example of methods for separating components of a multi-component liquid sample (e.g., blood or bone marrow aspirate) according to certain embodiments.

FIG. 6B illustrates a step of removing in an example of methods for separating components of a multi-component liquid sample (e.g., blood or bone marrow aspirate) according to certain embodiments.

FIG. 7A illustrates step-by-step methods for separating components of a multi-component liquid sample according to certain embodiments. A multi-component liquid sample (e.g., blood) is introduced into the container with a syringe or other suitable dispensing protocol.

FIG. 7B illustrates step-by-step methods for separating components of a multi-component liquid sample according to certain embodiments. The multi-component sample is separated into fractions.

FIG. 11A depicts an adjustable tilter stand for positioning the device at a desired angle to remove one (or a portion) or more fractions after centrifugation according to certain embodiments. A three-dimensional perspective of the tilter stand.

FIG. 11B depicts an adjustable tilter stand for positioning the device at a desired angle to remove one (or a portion) or more fractions after centrifugation according to certain embodiments. A three-dimensional perspective of the tilter stand.

DETAILED DESCRIPTION

Figure 1:
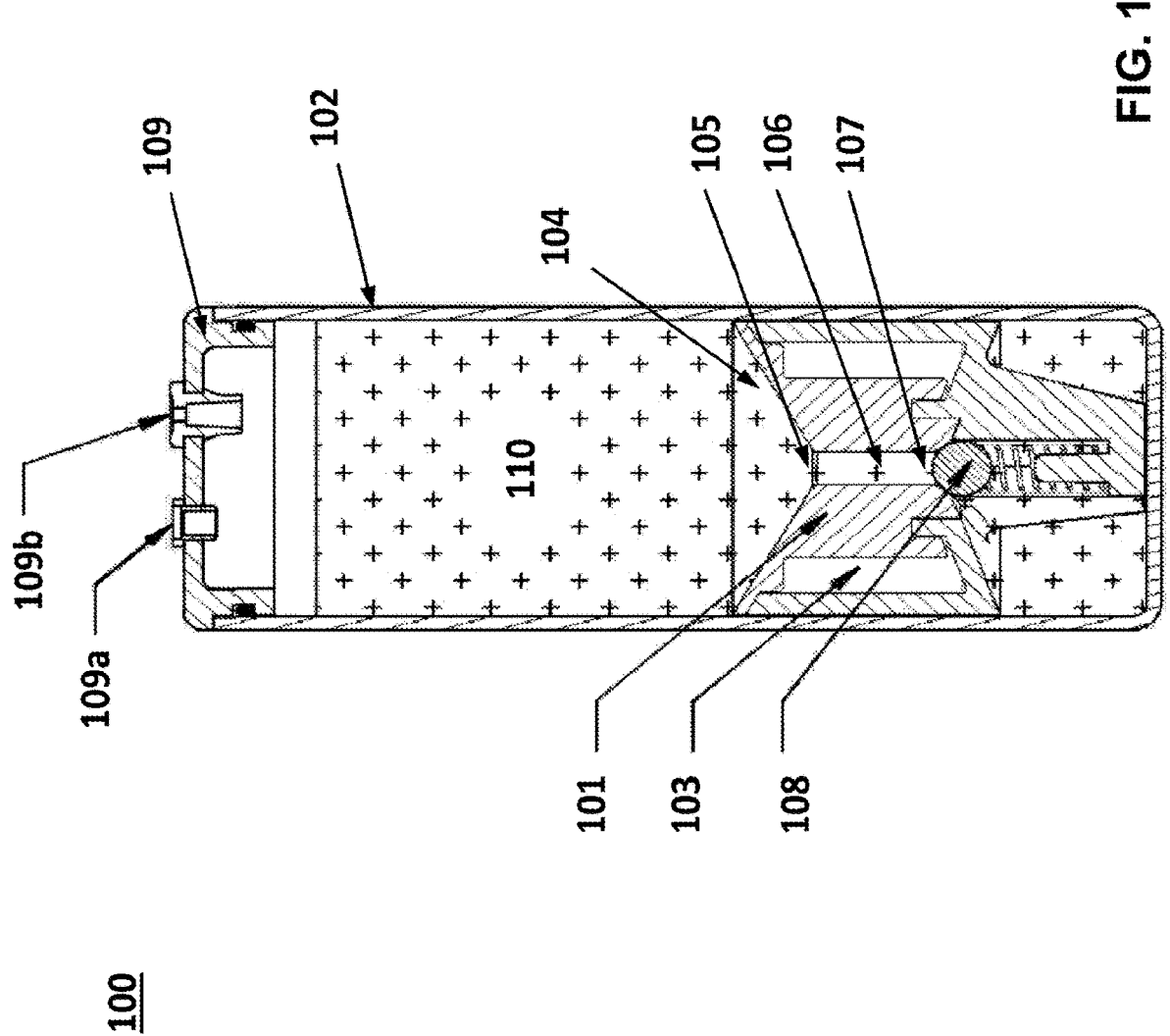
FIG. 1 depicts a side-view of a separation device having a buoy positioned inside of a container having a ball-and-spring valve according to certain embodiments.

Multi-component separation devices configured to separate components of a liquid sample by centrifugation are provided. Aspects of the separation devices may include a container having a distal end and a proximal end and a buoy configured to be displaced along a longitudinal axis within the container where the buoy includes one or more sealed chambers containing a fluidic, e.g., gaseous or liquid, composition. Also provided are methods of using the subject devices to separate components of a multi-component liquid sample, as well as systems suitable for practicing the subject methods.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the present disclosure provides a separation device for separating components of a liquid sample. In further describing embodiments of the disclosure, separation devices that include a container having a distal end and a proximal end and a buoy configured to be displaced along a longitudinal axis within the container are first described in greater detail. Next, methods for separating components of a liquid sample, such as a blood sample, with the subject separation devices are described. Systems, including a centrifuge, suitable for practicing the subject methods are also provided.

Devices for Separating Components of a Liquid Sample by Centrifugation

As summarized above, aspects of the present disclosure include devices for separating components of a multi-component liquid sample by subjecting the sample to a force of centrifugation. The term "separating" is used herein in its conventional sense to refer to the physical separation of a plurality of components based on a particular physical or chemical property, such as density of the component. As described in greater detail below, the multi-component sample is introduced into one or more of the subject separation devices and subjected to a force of centrifugation for a duration sufficient to separate one or more components of the liquid sample. In embodiments, components are separated within the sample such that each component has an increased concentration in a particular region (e.g., distal end, proximal end or middle portion of the device container) as compared to the multi-component sample before centrifugation. In certain embodiments, the multi-component liquid sample is blood or a derivative thereof and separation devices of interest are configured to separate components of the blood sample, such as separating white blood cells, red blood cells, plasma and platelets.

In embodiments, components of the liquid sample are separated into two or more regions (i.e., fractions) in the sample such that 5% or more of a certain component is separated into a particular region (e.g., distal end, proximal end or middle portion) of the device container, such as 10% or more, such as 20% or more, such as 25% or more, such as 30% or more, such as 40% or more, such as 50% or more, such as 60% or more, such as 70% or more, such as 80% or more, such as 90% or more, such as 95% or more and including separating 99% or more of a component into a particular region of the device container. In certain embodiments, 100% of the component is separated into a particular region of the device container. For example, where the multi-component liquid sample is a blood sample, separation devices of interest are configured to separate the blood sample in two or more fraction layers, such as three or more fraction layers in the device container. For example, in certain embodiments a layer of red blood cells forms at a distal end of the device container, a layer of platelet poor plasma is formed at the proximal end of the device container and a layer of buffy coat is formed on a surface of the buoy.

As used herein, the term "multi-component liquid sample" is used to describe suspended media having more than one component, where multi-component liquid samples may include, but are not limited to, biological samples. The term "biological sample" is used in its conventional sense to include a whole organism, plant, fungi or a subset of animal tissues, cells or component parts which may in certain instances be found in blood (e.g., peripheral blood), mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may include any type of organismic material, including both healthy and diseased components (e.g., cancerous, malignant, necrotic, etc.). Biological samples may include biologic fluids including bone marrow, phlegm, sputum, exudates, intestinal fluid, cell suspensions, tissue digests, tumor cell containing cell suspensions, microbe containing cell suspensions, and radiolabelled cell suspensions.

In certain embodiments, the biological sample is a liquid sample, such as whole blood or derivative thereof (e.g., plasma), tears, sweat, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.). The term "blood sample" refers to whole blood or a subset of blood components, including but not limited to platelets, red blood cells, white cells, buffy coat and blood plasma. The term "buffy coat" is used herein in its conventional sense to refer to the fractionated portion of blood of intermediate density (less dense than red blood cells, more dense than plasma) that contains white blood cells and platelets. In some embodiments, the blood sample is obtained from an in vivo source and can include blood samples obtained from tissues (e.g., bone marrow aspirate, cell suspension from a tissue biopsy, cell suspension from a tissue sample, etc.) or directly from a subject. In some cases, blood samples derived from a subject are cultured, stored, or manipulated prior to evaluation.

In certain embodiments the source of the biological sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present disclosure may be applied to samples from a human subject, it is to be understood that the methods may also be carried-out on samples from other animal subjects (that is, in "non-human subjects") such as, but not limited to, birds, mice, rats, dogs, cats, livestock and horses.

Separation devices of interest may be configured to separate components of multi-component liquid samples of varying size, depending on the size of the container and buoy (as described in greater detail below) where in some instances the volume of sample may range from 5 mL to 5000 mL, such as from 10 mL to 2500 mL, such as from 15 mL to 1000 mL, such as from 25 mL to 750 mL, such as from 30 mL to 500 mL, such as from 40 mL to 250 mL, and including from 50 mL to 100 mL. In one example, separation devices of interest are configured to separate components of a 30 mL sample. In another example, separation devices of interest are configured to separate components of a 60 mL sample. In yet another example, separation devices of interest are configured to separate components of a 100 mL sample.

In certain embodiments, the liquid sample is a specimen (e.g., blood or bone marrow aspirate) that has been preloaded into the separation device container and is stored in the container for a predetermined period of time before subjecting the sample to centrifugation. For example, a sample may be preloaded into one or more of the subject separation devices and stored at reduced temperature (e.g., refrigerator or freezer). The amount of storage time before subjecting the sample to a force of centrifugation may vary, such as 0.1 hours or more, such as 0.5 hours or more, such as 1 hour or more, such as 2 hours or more, such as 4 hours or more, such as 8 hours or more, such as 16 hours or more, such as 24 hours or more, such as 48 hours or more, such as 72 hours or more, such as 96 hours or more, such as 120 hours or more, such as 144 hours or more, such as 168 hours or more and including preloading the sample into one or more of the subject separation devices 240 hours or more before subjecting the sample to a force of centrifugation or may range such as from 0.1 hours to 240 hours before subjecting the sample to a force of centrifugation, such as from 0.5 hours to 216 hours, such as from 1 hour to 192 hours and including from 5 hours to 168 hours.

In some embodiments, the sample may be preloaded into one or more of the subject separation devices at a remote location (e.g., at home using an at-home kit or in a physician's office) and sent to a laboratory for processing in accordance with the subject methods. By "remote location" is meant a location other than the location at which the sample is obtained and preloaded into the container. For example, a remote location could be another location (e.g., office, lab, etc.) in the same city, another location in a different city, another location in a different state, another location in a different country, etc., relative to the location of the separation device, e.g., as described in greater detail below. In some instances, two locations are remote from one another if they are separated from each other by a distance of 10 m or more, such as 50 m or more, including 100 m or more, e.g., 500 m or more, 1000 m or more, 10,000 m or more, etc.

As summarized above, the subject devices include a buoy having one or more sealed chambers, such as sealed chambers containing a vacuum or a fluidic, e.g., gaseous or liquid, composition. The term "buoy" is used herein in its conventional sense to refer to an internal movable component or assembly of components of specific aggregate density that are configured to be displaced along a longitudinal axis within the container during centrifugation. The term "displace" refers to movement of the buoy through the sample in the container during centrifugation. In some embodiments, the buoy is configured to be displaced through the sample in response to the force of centrifugation. In embodiments, the subject buoy is configured to be displaced along the longitudinal axis within the container and can be displaced along all or part of the length of the inner cavity of the container, such as 25% or more of the length of the container, such as 35% or more, such as 50% or more, such as 60% or more, such as 75% or more, such as 90% or more, such as 95% or more, such as 97% or more and including 99% or more of the length of the container. In certain embodiments, the buoy can be displaced along the entire (i.e., 100%) length of the container.

In some embodiments, the buoy has a density which is greater than the multi-component liquid sample (e.g., whole blood or bone marrow aspirate) and prior to subjecting the sample to a force of centrifugation (as described in greater detail below), the buoy is positioned at the distal end of the tube (i.e., at the bottom when the tube is positioned vertically on a surface parallel to the axis of the ground). During centrifugation, the buoy is configured to be displaced proximally along the longitudinal axis of the container and takes a final position, depending on the type of multicomponent liquid composition (as described in greater detail below) that is on top of, below, or within the sample after centrifugation is complete. In some instances, the buoy is configured to take a final position at the interface between a first separated fraction and a second separated fraction of the sample. In other instances, the buoy is configured to take a final position within a fraction of the sample. In yet other instances, the buoy is configured to take a final position that is on top of the fractionated sample. In still other instances, the buoy is configured to take a final position that is below the fractionated sample (e.g., at the bottom of the container). For example, where the liquid sample is whole blood, the buoy may be configured to take a final position at an interface between the fraction containing red blood cells and the fraction containing plasma. In other instances, the buoy is configured to take a final position within the fraction containing red blood cells. In other instances, the buoy is configured to take a final position wherein the platelets, lymphocytes, monocytes and stem cells can be extracted without extracting a substantial percentage of the granulocytes and red blood cells.

In embodiments, the buoy includes one or more sealed chambers. The term "sealed" is used herein in this conventional sense to mean that the chambers are closed from fluidic, e.g., gaseous and liquid, communication with the outside environment of the buoy. Depending on the overall density of buoy desired, buoys of interest may include one or more sealed chambers, such as 2 or more, such as 3 or more, such as 4 or more, such as 5 or more, such as 10 or more and including 25 or more sealed chambers containing a fluidic composition. Where the subject buoys include more than one sealed chamber, the chambers may have the same size, different size, same shape, different sample or any combination thereof. Each sealed chamber may have a volume which varies, ranging from 0.01 $cm^3$ to 10 $cm^3$, such as from 0.05 $cm^3$ to 9.5 $cm^3$, such as from 0.1 $cm^3$ to 9 $cm^3$, such as from 0.5 $cm^3$ to 8.5 $cm^3$, such as from 1 $cm^3$ to 8 $cm^3$, such as from 1.5 $cm^3$ to 7.5 $cm^3$, such as from 2 $cm^3$ to 7 cm$^3$, and including from 2.5 cm$^3$ to 5 cm$^3$. Depending on the number of sealed chambers present in the subject buoys, the cumulative volume occupied by the sealed chambers may range from 0.01 cm$^3$ to 100 cm$^3$, such as from 0.05 cm$^3$ to 75 cm$^3$, such as from 0.1 cm$^3$ to 50 cm$^3$, such as from 0.5 cm$^3$ to 25 cm$^3$, and including from 1 cm$^3$ to 10 cm$^3$. In embodiments, the one or more sealed chambers occupies 25% or more of the total volume of the buoy, such as 30% or more, such as 35% or more, such as 40% or more, such as 45% or more, such as 50% or more, such as 60% or more, such as 70% or more and including 75% or more of the total volume of the buoy.

In some embodiments of the present disclosure, the sealed chamber(s) in the subject buoys contain a fluidic composition, e.g., a gaseous composition, a liquid composition or a combination thereof. In other embodiments, the sealed chamber(s) has a vacuum within one or more of the sealed chambers.

In some embodiments, the subject buoys include one or more sealed chambers having a gaseous composition. In other embodiments, the subject buoys include one or more sealed chambers having a liquid composition. In other embodiments, the subject buoys include one or more sealed chambers that contain a vacuum. In yet other embodiments, the subject buoys include one or more sealed chambers having a gaseous composition and one or more sealed chambers having a liquid composition. In still other embodiments, the subject buoys include one or more sealed chambers having a gaseous composition, and one or more sealed chambers that contain a vacuum. In still other embodiments, the subject buoys include one or more sealed chambers having a liquid composition and one or more sealed chambers that contain a vacuum. In still other embodiments, the subject buoys include one or more sealed chambers having a gaseous composition, one or more sealed chambers having a liquid composition and one or more sealed chambers that contain a vacuum.

Examples of gases that may be present in the gaseous compositions include, but are not limited to air, carbon dioxide, oxygen, nitrogen, hydrogen, helium, argon, xenon or a combination thereof. In certain embodiments, the sealed chambers contain air. Where the subject buoys include more than one sealed chamber, each chamber may contain the same or a different gaseous composition. For example, each sealed chamber may contain 1 or more types of gases, such as 2 or more types of gases, such as 3 or more types of gases and including 5 or more types of gases. The amount of gas present in the sealed chambers may vary depending on the type of the gas present and the desired density of the buoy. In some embodiments, the sealed chamber may include 0.001 mmoles or more of the gaseous composition, such as 0.005 mmoles or more, such as 0.01 mmoles or more, such as 0.05 mmoles or more, such as 0.1 mmoles or more, such as 0.5 mmoles or more and including 0.75 mmoles or more of the gaseous composition. The gaseous composition in the sealed chamber may be under positive or negative pressure, as desired, with respect to atmospheric pressure. In some instances, the pressure of the gaseous composition in the sealed chamber is less than atmospheric pressure, such as a pressure of 750 torr or less, such as 500 torr or less, such as 400 torr or less, such as 300 torr or less, such as 200 torr or less, such as 100 torr or less, such as 50 torr or less, such as 10 torr or less, such as 1 torr or less, such as 0.1 torr or less, such as 0.01 torr or less and including where the gaseous composition in the sealed chamber is present at a pressure of 0.001 torr or less. In other instances, the pressure of the gaseous composition in the sealed chamber is greater than atmospheric pressure, such as a pressure of 775 torr or more, such as 1000 torr or more, such as 1500 torr or more, such as 2000 torr or more, such as 2500 torr or more, such as 3000 torr or more, such as 3500 torr or more and including where the gaseous composition in the sealed chamber is present at a pressure of 5000 torr or more. In certain instances, the gaseous composition is present in the sealed chamber at atmospheric pressure (i.e., 760 torr).

In other embodiments, the sealed chamber(s) in the subject buoys contain a liquid composition. Depending on the desired density of the buoy, liquid compositions present in the sealed chamber may vary and may include both aqueous and non-aqueous liquid compositions. Accordingly, the density of the liquid composition may be varied as desired (such as by mixing two or more liquid compositions) and may range from 0.5 g/mL to 2 g/mL, such as from 0.6 g/mL to 1.9 g/mL, such as from 0.7 g/mL to 1.8 g/mL, such as from 0.8 g/mL to 1.7 g/mL, such as from 0.9 g/mL to 1.6 g/mL and including from 1 g/mL to 1.5 g/mL. In some instances, the liquid composition is an aqueous composition, such as aqueous buffers, including but not limited to phosphate buffers (e.g., PBS), tris-buffers, citrate buffers (e.g., sodium citrate), acetate buffers (e.g., sodium acetate) borate buffers (e.g., borax) as well as other types of salt buffers such as aqueous buffers containing one or more of sodium citrate, sodium acetate, sodium phosphate, sodium tartrate, sodium succinate, sodium maleate, magnesium acetate, magnesium citrate, magnesium phosphate, ammonium acetate, ammonium citrate, ammonium phosphate, and combinations thereof. In other instances, the liquid composition is a non-aqueous composition, such as an alcohol, including but not limited to methanol, ethanol, propanol, isopropanol, butanol, isobutanol, pentanol, isopentanol, hexanol, heptanol, octanol, nonanol, decanol, undecanol, isoamyl alcohol, benzyl alcohol, cetyl alcohol. Other suitable non-aqueous compositions may include but are not limited to organic solvents, such as ether, tetrahydrofuran, acetonitrile, dimethyl sulfoxide, ethyl acetate, methylene chloride, chloroform, liquid aliphatic alkanes such as pentane, cyclopentane, hexanes, heptane, iso-octane, xylenes, benzene, toluene, petroleum ether, methyl isobutyl ketone, methyl ethyl ketone, pyridine, dioxane, and dimethylformamide, among other organic solvents. In certain instances, the sealed chamber includes a polyhydric alcohol, including but not limited to glycerol, propylene glycol, neopentyl glycol, diethylene glycol, pentaerythritol, dipentaerythritol, ethylene glycol, trimethylolpropane, trimethylol ethane, di-trimethylol propane, 1,6-hexane diol and combinations thereof. Where the subject buoys include more than one sealed chamber, each chamber may contain the same or different liquid compositions. For example, each sealed chamber may contain 1 or more types of liquid composition, such as 2 or more types of liquid compositions, such as 3 or more types of liquid compositions and including 5 or more types of liquid compositions.

The shape of the sealed chamber(s) may vary, where cross-sectional shapes of interest include, but are not limited to rectilinear cross-sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In some embodiments, the sealed chambers are cylindrically shaped. In other embodiments, the sealed chambers are spherical. In yet other embodiments, the sealed chambers are square-shaped. In still other embodiments, the sealed chambers are rectangular.

The sealed chamber(s) may be at any convenient position within the buoy. In some embodiments, the sealed chambers are positioned within the buoy in a random pattern. In other embodiments, the sealed chambers are positioned in a non-random pattern (i.e., in a predetermined pattern), including in a line pattern or in a pattern of a specific shape (e.g., taking the same shape as the buoy, as a circle, triangle, etc.). In one example, the sealed chambers are arranged along the perimeter within the buoy. In another example, a buoy may include 2 sealed chambers positioned on opposite sides of the buoy. In another example, the buoy includes 4 sealed chambers positioned in a square pattern.

As described above, buoys of interest are configured to be displaced along a longitudinal axis within the container. Buoys may be any suitable shape so long as they are capable of being displaced along the longitudinal axis within the container. In some embodiments, the buoy is frustoconical-shaped. In other embodiments, the buoy includes a cylindrical-shaped proximal portion and a frustoconical-shaped distal portion. In embodiments, the distal end may have a planar, convex or concave outer surface. In some instances, the distal end has a convex outer surface. For example, the buoy may have a frustoconical-shaped or cylindrical shaped distal end having a convex outer surface. In other instances, the distal end has a concave outer surface. For example, the buoy may have a frustoconical-shaped or cylindrical shaped distal end having a concave outer surface.

The outer surface of the proximal end of the buoy may vary, as desired. As such, the proximal end may be planar, concave or convex. In certain embodiments, the buoy includes a proximal end that has a concave outer surface. In these embodiments, the concave outer surface may be configured to collect one or more components of the sample and may have a volume which ranges from 0.5 $cm^3$ to 100 $cm^3$, such as from 1 $cm^3$ to 75 $cm^3$, such as from 2 $cm^3$ to 50 $cm^3$, such as from 3 $cm^3$ to 25 $cm^3$, and including from 5 $cm^3$ to 10 $cm^3$. In certain embodiments, the buoy includes a proximal end that has a convex outer surface.

In embodiments, the buoy has an orifice at the base of the outer surface. In certain instances, the outer surface at the proximal end of the buoy terminates in a flat surface that includes one or more orifices. For example the base of the concave outer surface at the buoy proximal end may include 2 or more orifices, such as 3 or more, such as 4 or more, such as 5 or more and including 10 or more orifices. In other instances, the outer surface at the buoy proximal end terminates at an orifice. The orifice may have any suitable cross-sectional shape where examples of cross-sectional shapes include, but are not limited to rectilinear cross-sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion, etc. Depending on the size of the buoy, amount of liquid sample and specific components being separated, the size of each orifice may vary, for example ranging from 1 mm to 50 mm, such as from 2 mm to 40 mm, such as from 3 mm to 30 mm and including from 5 mm to 25 mm.

In some embodiments, the buoy also includes a centrifuge activated valve (which may also be referred to as a check valve) having an open position and a closed position such that the valve is configured to fluidically seal the orifice when in the closed position. By "fluidically seal" is meant that when the valve is in the closed position, components of the liquid sample, including fluidic components are substantially incapable of passing through the orifice. In other words, little to no amount of the liquid sample passes through the orifice when the centrifuge activated valve is in the closed position. For example, 10% or less of the liquid sample passes through the orifice when the centrifuge activated valve is in the closed position, such as 5% or less, such as 3% or less, such as 2% or less, such as 1% or less, such as 0.5% or less and including 0.1% or less of the liquid sample passes through the orifice when the centrifuge activated valve is in the closed position.

The term "centrifuge activated" is used herein in its conventional sense to refer to opening of the valve (i.e., release the fluidic seal at the orifice) in response to a force of centrifugation. As described in greater detail below, the term "force of centrifugation" refers to the force applied to the sample through revolving the subject devices about an axis of rotation where the force on the components of the sample is in certain embodiments, given by the relative centrifugal force (RCF). As such, the buoy includes a valve that fluidically seals the orifice when in the closed position and is opened in response to the applied force of centrifugation. In embodiments, the centrifuge activated valve may be configured to open in response to a force of centrifugation that varies, and may range from 1 g to 50,000 g, such as from 2 g to 45,000 g, such as from 3 g to 40,000 g, such as from 5 g to 35,000 g, such as from 10 g to 25,000 g, such as from 100 g to 20,000 g, such as from 500 g to 15,000 g, and including from 1000 g to 10,000 g.

Any convenient centrifuge activated valve protocol may be employed to fluidically seal the orifice in the subject buoys. In certain embodiments, the centrifuge activated valve includes a spring, such as where the valve includes a suspension floor which fluidically seals the orifice and is coupled to a spring that expands or compresses in response to the force of centrifugation. For example, the centrifuge activated valve, in certain embodiments, includes a spring that has a compression spring rate that is 0.0001 N/mm or more, such as 0.0005 N/mm or more, such as 0.001 N/mm or more, such as 0.005 N/mm or more, such as 0.01 N/mm or more, such as 0.05 N/mm or more, such as 0.1 N/mm or more, such as 0.5 N/mm or more, such as 1 N/mm or more, such as 5 N/mm or more, such as 10 N/mm or more, such as 25 N/mm or more, such as 50 N/mm or more, such as 100 N/mm or more, such as 250 N/mm or more and including 500 N/mm or more.

In certain embodiments, the centrifuge activated valve includes a centrifuge activated suspension floor. In these embodiments, the suspension floor is configured to open and close in response to the force of centrifugation. For example, the suspension floor may be coupled to a spring which compresses or expands in response to the force of centrifugation, as described above. Depending on the type of orifice in the buoys, centrifuge activated suspension floors may have any suitable mass having a cross-sectional shape to form a fluidic seal in the closed position. Examples of shapes for centrifuge-activated suspension floors of interest include, but are not limited to rectilinear cross-sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion, etc. In certain embodiments, the centrifuge activated suspension floor is a three-dimensional shape, such as a ball. Depending on the size of the orifice, the centrifuge activated suspension floor may have a width that is 1 mm or larger, such as 2 mm or larger, such as 5 mm or larger, such as 10 mm or larger, such as 25 mm or larger and including 50 mm or larger. For example, the centrifuge activated suspension floor may have a width that ranges from 1 mm to 50 mm, such as from 2 mm to 40 mm, such as from 3 mm to 30 mm and including from 5 mm to 25 mm.

The centrifuge activated suspension floor may be formed from glass, metal or plastic, such as a flexible or rigid plastic, polymeric or thermoplastic materials. For example, suitable polymeric plastics may include polycarbonates, polyvinyl chloride (PVC), polyurethanes, polyethers, polyamides, polyimides, or copolymers of these thermoplastics, such as PETG (glycol-modified polyethylene terephthalate), among other polymeric plastic materials. In certain embodiments, the container is formed from a polyester, where polyesters of interest may include, but are not limited to, housings made of poly(alkylene terephthalates) such as poly(ethylene terephthalate) (PET), bottle-grade PET (a copolymer made based on monoethylene glycol, terephthalic acid, and other comonomers such as isophthalic acid, cyclohexene dimethanol, etc.), poly(butylene terephthalate) (PBT), and poly(hexamethylene terephthalate); poly(alkylene adipates) such as poly(ethylene adipate), poly(1,4-butylene adipate), and poly(hexamethylene adipate); poly(alkylene suberates) such as poly(ethylene suberate); poly(alkylene sebacates) such as poly(ethylene sebacate); poly(c-caprolactone) and poly([3-propiolactone); poly(alkylene isophthalates) such as poly (ethylene isophthalate); poly(alkylene 2,6-naphthalene-dicarboxylates) such as poly(ethylene 2,6-naphthalene-dicarboxylate); poly(alkylene sulfonyl-4,4'-dibenzoates) such as poly(ethylene sulfonyl-4,4'-dibenzoate); poly(p-phenylene alkylene dicarboxylates) such as poly(p-phenylene ethylene dicarboxylates); poly(trans-1,4-cyclohexanediyl alkylene dicarboxylates) such as poly(trans-1,4-cyclohexanediyl ethylene dicarboxylate); poly(1,4-cyclohexane-dimethylene alkylene dicarboxylates) such as poly(1,4-cyclohexane-dimethylene ethylene dicarboxylate); poly ([2.2.2]-bicyclooctane-1,4-dimethylene alkylene dicarboxylates) such as poly([2.2.2]-bicyclooctane-1,4-dimethylene ethylene dicarboxylate); lactic acid polymers and copolymers such as (S)-polylactide, (R,S)-polylactide, poly (tetramethylglycolide), and poly(lactide-co-glycolide); and polycarbonates of bisphenol A, 3,3'-dimethylbisphenol A, 3,3',5,5'-tetrachlorobisphenol A, 3,3',5,5'-tetramethylbisphenol A; polyamides such as poly(p-phenylene terephthalamide); Mylar™.

In some embodiments, the centrifuge activated valve is an umbrella valve. In other embodiments, the centrifuge activated valve is a check valve. For example, the check valve may be a ball check valve, diaphragm check valve, lift check valve and a tilted disc check valve. In certain embodiments, the check valve is a ball and spring check valve, such as a ball and spring valve having a stainless steel ball and spring.

In embodiments, the centrifuge activated valve is configured to open and close in response to the force of centrifugation. In some embodiments, the valve opens in response to centrifugation. In other embodiments, the valve closes immediately when centrifugation is stopped. In still other embodiments, the valve gradually closes as centrifugation is slowed, where the valve takes a fully closed position when centrifugation is stopped.

In certain embodiments, the buoy has a first orifice at the base of the concave outer surface at the buoy proximal end, a second orifice at a position distal along the longitudinal axis of the buoy to the first orifice and a channel that extends from the first orifice to the second orifice. The first orifice and second orifice may be the same or different shape, where examples of cross-sectional shapes include, but are not limited to rectilinear cross-sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion, etc. The first orifice and the second orifice may also be the same or different size and may range from 1 mm to 50 mm, such as from 2 mm to 40 mm, such as from 3 mm to 30 mm and including from 5 mm to 25 mm. The channel extending between the first orifice and the second orifice may have the same or different cross-sectional dimensions as the first or second orifices. The channel may have the same cross-sectional shape as the first orifice, the second orifice or may have a different cross-sectional shape altogether. The length of the channel may also vary, depending on the size of the buoy and amount of liquid sample being processed, e.g., ranging from 1 mm to 100 mm, such as from 2 mm to 90 mm, such as from 3 mm to 80 mm, such as from 4 mm to 70 mm, such as from 5 mm to 60 mm and including from 10 mm to 50 mm.

In these embodiments, the buoy may also include a centrifuge activated valve (e.g., check valve) positioned at the first orifice, at the second orifice or a position therebetween, where the centrifuge activated valve is configured with an open position and closed position where the check valve fluidically seals the second orifice in the closed position. In some instances, the centrifuge activated valve is positioned at the first orifice such that in the closed position, the centrifuge activated valve fluidically seals the first orifice. In other instances, the centrifuge activated valve is positioned at the second orifice such that in the closed position, the centrifuge activated valve fluidically seals the second orifice. In still other instances, the centrifuge activated valve is positioned within the channel extending between the first orifice and the second orifice and in the closed position, forms a fluidic seal within the channel. For example, depending on the length of the channel, the centrifuge activated valve may be positioned 1 mm or more from the first orifice, such as 2 mm or more, such as 5 mm or more, such as 10 mm or more, such as 25 mm or more, such as 50 mm or more and including 100 mm or more from the first orifice, such as being positioned from 1 mm to 100 mm from the first orifice, such as from 2 mm to 90 mm, such as from 3 mm to 80 mm, such as from 4 mm to 70 mm, such as from 5 mm to 60 mm and including from 10 mm to 50 mm from the first orifice. In certain embodiments, the centrifuge activated valve is in the channel at a position that is equidistant from the first orifice and the second orifice.

As discussed above, in certain embodiments, the centrifuge activated valve is configured to open in response to an applied force of centrifugation. Any convenient centrifuge activated valve (as described above) may be employed at the second orifice and may include, but are not limited to check valves, such as ball check valves, umbrella valves, diaphragm check valves, lift check valves and a tilted disc check valves. In certain embodiments, the check valve is a mass and spring valve, such as a ball and spring check valve, including a ball and spring valve having a metal (e.g., stainless steel ball) and spring.

In embodiments, the centrifuge activated valve may be configured to open in response to the force of centrifugation. Depending on the type and size of centrifuge activated valve, the valve may be configured to open in response to a force of centrifugation (in relative centrifugal force, RCF) ranging from 1 g to 50,000 g, such as from 2 g to 45,000 g, such as from 3 g to 40,000 g, such as from 5 g to 35,000 g, such as from 10 g to 25,000 g, such as from 100 g to 20,000 g, such as from 500 g to 15,000 g and including from 1000 g to 10,000 g. As described above, subjecting the sample to a force of centrifugation (e.g., centrifuging the subject device with sample present in the container) is sufficient to open the valve and collect one or more components of the sample on the buoy, such as on the proximal end of the buoy, such as at the base of the concave outer surface of the buoy, such as adjacent to an orifice on the buoy, such as in a channel in the buoy, such as on the surface of a centrifuge activated suspension floor, such as on the surface of the ball in a ball and spring valve. In one example where the multi-component liquid sample is whole blood, subjecting the sample to a force of centrifugation is sufficient to open the centrifuge activated valve and collect buffy coat on the surface of a centrifuge activated suspension floor, such as on the surface of the ball in a ball and spring valve. In another example, the multi-component liquid sample is bone marrow aspirate and subjecting the sample to a force of centrifugation is sufficient to open the centrifuge activated valve and collect a component of the fractionated bone marrow aspirate on the surface of a centrifuge activated suspension floor, such as on the surface of the ball in a ball and spring valve.

Depending on the cross-sectional shape of the buoy, the buoy has one or more walls which extend along the longitudinal axis from the distal end to the proximal end of the buoy. The walls of the buoy, as described in greater detail below, remain in close proximity to the interior walls of the container, during displacement of the buoy along the longitudinal axis of the container. In certain embodiments, the walls of the buoy may be configured to contact (i.e., touch) the inner walls of the container during displacement in response to the force of centrifugation. The length of the walls of the buoy may vary depending on the size of the buoy as well as the size of the container. For example, the length of the walls of the buoy may range from 0.5 cm to 25 cm, such as from 1 cm to 22.5 cm, such as from 1.5 cm to 20 cm, such as from 2.5 cm to 17.5 cm and including from 5 cm to 15 cm.

In certain embodiments, the walls of the buoy may include one or more ribs. For example, the walls of the buoy may include 2 or more ribs, such as 3 or more ribs, such as 5 or more ribs, such as 10 or more ribs and including 25 or more ribs. Each rib may extend along a length of the buoy by an amount that varies, such as extending along a length of the buoy by 10% or more, such as by 25% or more, such as by 50% or more, such as by 75% or more, such as by 90% or more and including extending entirely along the length of the walls of the buoy. Depending on the length of the buoy, each rib may have a width which varies, ranging from 0.1 mm to 10 mm, such as from 0.5 mm to 9.5 mm, such as from 1 mm to 9 mm, such as from 2 mm to 8 mm and including a width from 3 mm to 5 mm, occupying between (but not including) 0 and 100% of the outer surface area of the buoy, and a length ranging from 1% to 100% of the length of the buoy.

In certain embodiments, the ribs are configured to reduce the sheer of components by the buoy during displacement along the longitudinal axis in response to the force of centrifugation. In other embodiments, the ribs may be configured to maintain alignment within the container, such as for example, where the walls of the buoy remain within 10° or less of being parallel with the inner walls of the container during displacement of the buoy in response to the force of centrifugation, such as within 7° or less, such as within 5° or less, such as within 3° or less, such as within 2° or less, such as within 1° or less, such as within 0.5° or less, such as within 0.1° or less and including within 0.05° or less of being parallel with the inner walls of the container during displacement of the buoy in response to the force of centrifugation. In certain instances, ribs on the outer walls of the buoy are configured to maintain alignment of the buoy such that the walls of the buoy remain parallel with the inner walls of the container during displacement of the buoy in response to the force of centrifugation. In certain instances, ribs on the outer walls of the buoy are configured to collide with protruding features or indentations on the inner wall of the container in order to constrain or limit axial rotation of the buoy within the container such that the buoy cannot make a full rotation without interference occurring. For example, the axial rotation of the buoy may be limited to rotation by 25° or less, such as by 20° or less, such as by 15° or less, such as by 10° or less, such as by 5° or less and including by 3° or less. In certain embodiments, ribs on the outer walls of the buoy are configured to reduce axial rotation of the buoy within the container by 50% or more as compared to a buoy without ribs on the outer walls, such as by 75% or more, such as by 90% or more and including by 95% or more.

Depending on the size of the container, the cross-sectional dimensions of the buoy may vary. For example, the cross-sectional dimensions of the buoy may range from 0.5 cm to 25 cm, such as from 1 cm to 22.5 cm, such as from 1.5 cm to 20 cm, such as from 2.5 cm to 17.5 cm and including from 5 cm to 15 cm. Where the buoy has a cylindrical cross-section, the diameter may vary, in some embodiments, ranging from 1 cm to 10 cm, such as from 2 cm to 9 cm, such as from 3 cm to 8 cm and including from 4 cm to 7 cm. Accordingly, the cross-sectional area of the buoy may vary, ranging from 1 to 500 $cm^2$, such as 5 to 250 $cm^2$, such as 10 to 200 $cm^2$, such as 15 to 150 $cm^2$, such as 20 to 125 $cm^2$ and including from 25 to 100 $cm^2$.

In embodiments, the buoy is configured to be displaced along the longitudinal axis within the container. As such, the buoy is configured to have a cross-section which is less than the cross-section of the inner cavity of the container. For example, the cross-section size of the buoy may be less than the cross-section of the inner cavity of the container by 0.001 mm or more, such as by 0.005 mm or more, such as by 0.01 mm or more, such as by 0.05 mm or more, such as by 0.1 mm or more, such as by 0.5 mm or more, such as by 1 mm or more and including by 2 mm or more. In other words, when the buoy is positioned inside the container, there is space between the outer walls of the buoy and the inner walls of the container, such as a space ranging from 0.001 mm to 5 mm, such as from 0.005 mm to 4.5 mm, such as from 0.01 mm to 4 mm, such as from 0.05 mm to 3.5 mm, such as from 0.1 mm to 3 mm and, such as from 0.5 mm to 2.5 mm and including from 1 mm to 2 mm of space between the outer walls of the buoy and the inner walls of the container.

Depending on the density of the multi-component liquid sample as well as the components therein, the buoy may be displaced proximally or displaced distally during centrifugation. In some embodiments, the buoy is configured to have a density such that after centrifugation, the buoy positions at a particular location in the fractionated sample. For example, the buoy may be configured to have a density such that after centrifugation, the buoy is positioned at the interface between two fractionated components. In other embodiments, the buoy may be configured to have a density such that after centrifugation, the buoy is positioned within a predetermined fraction, such as within a bottommost fraction, such as within an uppermost fraction or within some fraction in between. In yet other embodiments, the buoy may be configured to have a density such that after centrifugation, the buoy is positioned at the bottom of the container. In still other embodiments, the buoy may be configured to have a density such that after centrifugation, the buoy is positioned at the top of the container. Depending on the multi-component liquid sample, the buoy has a density which varies, ranging from 0.1 g/mL to 2 g/mL, such as from 0.2 g/mL to 1.95 g/mL, such as from 0.3 g/mL to 1.9 g/mL, such as from 0.4 g/mL to 1.85 g/mL, such as from 0.5 g/mL to 1.8 g/mL, such as from 0.6 g/mL to 1.75 g/mL, such as from 0.7 g/mL to 1.7 g/mL, such as from 0.8 g/mL to 1.6 g/mL and including a buoy density of from 1 g/mL to 1.5 g/mL and including a buoy density from 1.04 g/mL to 1.10 g/mL. For example, the buoy may have a density that ranges from 1.01 g/mL to 1.2 g/mL, such as from 1.04 g/mL to 1.07 g/mL and including from 1.045 g/mL to 1.060 g/mL. In certain embodiments, the density of the buoy is 1.055 g/mL.

For example, in some instances the multi-component liquid sample is a blood or bone marrow aspirate sample and the buoy is configured to have a density such that after centrifugation, the buoy is positioned at an interface between red blood cells and plasma. In other instances, the buoy is configured to have a density such that after centrifugation, the buoy is positioned a level in the fractionated blood sample occupied by the buffy coat. In certain instances, the buoy is configured to have a density that is greater than whole blood (density 1.06 g/mL) but less than red blood cells (density 1.09 g/mL to 1.11 g/ml), such as a density ranging from 1.061 g/mL to 1.09 g/mL.

The buoy may be formed from any suitable material including, but not limited to, glass, metal or plastic, such as a flexible or rigid plastic, polymeric or thermoplastic materials. For example, suitable polymeric plastics may include polycarbonates, polyvinyl chloride (PVC), polyurethanes, polyethers, polyamides, polyimides, or copolymers of these thermoplastics, such as PETG (glycol-modified polyethylene terephthalate), among other polymeric plastic materials. In certain embodiments, the container is formed from a polyester, where polyesters of interest may include, but are not limited to, housings made of poly(alkylene terephthalates) such as poly(ethylene terephthalate) (PET), bottle-grade PET (a copolymer made based on monoethylene glycol, terephthalic acid, and other comonomers such as isophthalic acid, cyclohexene dimethanol, etc.), poly(butylene terephthalate) (PBT), and poly(hexamethylene terephthalate); poly(alkylene adipates) such as poly(ethylene adipate), poly(1,4-butylene adipate), and poly(hexamethylene adipate); poly(alkylene suberates) such as poly(ethylene suberate); poly(alkylene sebacates) such as poly(ethylene sebacate); poly(E-caprolactone) and poly(p-propiolactone); poly(alkylene isophthalates) such as poly(ethylene isophthalate); poly(alkylene 2,6-naphthalene-dicarboxylates) such as poly(ethylene 2,6-naphthalene-dicarboxylate); poly(alkylene sulfonyl-4,4'-dibenzoates) such as poly(ethylene sulfonyl-4,4'-dibenzoate); poly(p-phenylene alkylene dicarboxylates) such as poly(p-phenylene ethylene dicarboxylates); poly(trans-1,4-cyclohexanediyl alkylene dicarboxylates) such as poly(trans-1,4-cyclohexanediyl ethylene dicarboxylate); poly(1,4-cyclohexane-dimethylene alkylene dicarboxylates) such as poly(1,4-cyclohexane-dimethylene ethylene dicarboxylate); poly([2.2.2]-bicyclooctane-1,4-dimethylene alkylene dicarboxylates) such as poly([2.2.2]-bicyclooctane-1,4-dimethylene ethylene dicarboxylate); lactic acid polymers and copolymers such as (S)-polylactide, (R,S)-polylactide, poly(tetramethylglycolide), and poly(lactide-co-glycolide); and polycarbonates of bisphenol A, 3,3'-dimethylbisphenol A, 3,3',5,5'-tetrachlorobisphenol A, 3,3', 5,5'-tetramethylbisphenol A; polyamides such as poly(p-phenylene terephthalamide); Mylar™

As summarized above, devices for separating components of a multi-component liquid sample according to certain embodiments include a container configured with a buoy that can be displaced along a longitudinal axis within the container. The container has a distal end and a proximal end with walls between the distal end and proximal end that together form an inner cavity within the container such that the buoy can freely be displaced along the longitudinal axis of the container during centrifugation without resistance by the walls of the container. In some embodiments, the outer walls of the container and inner cavity have the same cross-sectional shape where cross-sectional shapes of interest include, but are not limited to curvilinear cross-sectional shapes, e.g., circles, ovals, rectilinear cross sectional shapes, e.g., squares, rectangles, trapezoids, triangles, hexagons, etc., as well as irregular shapes, e.g., a parabolic bottom portion coupled to a planar top portion. For example, both the outer walls of the container and the inner cavity may have circular or oval cross sections or both the outer walls of the container and the inner cavity may have polygonal (e.g., octagonal) cross sections. In other embodiments, the outer walls and inner cavity of the container have different cross-sectional shapes (e.g., container having a polygonal cross-section and inner chamber having a circular cross-section). In certain embodiments, the container is a tube and the cross-sectional shape the outer walls and the inner walls are both circular.

The size of the inner cavity of the container may vary, where in some instances the length of the inner cavity of the container may range from 1 cm to 25 cm, such as from 2.5 cm to 22.5 cm, such as from 5 cm to 20 cm, such as from 7.5 cm to 17.5 cm and including from 10 cm to 15 cm and the width of the inner cavity of the container may range from 1 cm to 20 cm, such as from 2 cm to 17.5 cm, such as from 3 cm to 15 cm, such as from 4 cm to 12.5 cm and including from 5 cm to 10 cm. Where the inner cavity of the container has a cylindrical cross-section, the diameter may vary, in some embodiments, ranging from 1 cm to 10 cm, such as from 2 cm to 9 cm, such as from 3 cm to 8 cm and including from 4 cm to 7 cm. Accordingly, the volume of the container may vary, ranging from 1 to 500 cm$^3$, such as 5 to 250 cm$^3$, such as 10 to 200 cm$^3$, such as 15 to 150 cm$^3$, such as 20 to 125 cm$^3$ and including from 25 to 100 cm$^3$. In some embodiments, the container of the subject separation devices is a tube having a volume ranging from 1 mL to 500 mL, such as from 2 mL to 400 mL, such as from 3 mL to 300 mL, such as from 4 mL to 200 mL, such as from 5 mL to 150 mL and including from 10 mL to 100 mL.

In certain embodiments, the container may include one or more reference identifiers (i.e., markings), such as for measuring the volume of one or more components of the sample or for providing guidance in removing a predetermine amount of the sample from the container (as described in greater detail below). In some embodiments, the markings make reference to volume, such as references in units of milliliters of sample. In certain embodiments, the container includes one or more reference identifiers which provide for removal of a predetermined amount of sample from the container, such as a removal of 10% or more of the sample, such as 25% or more of the sample, such as 50% or more of the sample, such as 75% or more of the sample and including 90% or more of the sample. In other embodiments, the container includes one or more reference identifiers which provide for removal of a predetermined amount of a particular separated fraction from the centrifuged sample, such as 10% or more from a particular fraction, such as 25% or more from a particular fraction, such as 50% or more from a particular fraction, such as 75% or more from a particular fraction and including 90% or more from a particular fraction. For example, in certain embodiments, the multi-component liquid sample is whole blood or bone marrow aspirate and containers of interest include one or more reference identifiers which provide for removal of a predetermined amount of the plasma fraction of the centrifuged whole blood sample, such as 10% or more of the plasma fraction, such as 25% or more of the plasma fraction, such as 50% or more of the plasma fraction, such as 75% or more of the plasma fraction and including 90% or more of the plasma fraction. Any suitable type of marking on the container may be used, such as for example, printed markings on the inside or outside of the container, or markings which are etched into the container walls.

The container may be formed from any suitable material including, but not limited to, glass, metal or plastic, such as a flexible or rigid plastic, polymeric or thermoplastic materials. For example, suitable polymeric plastics may include polycarbonates, polyvinyl chloride (PVC), polyurethanes, polyethers, polyamides, polyimides, or copolymers of these thermoplastics, such as PETG (glycol-modified polyethylene terephthalate), among other polymeric plastic materials. In certain embodiments, the container is formed from a polyester, where polyesters of interest may include, but are not limited to, housings made of poly(alkylene terephthalates) such as poly(ethylene terephthalate) (PET), bottle-grade PET (a copolymer made based on monoethylene glycol, terephthalic acid, and other comonomers such as isophthalic acid, cyclohexene dimethanol, etc.), poly(butylene terephthalate) (PBT), and poly(hexamethylene terephthalate); poly(alkylene adipates) such as poly(ethylene adipate), poly(1,4-butylene adipate), and poly(hexamethylene adipate); poly(alkylene suberates) such as poly(ethylene suberate); poly(alkylene sebacates) such as poly(ethylene sebacate); poly(£-caprolactone) and poly([3-propiolactone); poly(alkylene isophthalates) such as poly(ethylene isophthalate); poly(alkylene 2,6-naphthalene-dicarboxylates) such as poly(ethylene 2,6-naphthalene-dicarboxylate); poly(alkylene sulfonyl-4,4'-dibenzoates) such as poly(ethylene sulfonyl-4,4'-dibenzoate); poly(p-phenylene alkylene dicarboxylates) such as poly(p-phenylene ethylene dicarboxylates); poly(trans-1,4-cyclohexanediyl alkylene dicarboxylates) such as poly(trans-1,4-cyclohexanediyl ethylene dicarboxylate); poly(1,4-cyclohexane-dimethylene alkylene dicarboxylates) such as poly(1,4-cyclohexane-dimethylene ethylene dicarboxylate); poly([2.2.2]-bicyclooctane-1,4-dimethylene alkylene dicarboxylates) such as poly([2.2.2]-bicyclooctane-1,4-dimethylene ethylene dicarboxylate); lactic acid polymers and copolymers such as (S)-polylactide, (R,S)-polylactide, poly(tetramethylglycolide), and poly(lactide-co-glycolide); and polycarbonates of bisphenol A, 3,3'-dimethylbisphenol A, 3,3',5,5'-tetrachlorobisphenol A, 3,3', 5,5'-tetramethylbisphenol A; polyamides such as poly(p-phenylene terephthalamide); Mylar™.

Depending on the type of container employed, the opacity of the container to visible light may vary. In some embodiments, containers of interest are transparent. In other embodiments, containers are translucent to visible light. In yet other embodiments, containers are opaque to visible light.

In some embodiments, containers of the subject separation devices also include a cap configured to close off the proximal end of the container. For example, the cap may be a screw cap, a snap-on cap or a cap which connects the container by a permanent, semi-permanent or non-permanent adhesive. In certain instances, the cap forms a fluidic seal with the walls of the container. The cap may be an integrated part of the container, including where the cap is molded with, soldered, welded or affixed to the container using a permanent adhesive. In other embodiments, the cap is releasably attached to the container. By "releasably" is meant that the cap can be freely detached from and re-attached to the proximal end of the container. Where the cap is releasably attached to the container, the cap may be non-permanently fastened to the container by any convenient attachment protocol, including but not limited to a hook and loop fastener, a latch, a notch, a groove, a pin, a tether, a hinge, Velcro, non-permanent adhesive, a threaded screw, or a combination thereof. In certain instances, the container includes a threaded outer wall and is screw threaded with the internal walls of the cap.

The cap may include one or more ports into the inner cavity of the container, such as 2 or more ports, such as 3 or more ports, such as 4 or more ports and including 5 or more ports. In certain embodiments, the cap includes only a single port. The ports may be any convenient port configured for fluidic or gaseous communication with the inner cavity of the container. In some embodiments, the cap includes a port for introducing the multi-component liquid sample into the container or a port for collecting components of the liquid after centrifugation (as described below). In certain embodiments, the cap includes a vent port configured to allow gas into and out of the container. In some instances, the container includes a second opening in the cap to allow air to vent during sample introduction and removal. Where the cap includes a single port, the port is configured for both introducing the multi-component liquid sample into the container and for collecting one or more components from the cavity of the container after centrifugation.

Any suitable port configuration may be employed depending on the desired function of the port, where examples of ports include channels, orifices, channels having a check valve, a Luer taper fitting, a port with a breakable seal (e.g., single use ports) among other types of ports. In some embodiments, the port is configured to connect to a syringe, such as for example to introduce a multi-component liquid sample (e.g., blood) into the container or to remove one or more components from the container after centrifugation. In other embodiments, the port is configured to facilitate access for a needle into the cavity of the container to aspirate, mix and remove components from the container after centrifugation. In certain embodiments, the port is configured with a Luer taper fitting, such as a Luer-Lok or a Luer-slip.

Ports in the cap of the subject separation devices may be any suitable shape, where cross-sectional shapes of ports of interest include, but are not limited to rectilinear cross-sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion. The dimensions of the ports may vary, in some embodiments ranging from 1 mm to 100 mm, such as from 2 mm to 95 mm, such as from 3 mm to 90 mm, such as from 4 mm to 80 mm, such as from 5 mm to 70 mm, such as from 6 mm to 60 mm and including from 10 mm to 50 mm. In some embodiments, the port is a circular orifice and the diameter of the port ranges from 1 mm to 100 mm, such as from 2 mm to 90 mm, such as from 4 mm to 80 mm, such as from 5 mm to 70 mm, such as from 6 mm to 60 mm and including from 10 mm to 50 mm. Accordingly, depending on the shape of the ports, ports in the cap may have an opening which ranges from 0.01 mm$^2$ to 250 mm$^2$, such as from 0.05 mm$^2$ to 200 mm$^2$, such as from 0.1 mm$^2$ to 150 mm$^2$, such as from 0.5 mm² to 100 mm², such as from 1 mm² to 75 mm², such as from 2 mm² to 50 mm² and including from 5 mm² to 25 mm².

In some embodiments, one or more of the ports in the cap are configured to be releasably attached to a syringe. For example, the cap may be configured to be non-permanently fastened to a syringe by a notch, a groove, a hook and loop fastener, Velcro, an adhesive, a threaded screw or a combination thereof. In some instances, the cap is configured to be releasably attached to the syringe by inserting the syringe into the orifice of the port. In other instances, the cap is configured to be screw threaded with the syringe. In yet other instances, the cap is configured with a Luer taper fitting (e.g., Luer-Lok, Luer slip, etc.) and the syringe is releasably attached to the port in the cap through the Luer taper fitting.

FIG. 1 illustrates an example of a device for separating components of a multi-component liquid (e.g., blood) according to certain embodiments. Device 100 includes a buoy 101 positioned inside of container 102. Buoy 101 includes one or more sealed chambers 103 containing a gas and concave outer surface 104 at the proximal end. At the base of the concave outer surface of the buoy proximal end is a first orifice 105 in fluid communication with channel 106 and second orifice 107. Second orifice 107 is sealed by ball-and-spring check valve 108 in the closed position. Device 100 also includes a cap 109 positioned at the proximal end of the container. Cap 109 includes two ports, 109a and 109b. Port 109a is a vent port for gas flow into and out of the device. Port 109b is an inlet/outlet for introducing multi-component liquid sample 110 (e.g., blood) into container 100 or for removing one or more components after separating the multi-component liquid sample by centrifugation, as described below.

Figure 2:
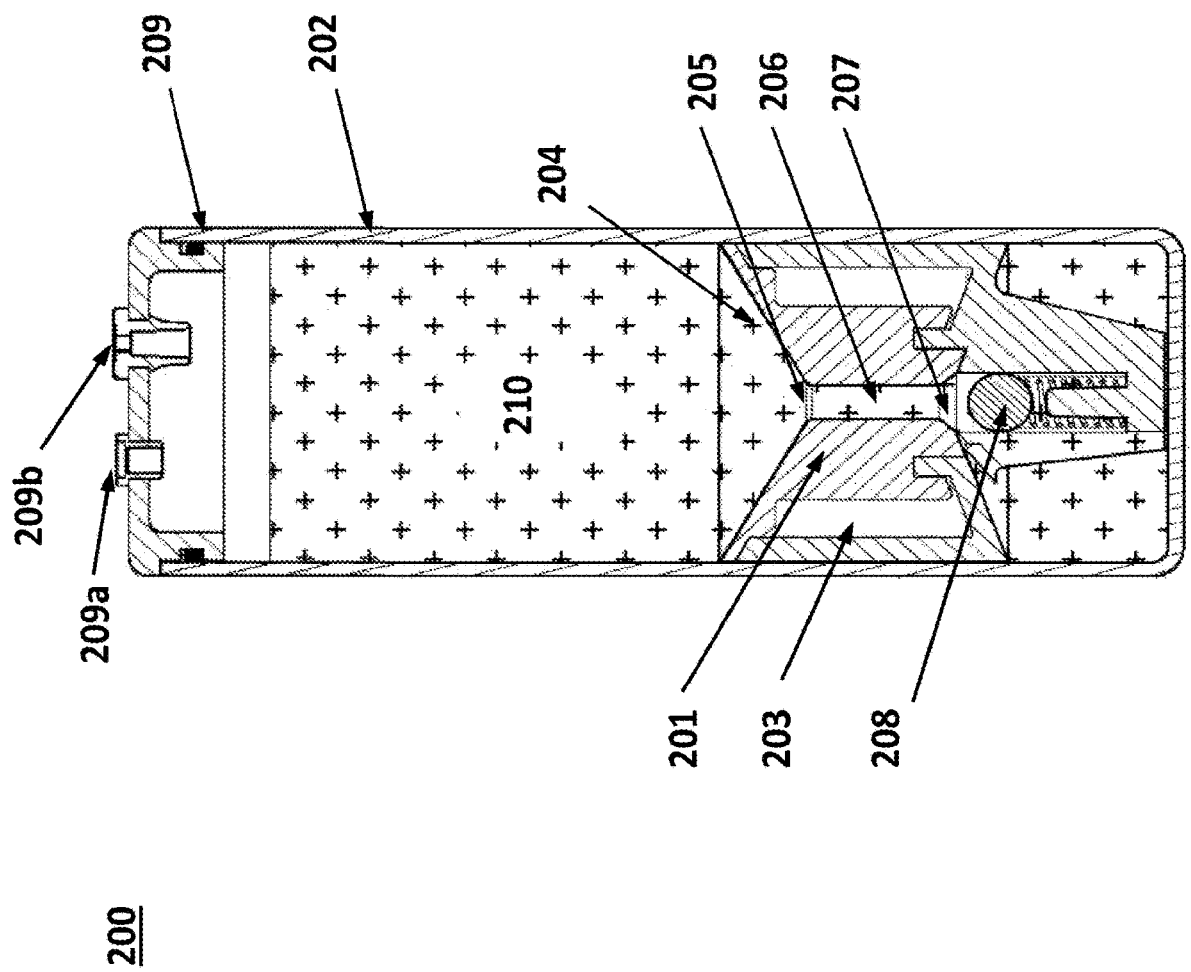
FIG. 2 depicts a side-view of a separation device having a buoy positioned inside of a container having a ball-and-spring valve according to certain embodiments.

FIG. 2 illustrates an example of a device for separating components of a multi-component liquid according to another embodiment. Device 200 includes buoy 201 positioned inside of container 202. At the base of the concave outer surface of the buoy proximal end is a first orifice 205 in fluid communication with channel 206 and second orifice 207. Second orifice 207 is adjacent to ball-and-spring check valve 108 in the open position. Buoy 201 includes one or more sealed chambers 203 containing a gas and concave outer surface 204 at the proximal end. Device 200 also includes a cap 209 positioned at the proximal end of the container which includes two ports, vent port 209a for gas flow into and out of the device and inlet/outlet port 209b for introducing multi-component liquid sample 210 (e.g., blood) into container 200 or for removing one or more components after separating the multi-component liquid sample by centrifugation.

In certain embodiments, the container also includes a conduit that extends from one or more of the ports in the cap to the proximal end of the buoy. In these embodiments, the port in the cap is in fluid communication with the proximal end of the buoy through the conduit. Put another way, the conduit includes two openings, a first opening in fluid communication with the port in the cap and a second opening in fluid communication with the proximal end of the buoy. The conduit may be integrated with or may be releasably attached to one or more of the port and the proximal end of the buoy. In some embodiments, the conduit is integrated with both the port in the cap and the buoy proximal end. The conduit may be integrated such as by co-molding, soldering, welding or affixing the conduit using a permanent adhesive. In other embodiments, the conduit is releasably attached to both the port in the cap and the proximal buoy end. The conduit may be releasably attached such as by non-permanently fastening with a notch, groove, snap-on, hook and loop fastener, Velcro, a threaded screw or with a nonpermanent adhesive. In yet other embodiments, the conduit is integrated with the port in the cap and releasably attached to the proximal end of the buoy. In still other embodiments, the conduit is releasably attached to the port in the cap and integrated with the proximal end of the buoy. Depending on the size of the sample, the configuration of the conduit may vary. In some embodiments, the conduit is a linear tube extending from the port in the cap to the buoy proximal end. In other embodiments, the conduit is non-linear. For example, the conduit may be curvilinear, circular, winding, coiled, twisted or have a helical configuration.

In certain embodiments, the conduit is flexible. The term "flexible" is used in its conventional sense to mean that the conduit is capable of being bent without breaking or otherwise able to be turned, bowed, or twisted, without breaking. In these embodiments, the conduit may be pliable and is not rigid or stiff. In other embodiments, the conduit is rigid. The term "rigid" is used in its conventional sense to mean that the conduit is stiff and not capable of substantially being bent without breaking.

Depending on the chemical constitution of specific conduits employed, the durometer hardness of conduits of interest may vary. In certain embodiments, the durometer hardness of conduits ranges from 10 Shore 00 to 100 Shore 00, such as 20 Shore 00 to 90 Shore 00, such as 30 Shore 00 to 80 Shore 00 and including 40 Shore 00 to 70 Shore 00. In other embodiments, the durometer hardness of conduits of interest ranges from 10 Shore A to 100 Shore A, such as 20 Shore A to 90 Shore A, such as 30 Shore A to 80 Shore A and including 40 Shore A to 70 Shore A.

The length of the conduit may vary, ranging from 1 cm to 100 cm, such as from 2 cm to 95 cm, such as from 3 cm to 90 cm, such as from 4 cm to 85 cm, such as from 5 cm to 80 cm, such as from 6 cm to 75 cm, such as from 7 cm to 70 cm, such as from 8 cm to 65 cm, such as from 9 cm to 60 cm, such and including from 10 cm to 50 cm. In embodiments, the cross-sectional shape of the conduit may vary, where examples of cross-sectional shapes include, but are not limited to rectilinear cross-sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion, etc. The cross-sectional dimensions of the conduit may range from 0.01 mm to 25 mm, such as from 0.05 mm to 22.5 mm, such as from 0.1 mm to 20 mm, such as from 0.5 mm to 17.5 mm, such as from 1 mm to 15 mm, such as from 2 mm to 12.5 mm, such as from 3 mm to 10 mm and including from 5 mm to 10 mm. For example, where the conduit is a tube, the diameter of the conduit may range from 0.01 mm to 25 mm, such as from 0.05 mm to 22.5 mm, such as from 0.1 mm to 20 mm, such as from 0.5 mm to 15 mm, such as from 1 mm to 10 mm and including from 3 mm to 5 mm.

As discussed above, the conduit extends from a port in the cap to the buoy proximal end. The opening of the conduit may be positioned at any location on the proximal end of the buoy. For example, in some embodiments, the conduit opening is positioned adjacent to the base of the concave outer surface (e.g., adjacent to the orifice) of the buoy proximal end, such as 1 mm or more from the base of the outer concave surface, such as 2 mm or more, such as 3 mm or more, such as 4 mm or more and including 5 mm or more from the base of the outer concave surface. In other embodiments, the conduit opening is positioned along the outer edge of the buoy proximal end, such as at a position adjacent to the inner wall of the container. In still other embodiments, the conduit opening is positioned between the outer edge of the buoy proximal end and the base of the concave outer surface of the buoy proximal end, such as 1 mm or more from the outer edge of the buoy proximal end, such as 2 mm or more, such as 3 mm or more, such as 4 mm or more, such as 5 mm or more and including being positioned 10 mm or more from the outer edge of the buoy proximal end.

In certain embodiments, the opening of the conduit in fluid communication with the proximal end of the buoy includes a stream modulator. The stream modulator may be any suitable component which is coupled to the opening of the conduit at the proximal end of the buoy and may be configured to regulate the output of fluid from the conduit (e.g., when introducing the multi-component fluid into the container or when reintroducing one or more fractions to the proximal end of the buoy). The stream modulator may be a separate component which is attached to the conduit, such as with an adhesive or fastener or may be fully integrated with the conduit, such as by co-molding, soldering or welding the stream modulator to the conduit.

In embodiments, the stream modulator is in fluid communication with the proximal end of the buoy. In certain instances, the stream modulator is physically attached (e.g., by an adhesive or other fastener) to the proximal end of the buoy. In certain embodiments, the stream modulator is integrated directed into the buoy, such as where the stream modulator is molded with, soldered, welded or affixed to the buoy using a permanent adhesive.

The stream modulator may be configured to regulate the output flow rate of fluid from the conduit to the proximal end of the buoy. For example, the stream modulator may be configured to increase the output flow rate of fluid from the conduit to the proximal end of the buoy, such as by increasing the flow rate by 0.01 mL/second or more, such as by 0.1 mL/second or more, such as by 1 mL/second or more, such as by 5 mL/second or more, such as by 10 mL/second or more, such as by 25 mL/second or more, such as by 50 mL/second or more, such as by 100 mL/second or more, such as by 250 mL/second or more and including by 500 mL/second or more. For example, the stream modulator may be configured to increase the output flow rate of fluid from the conduit to the proximal end of the buoy by 1% or more, such as by 5% or more, such as by 10% or more, such as by 15% or more, such as by 25% or more, such as by 50% or more, such as by 75% or more and including increasing the output flow rate of fluid from the conduit to the proximal end of the buoy by 90% or more. In other instances, the stream modulator may be configured to decrease the output flow rate of fluid from the conduit to the proximal end of the buoy, such as by decreasing the flow rate by 0.01 mL/second or more, such as by 0.1 mL/second or more, such as by 1 mL/second or more, such as by 5 mL/second or more, such as by 10 mL/second or more, such as by 25 mL/second or more, such as by 50 mL/second or more, such as by 100 mL/second or more, such as by 250 mL/second or more and including by 500 mL/second or more. For example, the stream modulator may be configured to decrease the output flow rate of fluid from the conduit to the proximal end of the buoy by 5% or more, such as by 10% or more, such as by 15% or more, such as by 25% or more, such as by 50% or more, such as by 75% or more and including decreasing the output flow rate of fluid from the conduit to the proximal end of the buoy by 90% or more.

In other embodiments, the stream modulator is configured to regulate the pressure of fluid outputted from the conduit to the proximal end of the buoy. In some instances, the stream modulator increases the pressure of fluid outputted from the conduit to the proximal end of the buoy, such as by 5% or more, such as by 10% or more, such as by 15% or more, such as by 25% or more, such as by 50% or more, such as by 75% or more and including increasing the pressure of fluid outputted from the conduit to the proximal end of the buoy by 90% or more. In other instances, the stream modulator decreases the pressure of fluid outputted from the conduit to the proximal end of the buoy, such as by 5% or more, such as by 10% or more, such as by 15% or more, such as by 25% or more, such as by 50% or more, such as by 75% or more and including decreasing the pressure of fluid outputted from the conduit to the proximal end of the buoy by 90% or more.

The stream modulator may have an orifice having any convenient shape, depending on the desired shape of the outputted flow stream to the proximal end of the conduit. For example, the cross-sectional shape of the stream modulator orifice may include, but is not limited to rectilinear cross-sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion, etc. The stream modulator orifice may have the same dimensions as cross-sectional dimensions of the conduit or may have different dimensions. In some embodiments, the orifice of the stream modulator has dimensions that are the same as the cross-sectional dimensions of the conduit. In other embodiments, the orifice of the stream modulator has different dimensions from the cross-sectional dimensions of the conduit. In one example, the stream modulator has an orifice that is larger than the cross-sectional dimensions of the conduit. In another example, the stream modulator has an orifice that is smaller than the cross-sectional dimensions of the conduit. For example, the orifice of the stream modulator may be 5% smaller or more than the cross-section of the conduit, such as 10% or more, such as 25% or more, such as 50% or more and including 75% or more. In certain embodiments, the orifice of the stream modulator ranges from 0.01 mm to 25 mm, such as from 0.05 mm to 22.5 mm, such as from 0.1 mm to 20 mm, such as from 0.5 mm to 17.5 mm, such as from 1 mm to 15 mm, such as from 2 mm to 12.5 mm, such as from 3 mm to 10 mm and including from 5 mm to 10 mm.

In certain embodiments, the stream modulator may include one or more protrusions, such as a protrusion which directs fluid from the conduit to the orifice of the buoy. The protrusions may be physically coupled to one or more of the stream modulator and the proximal end of the buoy. In certain instances, the protrusion for directing fluid from the conduit to the orifice of the buoy is incorporated into the stream modulator. In other instances, the protrusion is affixed to the stream modulator with a fastener, such as with an adhesive, a latch, snap-fitted or with screw threads.

Figure 3B:
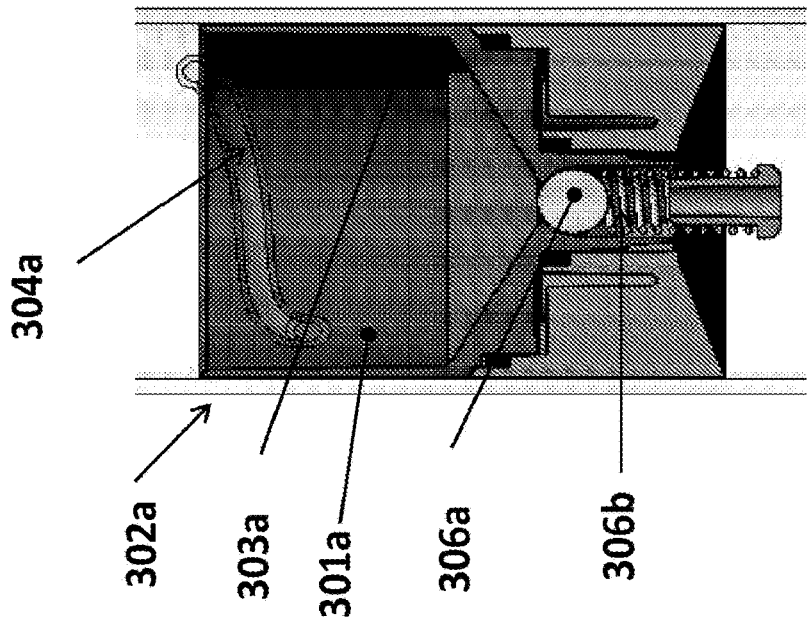
FIG. 3B illustrates a side view of an example of a device for separating components of a multi-component liquid according to certain embodiments.
Figure 3A:
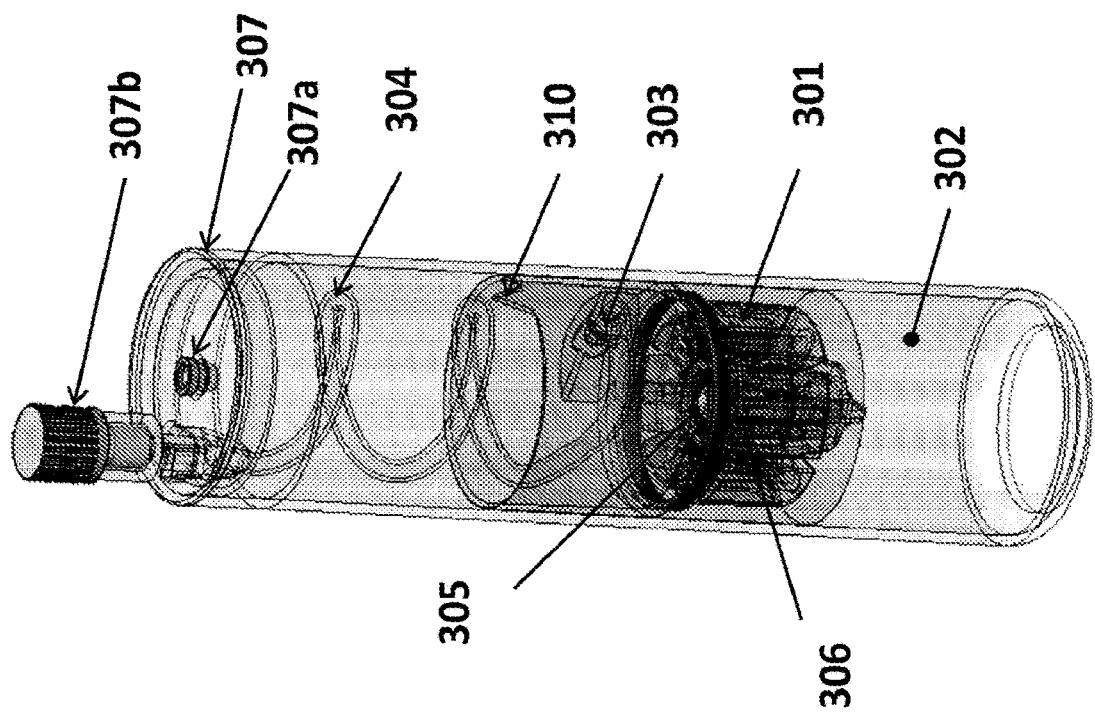
FIG. 3A illustrates a three-dimensional view of an example of a device for separating components of a multi-component liquid according to certain embodiments.

FIG. 3A illustrates a three-dimensional view of an example of a device for separating components of a multi-component liquid according to certain embodiments. Device 300 includes buoy 301 positioned inside of container 302. At the upper edge of the proximal end of the buoy is port 303 connecting conduit 304 to the proximal end of the buoy 301. At the base of the concave outer surface of buoy 301 proximal end is an orifice 305 adjacent to ball-and-spring check valve 306 in the open position. Device 300 also includes a cap 307 positioned at the proximal end of the container which includes two ports, vent port 307a for gas flow into and out of the device and inlet/outlet port 307b connected to conduit 304 for introducing a multi-component liquid sample (e.g., blood) into container 300 or for removing one or more components after separating the multi-component liquid sample by centrifugation. Device 300 also includes an angular position indicator 310 for indicating the angle position of the device when placed on a support when collecting one or more of the separated components (as described in greater detail below).

FIG. 3B illustrates a side view of an example of a device for separating components of a multi-component liquid according to certain embodiments. As described in FIG. 3A, device 300a includes buoy 301a positioned inside of container 302a. At the upper edge of the proximal end of the buoy is port 303a connecting conduit 304a to the proximal end of the buoy 301a. At the base of the concave outer surface of the buoy proximal end is an orifice 305a adjacent to ball-and-spring check valve which includes ball 306a and spring 306b. In this example, buoy 301a includes a concave outer surface at the distal end.

Figure 3D:
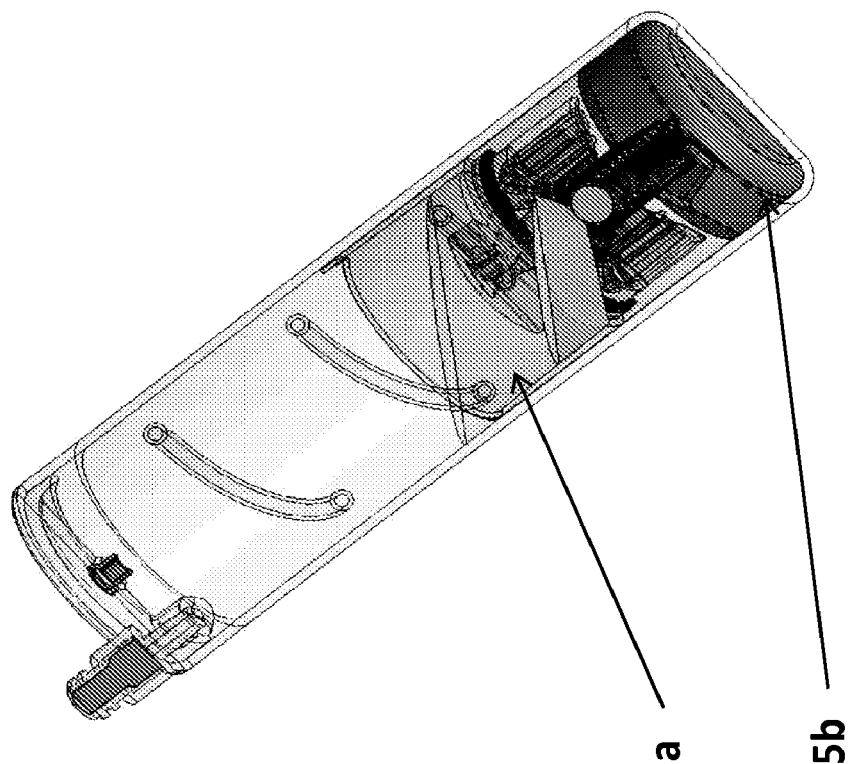
FIG. 3D illustrates an example of a device having a multi-component liquid separated into two or more regions (i.e., fractions) according to certain embodiments.
Figure 3C:
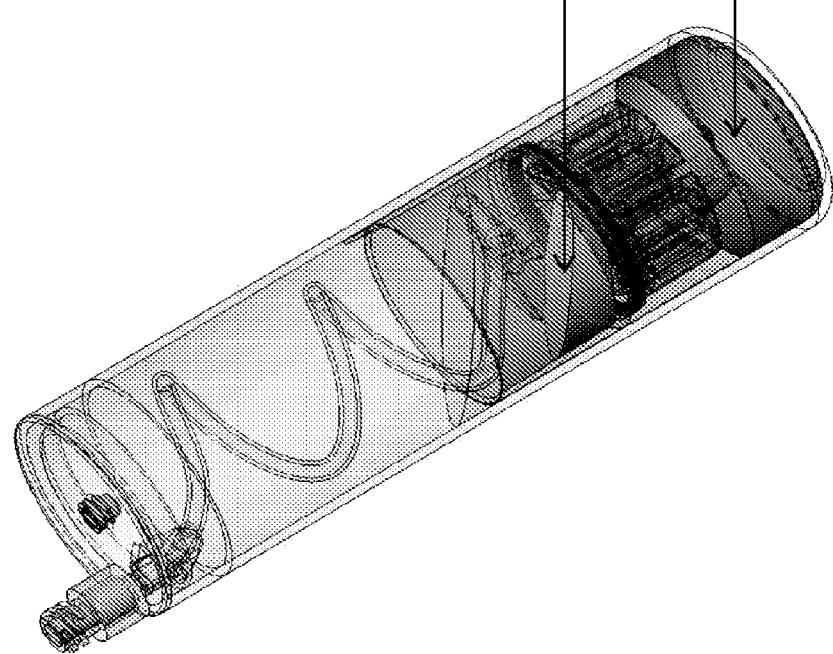
FIG. 3C illustrates an example of a device having a multi-component liquid separated into two or more regions (i.e., fractions) according to certain embodiments.

FIGS. 3C-3D illustrate a three-dimensional perspective of an example of a device having a multi-component liquid separated into two or more regions (i.e., fractions) according to certain embodiments. The components of device 300 are similar to those as described above in FIGS. 3A and 3B. As shown in FIGS. 3C and 3D, the multicomponent liquid (e.g., blood) is separated into a plurality of fractions 315a and 315b.

Figure 4B:
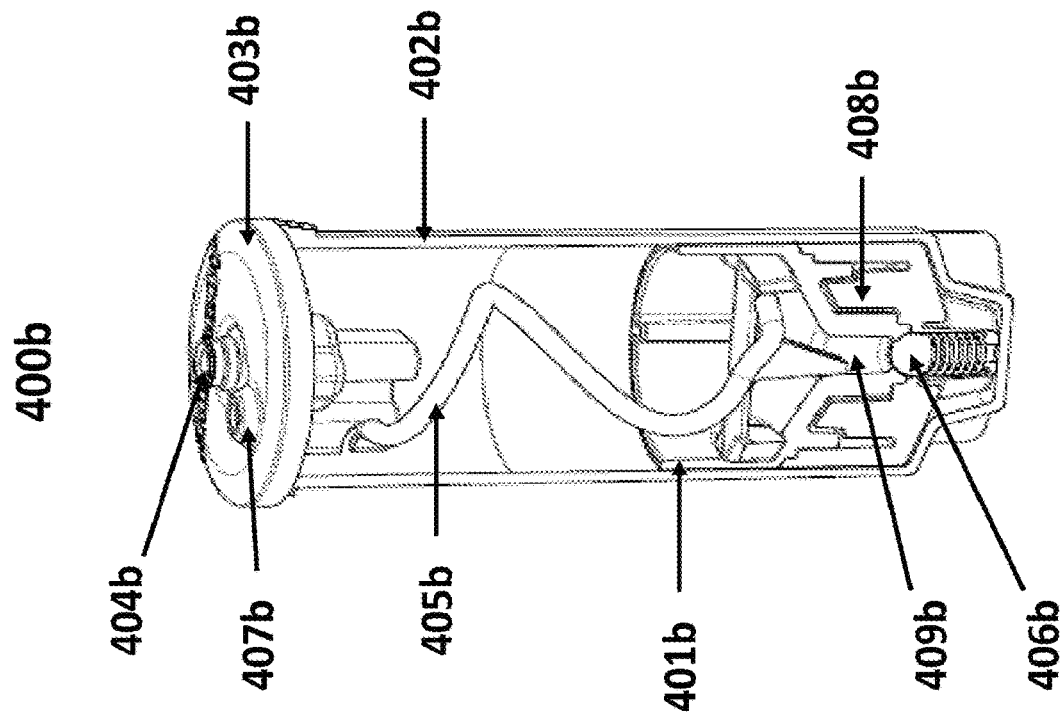
FIG. 4B depicts a three-dimensional view of a device for separating components of a multi-component liquid according to certain embodiments.
Figure 4A:
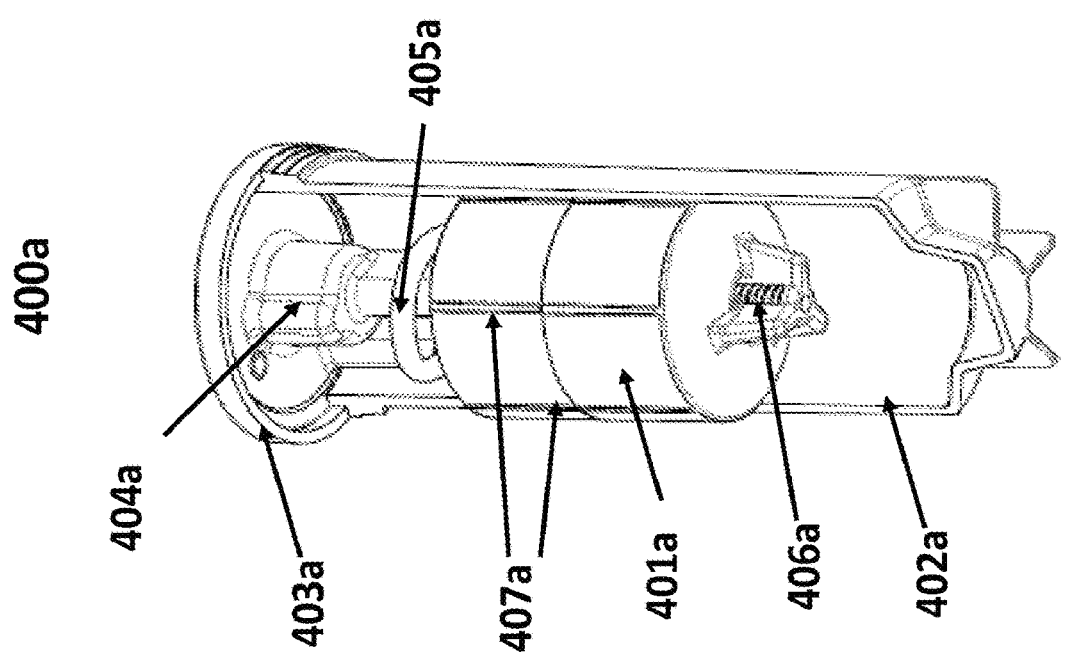
FIG. 4A depicts a three-dimensional view of a device for separating components of a multi-component liquid according to certain embodiments.

FIGS. 4A and 4B depict two different three-dimensional views of a device for separating components of a multi-component liquid according to certain embodiments. FIG. 4A illustrates a bottom-view three-dimensional perspective of device 400a which includes buoy 401a positioned inside of container 402a that is covered by lid 403a. The lid includes a single self-sealing port 404a for inputting a multicomponent sample and aspirating one or more fractions after centrifugation. Port 404a is in fluid communication with the proximal end of buoy 401a through conduit 405a. Buoy 401a also includes ribs 407a along the outer walls to aid in fluid bypass during displacement of the buoy along the longitudinal axis of container 402a during centrifugation. Buoy 401a also includes a centrifuge activated ball and spring valve 406a.

FIG. 4B illustrates a top-view three-dimensional perspective of device 400b which includes buoy 401b positioned inside of container 402b that is covered by lid 403b. Buoy 401b has one or more sealed chambers 408b that can include a fluidic composition or a vacuum. Lid 403b includes a single port 404b for inputting a multicomponent sample and aspirating one or more fractions. Port 404b is in fluid communication with buoy 401b through conduit 405b which is connected to the proximal end of the buoy. Lid 403b also includes an air vent 407b. Ball and spring valve 406b is positioned at the distal end of buoy 401b and fluidically seals a second orifice at the bottom of channel 409b.

Figure 4D:
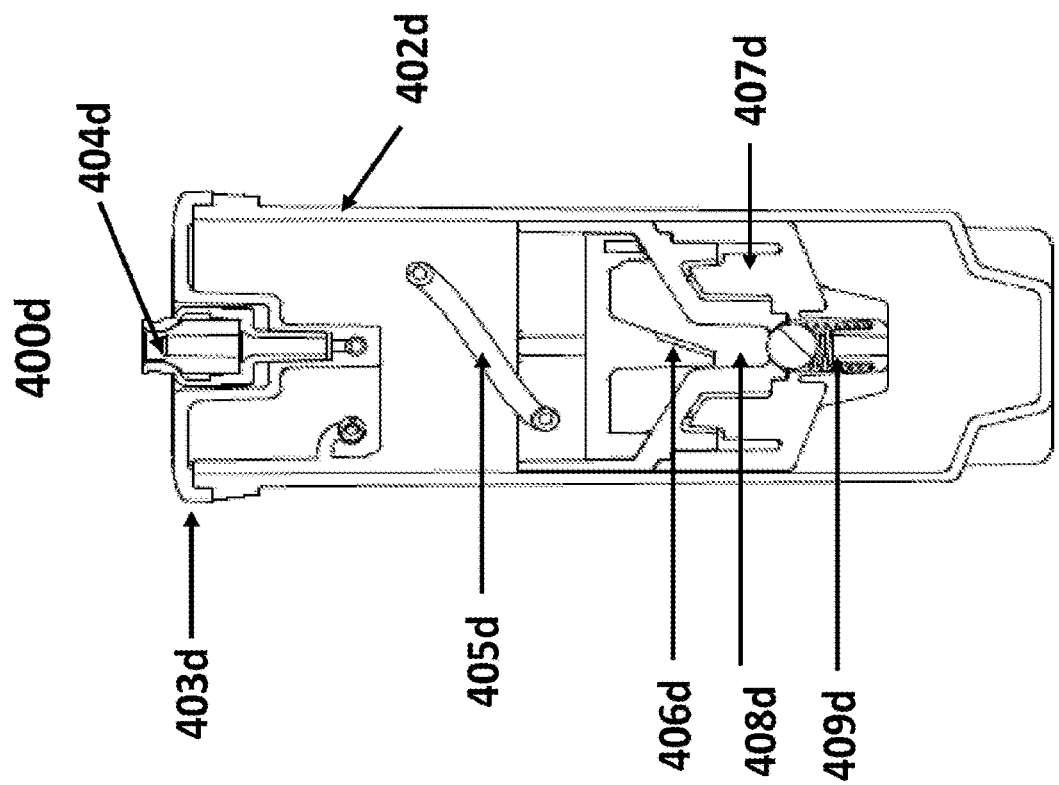
FIG. 4D depicts a different side view of a device for separating components of a multi-component liquid according to certain embodiments.
Figure 4C:
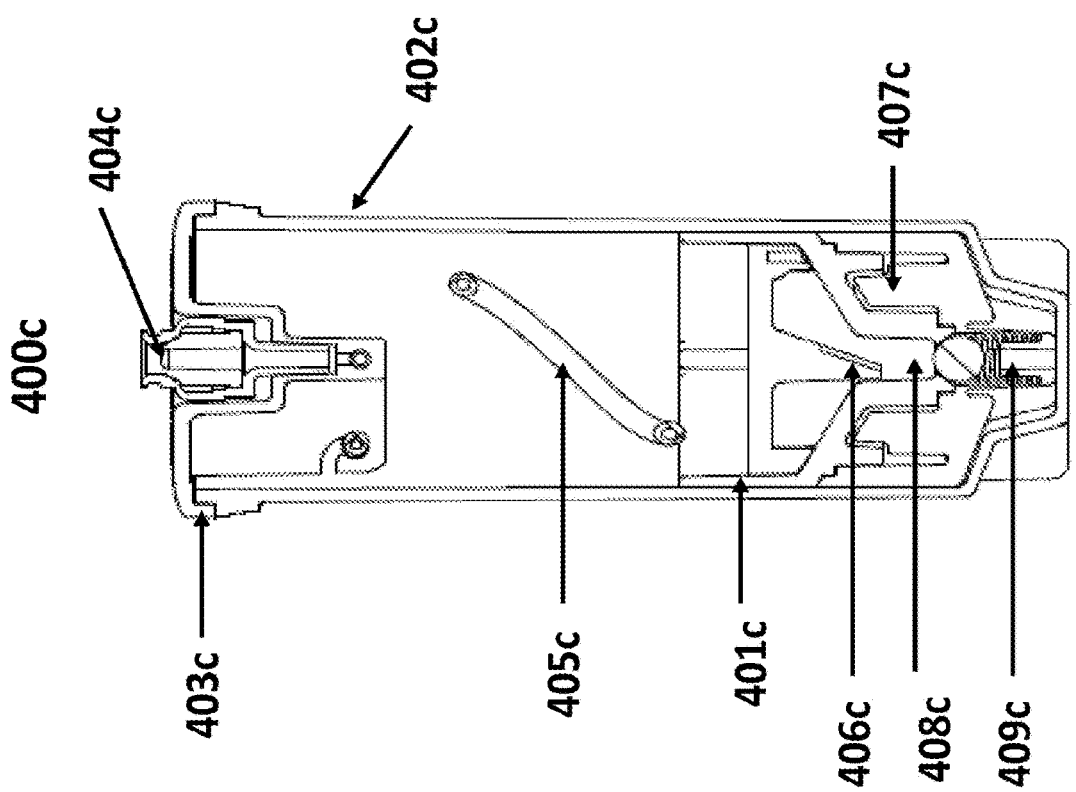
FIG. 4C depicts a side view of a device for separating components of a multi-component liquid according to certain embodiments.

FIGS. 4C and 4D depict two different side views of a device for separating components of a multi-component liquid according to certain embodiments. FIG. 4C illustrates a side view of device 400c before centrifugation where buoy 401c is positioned at the bottom of container 402c. As described in greater detail below, during centrifugation the buoy is displaced along the longitudinal axis of container 402c (upward as depicted in FIG. 4D). Buoy 401c includes one or more sealed chambers 407c having a fluidic composition or containing a vacuum. The proximal end of buoy 401c is in fluid communication with a single port 404c in lid 403c through conduit 405c. To aid in resuspension of components on the buoy (as described below), buoy 401c includes a deflector 406c within the bore in channel 408c that is fluidically sealed by ball and spring valve 409c. FIG. 4D illustrates a side view of device 400d after centrifugation where buoy 401d has been displaced a distance along the longitudinal axis from the bottom of container 402d. Buoy 401d includes one or more sealed chambers 407d having a fluidic composition or containing a vacuum. The proximal end of buoy 401d is in fluid communication with a single port 404d in lid 403d through conduit 405d. As shown above in FIG. 4C, buoy 401d also includes a deflector 406d within the bore in channel 408d to aid in resuspension of components. Buoy 401c also includes a ball and spring valve 409d.

Methods for Separating Components by Centrifugation

As summarized above, aspects of the disclosure also include methods for separating components of a multi-component liquid sample. Methods according to certain embodiments include introducing a multi-component liquid sample (e.g., blood) into a container of one or more of the subject separation devices described above, subjecting the sample to a force of centrifugation to produce two or more fractions in the sample, each fraction having a component from the sample of a different density and collecting one or more components of the sample. The term "separating" is used herein in its conventional sense to refer to the physical separation of a plurality of components based on a particular physical or chemical property such as density of the component. As described in greater detail below, the multi-component liquid sample is subjected to a force of centrifugation for a duration sufficient to fractionate the components of the sample into two or more fractions (e.g., layers), each fraction containing components of different density. In embodiments, components of the sample are separated such that each component has a higher concentration in a particular fraction (e.g., bottom layer, upper layer, middle layer, etc.) as compared to the sample before being subjected to the force of centrifugation. In other words, components of the multi-component liquid sample are fractionated in a manner sufficient to enrich the components into particular layers within the liquid sample.

For example, the concentration of a component in a particular fraction of the sample (e.g., bottom layer, upper layer, middle layer, etc.) may be increased by 5% or more, such as by 10% or more, such as by 20% or more, such as by 25% or more, such as by 30% or more, such as by 50% or more, such as by 75% or more, such as by 90% or more including by 95% or more as compared to the sample before being subjected to the force of centrifugation. In some instances, the concentration of a component in a particular region of the sample may be increased by 2-fold or more, such as by 3-fold or more, such as by 5-fold or more, such as by 7-fold or more and including by 10-fold or more.

In embodiments of the present disclosure, components of the sample may be separated into two or more fractions such that 5% or more of a certain component is separated in a particular fraction (e.g., bottom layer, upper layer, middle layer, etc.) of the sample, such as 10% or more, such as 20% or more, such as 25% or more, such as 30% or more, such as 40% or more, such as 50% or more, such as 60% or more, such as 70% or more, such as 80% or more, such as 90% or more, such as 95% or more and including separating 99% or more of a component into a particular fraction of the sample. In certain embodiments, 100% of the component is separated into a particular fraction of the sample.

In one example, the sample is whole blood or a derivative thereof (e.g., whole blood having one or more anticoagulants) and is subjected to a force of centrifugation for a duration sufficient to separate 90% or more of plasma into a first fraction, 90% or more of the buffy coat into a second fraction and 90% or more of red blood cells into a third fraction. For instance, the whole blood sample or derivative thereof is subjected to a force of centrifugation for a duration sufficient to separate 95% of the plasma into a first fraction, 95% of the buffy coat into a second fraction and 95% of the red blood cells into a third fraction.

In another example, the sample is bone marrow aspirate or a derivative thereof and is subjected to a force of centrifugation for a duration sufficient to separate 90% or more of a first component of the bone marrow aspirate into a first fraction, 90% or more of a second component of the bone marrow aspirate into a second fraction and 90% or more of a third component of the bone marrow aspirate into a third fraction. For instance, the bone marrow aspirate or derivative thereof is subjected to a force of centrifugation for a duration sufficient to separate 95% or more of a first component of the bone marrow aspirate into a first fraction, 95% or more of a second component of the bone marrow aspirate into a second fraction and 95% or more of a third component of the bone marrow aspirate into a third fraction.

As discussed above, the term multi-component liquid sample is used to describe suspended media having more than one component and may include, but is not limited to biological samples. Biological samples may include a whole organism, plant, fungi or a subset of animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may include any type of organismic material, including both healthy and diseased components (e.g., cancerous, malignant, necrotic, etc.). In certain embodiments, the biological sample is a liquid sample, such as whole blood or derivative thereof, bone marrow aspirate, stromal vascular fraction, plasma, tears, sweat, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.). The term "blood sample" refers to whole blood or a subset of blood components, including but not limited to platelets, red blood cells, white cells and blood plasma. In some embodiments, the blood sample is obtained from an in vivo source and can include blood samples obtained from tissues (e.g., cell suspension from a tissue biopsy, cell suspension from a tissue sample, etc.) or directly from a subject. In some cases, blood samples derived from a subject are cultured, stored, or manipulated prior to evaluation.

In certain embodiments the source of the biological sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present disclosure may be applied to samples from a human subject, it is to be understood that the methods may also be carried-out on samples from other animal subjects (that is, in "non-human subjects") such as, but not limited to, birds, mice, rats, dogs, cats, livestock and horses.

In embodiments, the multi-component liquid sample may also be a biological sample (as described above) that includes one or more compounds, such as a preservative, antioxidant, stabilizer, surfactant, anticoagulant, chelating agent and the like. In certain instances, the multi-component liquid sample is whole blood or bone marrow aspirate that includes one or more anticoagulants. For example, the multi-component liquid sample may be whole blood or bone marrow aspirate that contains heparin or a calcium chelating agent (e.g., citrate or EDTA). The concentration of each compound in the biological sample may vary depending on the type and volume of biological sample and may be 0.001 mM or more, such as 0.005 mM or more, such as 0.01 mM or more, such as 0.05 mM or more, such as 0.1 mM or more, such as 0.5 mM or more, such as 1 mM or more, such as 5 mM or more, such as 10 mM or more, such as 100 mM or more, such as 500 mM or more, such as 1000 mM or more and including 5000 mM or more. For example, the concentration of the compounds in the biological sample may range from 0.001 mM to 5000 mM, such as from 0.01 mM to 1000 mM and including from 0.1 mM to 500 mM.

In practicing methods of the present disclosure, a multi-component liquid sample is introduced into a container of one or more of the subject devices (as described above) and subjected to a force of centrifugation for a duration sufficient to fractionate the components of the sample into two or more fractions (e.g., layers) within the sample. (e.g., higher density components forming a layer at the bottom part of the container and lower density components forming a layer at the upper part of the container). One or more components are then collected from the container.

In embodiments, the multi-component liquid sample may be introduced into the container by any convenient liquid dispensing protocol, such as introducing the sample through one or more ports in the cap of the subject devices with a pipette, a syringe with or without a needle, a manual or mechanical dispenser or computer-automated liquid dispensing protocol. Where the container includes a single port (as described above), the multi-component liquid sample is introduced through the single port in the cap of the container. The volume of multi-component sample introduced into the container varies depending on the type of sample, size of device and amount of desired component recovery and ranges from 1 mL to 5000 mL, such as from 5 mL to 4500 mL, such as from 10 mL to 4000 mL, such as from 20 mL to 3500 mL, such as from 30 mL to 3000 mL, such as from 40 mL to 2500 mL, such as from 50 mL to 2000 mL, such as from 75 mL to 1500 mL and including from 100 mL to 1000 mL.

In practicing the subject methods, the sample is subjected to a force of centrifugation one or more times. The term "force of centrifugation" is used herein in its conventional sense to refer to the force applied to the sample through revolving the device about an axis of rotation where the force on the components of the sample is in certain embodiments, given by the relative centrifugal force (RCF). The force of centrifugation may be applied by any convenient protocol, where in some embodiments, the force of centrifugation is applied by centrifuging the device with introduced sample with a centrifuge. In these embodiments, any convenient centrifuge may be employed, such as for example a fixed-angle centrifuge, a swinging bucket centrifuge, ultracentrifuge, solid bowl centrifuges, conical centrifuges, among other types of centrifuges. As described in greater detail below, the applied force of centrifugation (in relative centrifugal force, RCF) may vary depending on the sample type and size and may range from 1 g to 50,000 g, such as from 2 g to 45,000 g, such as from 3 g to 40,000 g, such as from 5 g to 35,000 g, such as from 10 g to 25,000 g, such as from 100 g to 20,000 g, such as from 500 g to 15,000 g and including from 1000 g to 10,000 g.

In some embodiments, the sample is subjected to the centrifugation force immediately after the sample is introduced into the subject separation device container. In other embodiments, the sample is subjected to the centrifugation force a predetermined period of time after introducing the sample into the device container. For example, the sample may be subjected to the centrifugation force 0.01 minutes or more after introducing the sample into the device container, such as after 0.05 minutes or more, such as after 0.1 minutes or more, such as after 0.5 minutes or more, such as after 1 minute or more, such as after 5 minutes or more, such as after 10 minutes or more, such as after 15 minutes or more, such as after 30 minutes or more and including 60 minutes after introducing the sample into the device container.

In certain embodiments, methods include a storage or prefabrication step where the sample is a specimen that has been preloaded into one or more of the subject separation devices and stored for a predetermined period of time before subjecting the sample to the centrifugation force. The amount of time the sample is preloaded and stored may vary, such as 0.1 hours or more, such as 0.5 hours or more, such as 1 hour or more, such as 2 hours or more, such as 4 hours or more, such as 8 hours or more, such as 16 hours or more, such as 24 hours or more, such as 48 hours or more, such as 72 hours or more, such as 96 hours or more, such as 120 hours or more, such as 144 hours or more, such as 168 hours or more and including preloading the sample for 240 hours or more. For example, the amount of time the sample is preloaded and stored may range from 0.1 hours to 240 hours, such as from 0.5 hours to 216 hours, such as from 1 hour to 192 hours and including preloading the sample from 5 hours to 168 hours before subjecting the sample to the centrifugation force. For instance, the sample may be preloaded into one or more of the subject separation devices at a remote location (e.g., as in a physician's office or outpatient clinic) and sent to a laboratory for processing in accordance with the subject methods. By "remote location" is meant a location other than the location at which the sample is obtained and preloaded. For example, a remote location could be another location (e.g., office, lab, etc.) in the same city, another location in a different city, another location in a different state, another location in a different country, etc., relative to the location of the processing device, e.g., as described in greater detail below. In some instances, two locations are remote from one another if they are separated from each other by a distance of 10 m or more, such as 50 m or more, including 100 m or more, e.g., 500 m or more, 1000 m or more, 10,000 m or more, etc.

In embodiments, the sample is subjected to a force of centrifugation for a duration sufficient to separate components of different density into two or more fractions within the sample. The duration the sample is subjected to the force of centrifugation may vary and may be 0.01 minutes or longer, such as for 0.05 minutes or longer, such as for 0.1 minutes or longer, such as for 0.5 minutes or longer, such as for 1 minute or longer, such as for 3 minutes or longer, such as for 5 minutes or longer, such as for 10 minutes or longer, such as for 15 minutes or longer, such as for 20 minutes or longer, such as for 30 minutes or longer, such as for 45 minutes or longer, such as for 60 minutes or longer and including for 90 minutes or longer. For example, the sample may be subjected to force of centrifugation for a duration which ranges from 0.01 minutes to 960 minutes, such as from 0.05 minutes to 480 minutes, such as from 0.1 minutes to 240 minutes, such as from 0.5 minutes to 120 minutes, such as from 1 minute to 90 minutes, such as from 5 minutes to 60 minutes and including from 10 minutes to 45 minutes.

Depending on the volume of sample and density dispersity of the sample components, the rotational speed of centrifugation may vary, such as from $1 \times 10^3$ revolutions per minute (rpm) to $1000 \times 10^3$ rpm, such as from $2 \times 10^3$ rpm to $900 \times 10^3$ rpm, such as from $3 \times 10^3$ rpm to $800 \times 10^3$ rpm, such as from $4 \times 10^3$ rpm to $700 \times 10^3$ rpm, such as from $5 \times 10^3$ rpm to $600 \times 10^3$ rpm, such as from $10 \times 10^3$ rpm to $500 \times 10^3$ rpm and including from $25 \times 10^3$ rpm to $100 \times 10^3$ rpm. The centrifuge may be maintained at a single speed or may be changed to a different speed at any time during separation of the sample components. Where the centrifuge is operated at more than one speed, the duration the centrifuge is maintained at each speed may independently be 0.01 minutes or more, such as 0.1 minutes or more, such as 1 minute or more, such as 5 minutes or more, such as 10 minutes or more, such as 30 minutes or more and including 60 minutes or more. The time period between each different speed employed may also vary, as desired, being separated independently by a delay of 1 minute or more, such as 5 minutes or more, such as by 10 minutes or more, such as by 15 minutes or more, such as by 30 minutes or more and including by 60 minutes or more. In embodiments where the centrifuge is maintained at more than two (i.e., three or more) speeds to subject the sample to the centrifugation force, the delay between each speed employed may be the same or different.

Depending on the type and number of components of different density in the sample, the centrifuge may be maintained at a speed to subject the sample to the centrifugation force continuously or in discrete intervals. For example, in some embodiments, the centrifuge is maintained at a speed to subject the sample to a centrifugation force continuously. In other instances, the centrifuge is maintained at a speed to subject the sample to a centrifugation force in discrete intervals, such as for example for intervals of for 0.01 minutes or longer, such as for 0.05 minutes or longer, such as for 0.1 minutes or longer, such as for 0.5 minutes or longer, such as for 1 minute or longer, such as for 3 minutes or longer, such as for 5 minutes or longer, such as for 10 minutes or longer, such as for 15 minutes or longer, such as for 20 minutes or longer, such as for 30 minutes or longer, such as for 45 minutes or longer, such as for 60 minutes or longer and including for 90 minutes or longer. Where the centrifuge is maintained at a speed in discrete intervals, methods may include 1 or more intervals, such as 2 or more intervals, such as 3 or more intervals and including 5 or more intervals.

The sample may be subjected to the force of centrifugation one or more times. In certain embodiments, methods include subjecting the sample to a force of centrifugation only one time. In other words, methods according to this embodiment are characterized by a single application of the centrifugation force to the sample, such as by centrifuging the subject device with introduced sample for a single spin interval. In other embodiments, methods include subjecting the sample to a force of centrifugation 2 more times, such as 3 or more times, such as 4 or more times and including 5 or more times. Where the sample is subjected to a force of centrifugation 2 or more times, the centrifugation force (e.g., the speed of the centrifuge) and the duration may be the same or different. In some embodiments, each time the sample is subjected to a force of centrifugation, the centrifugation force and the duration is the same. In other embodiments, the centrifugation force and the duration is different each time the sample is subjected to a force of centrifugation. In yet other embodiments, the centrifugation force remains the same, but duration is different. In still other embodiments, the centrifugation force is different but duration remains the same.

In certain embodiments, methods include subjecting the sample to a force of centrifugation in a two-step method where the sample is subjected to a first force of centrifugation when the centrifuge activated valve is in the open position and subjecting to a second force of centrifugation when the centrifuge activated valve is in the closed position. The rotational speed of centrifugation during each step may vary, as described above, such as where the speed of centrifugation when the centrifuge activated valve is in the open position ranges from $1 \times 10^3$ revolutions per minute (rpm) to $1000 \times 10^3$ rpm (e.g., from $2 \times 10^3$ rpm to $500 \times 10^3$ rpm) and the speed of centrifugation when the centrifuge activated valve is in the closed position ranges from $1 \times 10^3$ revolutions per minute (rpm) to $1000 \times 10^3$ rpm (e.g., from $2 \times 10^3$ rpm to $500 \times 10^3$ rpm).

The duration of centrifugation may also vary during each step, such as subjecting the sample to a force of centrifugation when the centrifuge activated valve is in the open position for a duration ranging from 0.1 minutes to 60 minutes (such as from 1 minute to 15 minutes) and subjecting the sample to a force of centrifugation when the centrifuge activated valve is in the closed position for a duration ranging from 0.1 minutes to 60 minutes (such as from 0.5 minutes to 30 minutes).

In embodiments of the present disclosure, each step (introduction of the sample into the separation device container, subjecting the sample to a centrifugation force one or more times and collecting one or more of the separated fractions of the sample) can be carried out at any suitable temperature so long as the viability of the components (e.g., red blood cells, white blood cells, platelets, etc.) of the sample are preserved as desired. As such, the temperature according to embodiments of the disclosure may vary, such as from $-80°$ C. to $100°$ C., such as from $-75°$ C. to $75°$ C., such as from $-50°$ C. to $50°$ C., such as from $-25°$ C. to $25°$ C., such as from $-10°$ C. to $10°$ C., and including from $0°$ C. to $25°$ C.

Where necessary, the parameters for subjecting the samples to a centrifugation force may be changed at any time during methods of the present disclosure. For example, the speed of the centrifuge, the duration the sample is subjected to the centrifugation force and heating or cooling of the sample may be changed one or more times during the subject methods, such as two or more times, such as three or more times and including five or more times.

In some embodiments, methods include changing the speed of the centrifuge, such as by increasing or decreasing the speed by 1% or more, such as by 5% or more, such as by 10% or more, such as by 25% or more, such as by 50% or more, such as by 75% or more, such as by 90% or more, such as by 2-fold or more, such as by 5-fold or more, such as by 10-fold or more and including by 25-fold or more. For example, the speed of the centrifuge may be increased or decreased by $0.5 \times 10^3$ rpm or more, such as by $1 \times 10^3$ rpm or more, such as by $2 \times 10^3$ rpm or more, such as by $5 \times 10^3$ rpm or more, such as by $10 \times 10^3$ rpm or more, such as by $25 \times 10^3$ rpm or more and including increasing or decreasing the speed of the centrifuge by $100 \times 10^3$ rpm or more.

In other embodiments, the duration the sample is subjected to the centrifugation force may be changed. For example, the duration the sample is subjected to the centrifugation force may be increased or decreased by 0.01 minutes or longer, such as by 0.05 minutes or longer, such as by 0.1 minutes or longer, such as by 0.5 minutes or longer, such as by 1 minute or longer, such as by 3 minutes or longer, such as by 5 minutes or longer, such as by 10 minutes or longer, such as by 15 minutes or longer, such as by 20 minutes or longer, such as by 30 minutes or longer, such as by 45 minutes or longer, such as by 60 minutes or longer and including by 90 minutes or longer.

In yet other embodiments, the temperature while subjecting the sample to the centrifugation force may be changed. For example, the temperature may be raised or lower by $0.1°$ C. or more, such as by $0.5°$ C. or more, such as by $1°$ C. or more, such as by $2°$ C. or more, such as by $5°$ C. or more and including raising or lowering the temperature by $8°$ C. or more.

In certain embodiments, methods include monitoring the centrifuged sample. Monitoring may include assessing (either by a human or with the assistance of a computer, if using a computer-automated process initially set up under human direction) the extent of component separation within the sample. For example, monitoring separation of components by density into the two or more fractions within the sample may include visually determining fraction boundaries between components of the sample. Monitoring separation of components may also include assessing the physical and chemical properties of the components in each fraction within the sample. Any convenient protocol can be employed to monitor the sample, including but not limited to visual observation, laser scatter, fluorescence, phosphorescence, chemiluminescence, diffuse reflectance, infrared spectroscopy, among other sensing protocols.

In some instances, monitoring includes collecting real-time data, such as employing a detector (e.g., with a video camera). In other instances, monitoring includes assessing the sample at regular intervals, such as every 0.01 minutes, every 0.05 minutes, every 0.1 minutes, every 0.5 minutes, every 1 minute, every 5 minutes, every 10 minutes, every 30 minutes, every 60 minutes or some other interval.

Methods of the present disclosure may also include a step of assessing the sample to identify any desired adjustments to the subject protocol. In other words, methods in these embodiments include providing feedback based on monitoring the sample, where adjustments to the protocol may vary in terms of goal, where in some instances the desired adjustment or adjustments that ultimately result in an improved fractionation of components by density within the sample, such as providing faster separation, improved purity or increased component enrichment of the components into the two or more fractions within the sample.

Where feedback provided indicates that a particular protocol is less than optimal, such as where component separation requires too much time or where component separation provides separated fractions with insufficient enrichment (e.g., components of different density are undesirably mixed), methods may include changing one or more parts of the subject protocols. For example, one or more parameters for subjecting the sample to a centrifugation force may be adjusted. In one example, methods include adjusting the speed of the centrifuge (as described above). In another example, methods include changing (increasing or decreasing) the duration the sample is subjected to the centrifugation force. In yet another example, methods include heating or cooling the sample.

As discussed above, in certain embodiments the buoy in the subject devices includes a centrifuge activated valve (e.g., ball and spring valve) that is configured to open and close in response to the force of centrifugation. For instance, the centrifuge activated valve may be configured to open in response to a force of centrifugation ranging from 1 g to 50,000 g, such as from 2 g to 45,000 g, such as from 3 g to 40,000 g, such as from 5 g to 35,000 g, such as from 10 g to 25,000 g, such as from 100 g to 20,000 g, such as from 500 g to 15,000 g and including from 1000 g to 10,000 g. In these embodiments, centrifuging the device is sufficient to open the centrifuge activated valve and collect one or more components of the sample on the surface of the buoy, such as on the proximal end of the buoy, such as at the base of the concave outer surface of the buoy, such as adjacent to an orifice on the buoy, such as in a channel in the buoy, such as on the surface of a centrifuge activated suspension floor of the centrifuge activated valve, such as on the surface of the ball in a ball and spring valve. Accordingly, methods according to certain embodiments of the present disclosure include subjecting the separation device to a force of centrifugation sufficient to open the centrifuge activated valve and collect one or more components onto the surface of centrifuge activated check valve. For instance, in one example where the multi-component liquid sample is blood, subjecting the sample in the container of the subject devices to a force of centrifugation is sufficient to open the centrifuge activated valve and collect buffy coat on the surface of the buoy, such as on the proximal end of the buoy, such as at the base of the concave outer surface of the buoy, such as adjacent to an orifice on the buoy, such as in a channel in the buoy, such as on the surface of the centrifuge activated valve, such as on the surface of the ball in a ball and spring valve.

In certain embodiments, the buoy in the subject devices displaces along the longitudinal axis within the container in response to the force of centrifugation. For example, the buoy may displace proximally or distally during centrifugation. In some embodiments, the buoy is displaced along 25% or more of the length of the container, such as 35% or more, such as 50% or more, such as 60% or more, such as 75% or more, such as 90% or more, such as 95% or more, such as 97% or more and including 99% or more of the length of the container. In some instances, the buoy is positioned at the distal portion of the container and is displaced proximally along the longitudinal axis of the container in response to centrifugation. In certain instances, the buoy displaces during centrifugation to a particular location in the fractionated sample. In one example, the buoy displaces in response to centrifugation to a position at the interface between two fractionated components. In another example, the buoy displaces in response to centrifugation to a position within a predetermined fraction, such as within a bottommost fraction, such as within an uppermost fraction or within some fraction in between. In yet another example, the buoy displaces in response to centrifugation to a position at the bottom of the container. In still another example, the buoy displaces in response to centrifugation to a position at the top of the container. In certain embodiments, the sample is whole blood and methods include centrifuging the device with introduced sample for a duration sufficient to displace the buoy from the bottom of the container to a position at the interface between red blood cells and plasma. In certain embodiments, the sample is bone marrow aspirate and methods include centrifuging the device with introduced sample for a duration sufficient to displace the buoy from the bottom of the container to a position at the interface between red blood cells and plasma so as to concentrate stem cells (e.g., hematopoietic stem cells, mesenchymal stem cells, etc.). In certain embodiments, the sample is bone marrow aspirate and peripheral whole blood combined and methods include centrifuging the device with introduced sample for a duration sufficient to displace the buoy from the bottom of the container to a position at the interface between red blood cells and plasma so as to concentrate stem cells (e.g., hematopoietic stem cells, mesenchymal stem cells, etc.). In certain embodiments, the sample is stromal vascular fraction derived from adipose tissue and peripheral whole blood and centrifuging the device with introduced sample for a duration sufficient to displace the buoy from the bottom of the container to a position at the interface between red blood cells and plasma so as to concentrate stem cells (e.g., mesenchymal cells) and endothelial cells from adipose together with the platelets and monocytes derived from peripheral whole blood while depleting excess plasma and red blood cells.

In practicing the subject methods, one or more of the separated fractions may be collected. In some embodiments, all of the separated fractions are collected. Fractions may be collected using any suitable collecting protocol, such as aspirating using a syringe with or without a needle, a manual or mechanically operated serological pipette as well as with an automated liquid collection system (e.g., a computer-controlled collection apparatus). Where the sample is portioned into two or more of the subject devices, collecting fractions may include combining fractions of similar makeup. For example, where a whole blood or bone marrow aspirate sample is fractionated using two or more of the subject devices, buffy coat from each of the devices may be collected (e.g., from the surface of a centrifuge activated suspension floor of the centrifuge activated valve on the buoy) and combined.

Separated fractions may be collected from the sample at any time after subjecting the sample to the force of centrifugation. In some embodiments, the separated fractions are collected 1 minute or greater after the separated fractions are prepared, such as 2 minutes or greater, such as 3 minutes or greater, such as 5 minutes or greater, such as 10 minutes or greater and including 30 minutes or greater after the separated fractions are prepared.

In some embodiments, collecting one or more fractions from the sample includes removing a portion of a first fraction from the sample, mixing the remaining portion of the first fraction with a second fraction within the buoy to produce a mixture of the first fraction and the second fraction and removing the mixture of the first fraction and second fraction from the container. In embodiments, removing a portion of the first fraction may include removal of 10% or more of the first fraction, such as 15% or more, such as 25% or more, such as 50% or more, such as 75% or more and including removing 90% or more of the first fraction. Put another way, methods according to these embodiments include retaining 90% or less of the first fraction, such as 85% or less, such as 75% or less, such as 50% or less, such as 25% or less and including retaining 10% or less of the first fraction. For example, where the first fraction has a volume of 100 mL, methods may include removing 10 mL or more of the first fraction, such as 15 mL or more, such as 25 mL or more, such as 50 mL or more, such as 75 mL or more and including removing 90 mL or more of the first fraction. In certain instances, the sample is whole blood and methods include removing 10% or more of the platelet poor plasma, such as 15% or more, such as 25% or more, such as 50% or more, such as 75% or more and including removing 90% or more of the platelet poor plasma.

In certain embodiments, methods for removing a portion of the first fraction include positioning a liquid collection device (e.g., needle with syringe) a predetermined depth into the first fraction. For example, the liquid collection device may be positioned 1 mm or more into the first fraction, such as 2 mm or more, such as 3 mm or more, such as 5 mm or more, such as 10 mm or more and including 25 mm or more into the first fraction. In certain embodiments, the liquid collection device is positioned to a depth as determined by one or more reference indicators on the container. In still other embodiments, the liquid collection device is positioned to a depth relative to the outer edge of the buoy proximal end, such as 1 mm or more above the outer edge of the buoy proximal end, such as 2 mm or more, such as 3 mm or more, such as 5 mm or more, such as 10 mm or more and including 25 mm or more above the outer edge of the buoy proximal end. In certain instances, methods for removing a portion of the first fraction include positioning the liquid collection device directly against the outer edge of the buoy proximal end.

In these embodiments, a second fraction is mixed with the remaining portion of the first fraction in the buoy. In one example, the remaining portion of the first fraction and the second fraction are mixed on the concave outer surface of the proximal end of the buoy. In another example, the remaining portion of the first fraction and the second fraction are mixed on the surface of the centrifuge activated valve at the base of the concave outer surface of the buoy proximal end. In yet another example, where the buoy includes a channel above the centrifuge activated valve (extending between a first orifice and second orifice, as described above), the remaining portion of the first fraction and the second fraction may be mixed within the channel in the buoy. In certain instances, the sample is whole blood and methods include mixing the remaining portion of platelet poor plasma with buffy coat which collects on the surface of the buoy (such as in the channel when present or at the base of the concave outer surface of the buoy proximal end when a channel is not present in the buoy) and producing platelet rich plasma.

The remaining portion of the first fraction and the second fraction may be mixed in the buoy by any convenient protocol, such as for example agitation or stirring the two together. In certain embodiments, mixing the remaining portion of the first fraction with the second fraction includes aspirating the remaining portion of the first fraction into syringe and reinjecting the first fraction into the buoy to mix the first fraction with the second fraction within the buoy. In other embodiments mixing includes aspirating the remaining portion of the first fraction and the second fraction into a syringe and reinjecting both the first fraction and second fraction into the buoy. In yet other embodiments, methods include aspirating the remaining portion of the first fraction and the second fraction into a syringe, agitating the first fraction and second fraction in the syringe and reinjecting the mixture into the buoy. Mixing the remaining portion of the first fraction with the second fraction may be repeated as desired, such as 2 or more times, such as 3 or more times, such as 4 or more times, such as 5 or more times and including 10 or more times. After the remaining portion of first fraction and the second fraction are sufficiently mixed as desired (e.g., adequately mixed platelet rich plasma is produced), the mixture may be collected by any convenient liquid collection protocol, such as with a syringe with or without a needle, a manual or mechanically operated sero- logical pipette as well as with an automated liquid collection system (e.g., a computer-controlled collection apparatus).

Figure 5A:
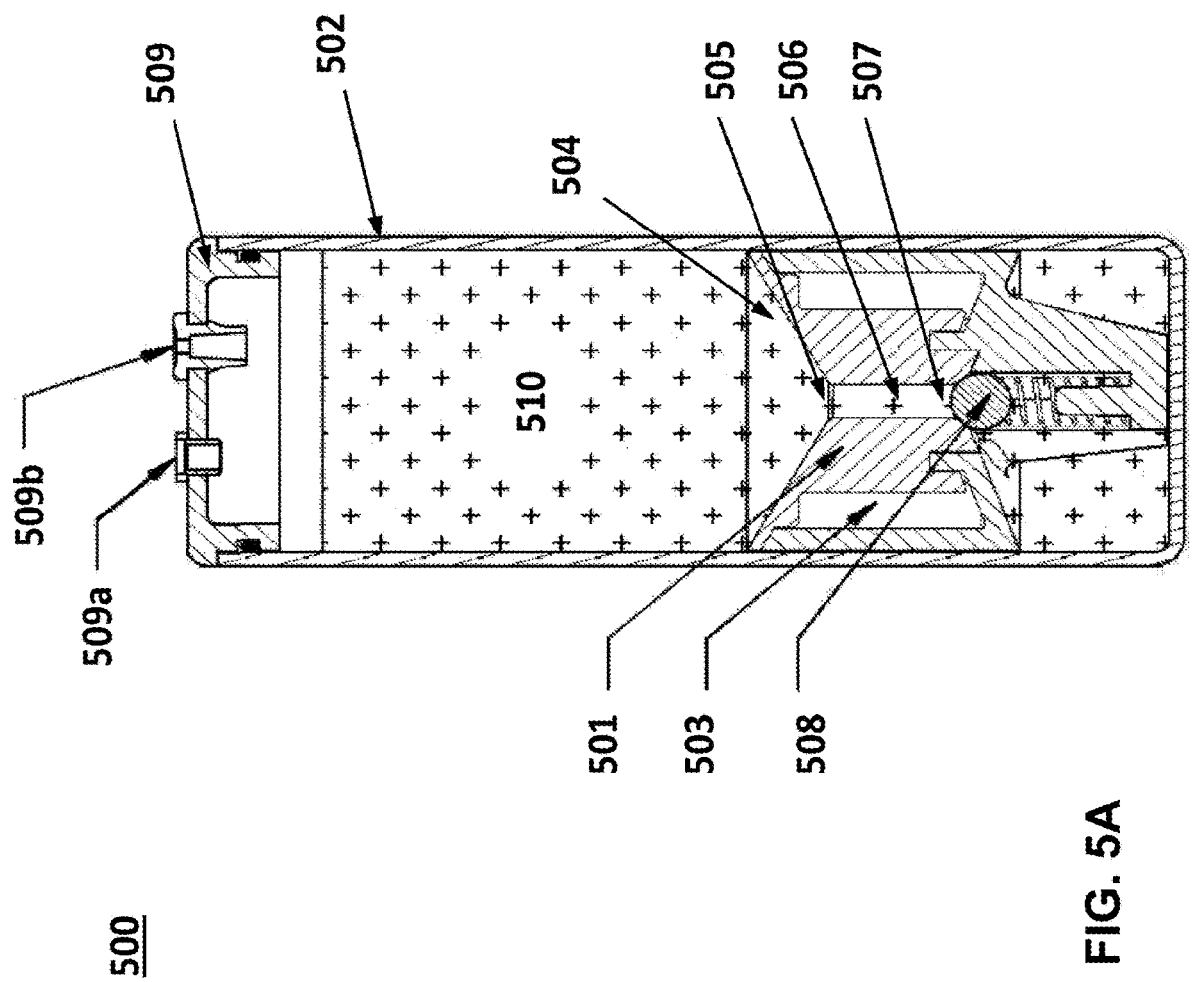
FIG. 5A illustrates a first step of a step-by-step method of FIGS. 5A-5F for separating components of a multi-component liquid sample (e.g., blood or bone marrow aspirate) according to certain embodiments. A separation device having multi-component sample in the container before applying a force of centrifugation is depicted.

FIGS. 5A-5F illustrate step-by-step methods for separating components of a multi-component liquid sample (e.g., whole blood) according to certain embodiments. FIG. 5A depicts device 500 having a buoy 501 positioned inside of container 502. Buoy 501 includes one or more sealed chambers 503 containing a fluidic composition or a vacuum and concave outer surface 504 at the proximal end. At the base of the concave outer surface of the buoy proximal end is a first orifice 505 in fluid communication with channel 506 and second orifice 507. Second orifice 507 is sealed by ball-and-spring check valve 508 in the closed position. Device 500 also includes a cap 509 positioned at the proximal end of the container. Multi-component liquid sample 510 (e.g., blood) is introduced into the container with a syringe or other suitable dispensing protocol through port 509b in the cap with gas vent 509a in an open or closed position.

Figure 5B:
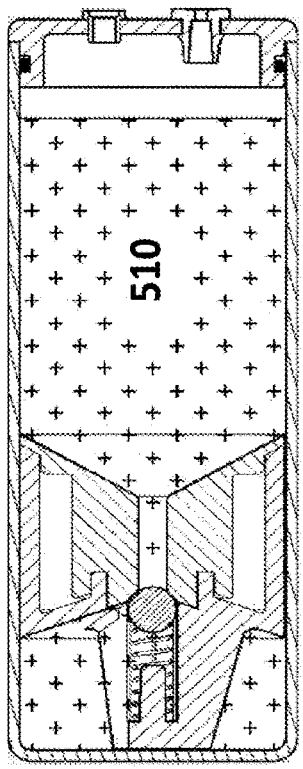
FIG. 5B illustrates a second step of a step-by-step method of FIGS. 5A-5F for separating components of a multi-component liquid sample (e.g., blood or bone marrow aspirate) according to certain embodiments. The subject device is depicted with introduced sample at the beginning of centrifugation where the ball and spring valve in the buoy is in a closed position.
Figure 5C:
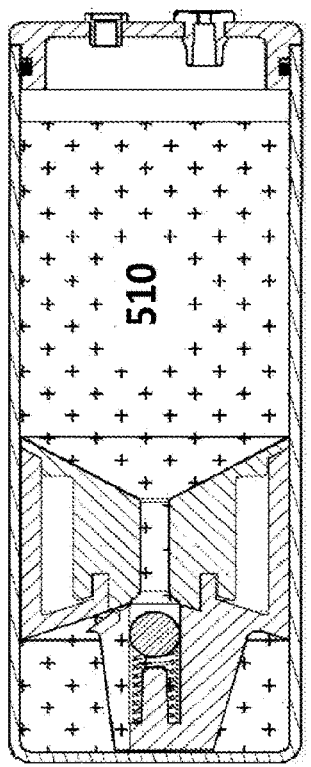
FIG. 5C illustrates a third step of a step-by-step method for separating components of a multi-component liquid sample (e.g., blood or bone marrow aspirate) according to certain embodiments. The device is depicted with the ball and spring valve in the open position during centrifugation due to the force of the ball compressing the spring.
Figure 5D:
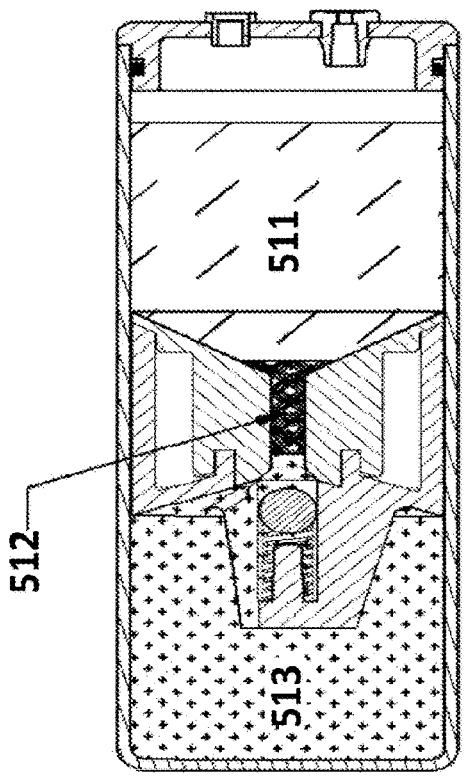
FIG. 5D illustrates a fourth step of a step-by-step method for separating components of a multi-component liquid sample (e.g., blood or bone marrow aspirate) according to certain embodiments. The device is depicted with the components of the sample separated at different positions in the device.

The beginning of centrifugation of the subject device with introduced sample is shown in FIG. 5B where the ball and spring valve closes the second orifice. After centrifugation for a sufficient duration and to a desired relative centrifugal force (as described above), the ball and spring valve proceeds to an open position as shown in FIG. 5C, such that there is fluid communication through second orifice 507. After sufficient duration, the sample is separated into fractions, such as into a first fraction 511, a second fraction 512 and a third fraction 513. For example, where the sample is blood, first fraction 511 may be platelet poor plasma, second fraction 512 may be buffy coat, and third fraction 513 may be red blood cells. As shown here, second fraction 512 (e.g., buffy coat) collects within channel 506 in response to the opening of valve 508 during centrifugation.

Figure 5E:
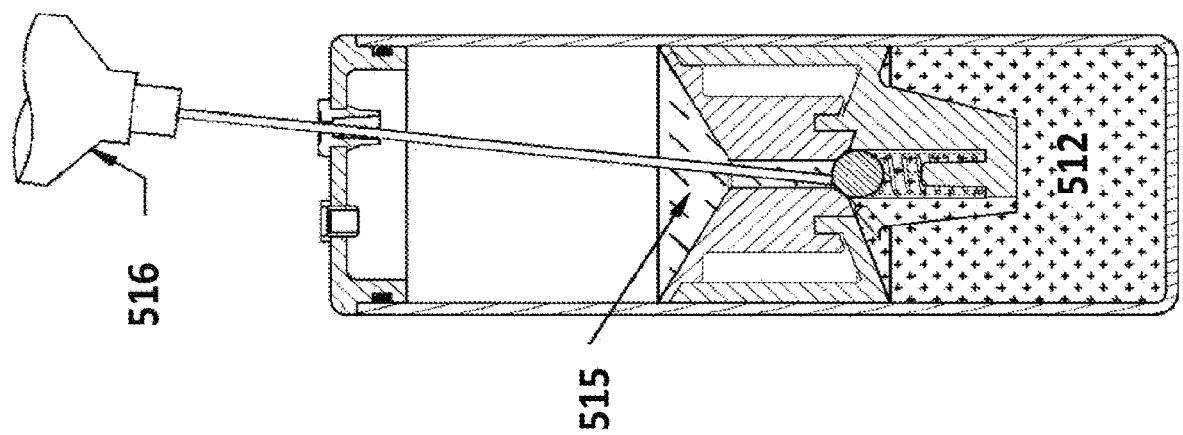
FIG. 5E illustrates a step-by-step method for separating components of a multi-component liquid sample (e.g., blood or bone marrow aspirate) according to certain embodiments. The device is depicted after collection of separated components of the sample according to certain embodiments.
Figure 5F:
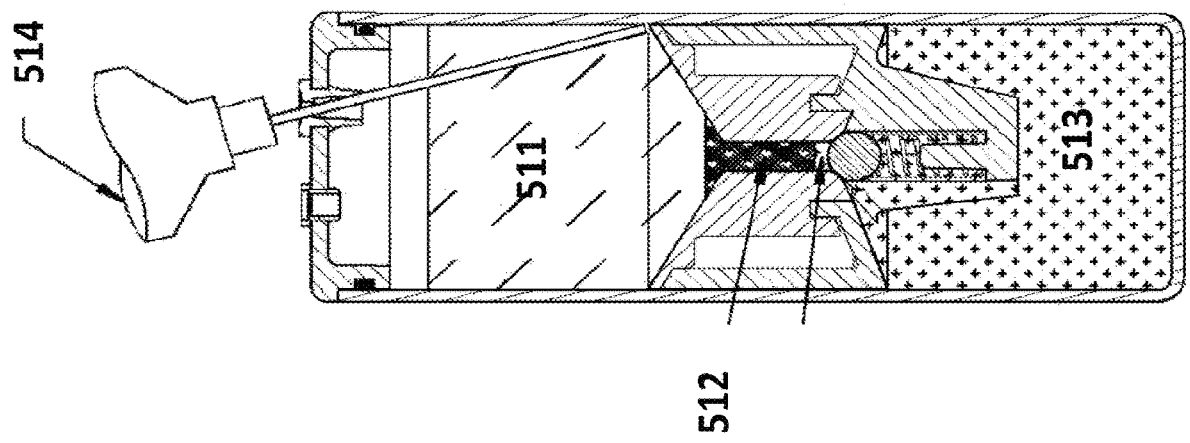
FIG. 5F illustrates step-by-step methods for separating components of a multi-component liquid sample (e.g., blood or bone marrow aspirate) according to certain embodiments. The device is depicted after collection of separated components of the sample according to certain embodiments.

After centrifugation is complete, the desired components of the sample may be collected. As shown in FIG. 5E, aspirating syringe 514 is inserted into the sample through port 509b to a position at the outer edge of the buoy proximal end. A predetermined amount of fraction 511 (e.g., platelet poor plasma) is removed. In this embodiment, the remaining portion of first fraction 511 is about the volume of the concave outer surface of the buoy proximal end. The remaining portion of first fraction 511 is aspirated into a second syringe 516 and reinjected back into channel 506 to mix second fraction 512 (e.g., buffy coat) with the remaining portion of first fraction 511 in the channel of the buoy. As shown in FIG. 5F, composition 515 (e.g., platelet rich plasma) which is a mixture of first fraction 511 and second fraction 512 is then removed from the container.

As described above, in some embodiments the subject devices include a cap positioned at the proximal end of the container and a conduit that connects one or more ports from the cap to the proximal end of the buoy. In some embodiments, collecting one or more components of the sample may include the steps of: 1) positioning the container at a first angle (e.g., 20 degrees or more) with respect to an axis orthogonal to the ground; 2) removing a portion of the first fraction of the sample through the conduit; 3) rotating the container by a second angle (e.g., 180 degrees) along the longitudinal axis of the container; 4) aspirating the remaining portion of the first fraction through the conduit; 5) mixing the remaining portion of the first fraction with a second fraction within the buoy to produce a mixture of the first fraction and second fraction; and 6) removing the mixture of the first fraction and the second fraction from the container through the conduit. In other embodiments, collecting one or more components of the sample may include the steps of: 1) positioning the container at a first angular position with respect to an axis orthogonal to the ground; 2) removing a portion of the first fraction of the sample through the conduit; 3) tilting the device to a second angular position with respect to the axis orthogonal to the ground; 4) aspirating the remaining portion of the first fraction through the conduit; 5) mixing the remaining portion of the first fraction with a second fraction within the buoy to produce a mixture of the first fraction and second fraction; and 6) removing the mixture of the first fraction and the second fraction from the container through the conduit.

In these embodiments, removing a portion of the first fraction through the conduit includes removal of 10% or more of the first fraction, such as 15% or more, such as 25% or more, such as 50% or more, such as 75% or more and including removing 90% or more of the first fraction. As such, the container may be positioned at an angle that is sufficient to allow for removal of the desired amount of the first fraction through the conduit, such as at an angle of 20 degrees or more relative to an axis orthogonal to the ground, such as 25 degrees or more, such as 30 degrees or more, such as 35 degrees or more, such as 45 degrees or more and including positioning the container at an angle that is 60 degrees or more relative to an axis orthogonal to the ground. For example, where the sample is whole blood, methods may include removing 10% or more of the platelet poor plasma through the conduit by positioning the container at an angle of 20 degrees or more relative to an axis orthogonal to the ground, such as 15% or more, such as 25% or more, such as 50% or more, such as 75% or more and including removing 90% or more of the platelet poor plasma.

The container may be positioned at the desired angle using any suitable protocol, including but not limited to a manual support (e.g., stand) or with a manual, mechanical or automated actuator. In some embodiments, the container may be coupled to a platform with a hinge or latch at a proximal edge of the container where the actuator positions the support at an angle by raising the distal edge of the container. In other embodiments, the actuator may be a lift column that is coupled to the bottom of the container and positioning of the container by the actuator at an angle includes adjusting a pivot or rocker. In some instances, actuation of the container to the desired angle is carried out manually (i.e., positioning of the container by hand). In other instances, the actuator is a mechanical actuation device, such as for example a mechanical lead screw assembly or a mechanically operated geared translation device. In yet other embodiments, the actuator is a motor-driven displacement device, such as a motor actuated displacement stage, motor driven leadscrew assembly, motor-operated geared actuation device employing a stepper motor, servo motor, brushless electric motor, brushed DC motor, microstep drive motor, high resolution stepper motor, among other types of motors.

In some embodiments, after removing a portion of the first fraction through the conduit, the container is rotated along the longitudinal axis of the container (e.g., by 180 degrees) and the remaining portion of the first fraction is aspirated through the conduit and mixed with second fraction in the buoy. In one example, the remaining portion of the first fraction and the second fraction are mixed on the concave outer surface of the proximal end of the buoy. In another example, the remaining portion of the first fraction and the second fraction are mixed on the surface of the centrifuge activated valve at the base of the concave outer surface of the buoy proximal end. In yet another example, where the buoy includes a channel above the centrifuge activated valve (extending between a first orifice and second orifice, as described above), the remaining portion of the first fraction and the second fraction may be mixed within the channel in the buoy. In certain instances, the sample is whole blood and methods include mixing the remaining portion of platelet poor plasma with buffy coat which collects on the surface of the buoy (such as in the channel when present or at the base of the concave outer surface of the buoy proximal end when a channel is not present in the buoy) and producing platelet rich plasma.

In other embodiments, after removing a portion of the first fraction, the container is tilted to a second angular position with respect to the axis orthogonal to the ground and the remaining portion of the first fraction of the biological sample is aspirated through the conduit and mixed with the second fraction in the buoy. The device may be tilted to any suitable angular position, depending on the position of the port in the cap of the container and the volume of the biological sample and may be 5° or more with respect to an axis orthogonal to the ground, such as 10° or more, such as 15° or more, such as 25° or more, such as 30° or more, such as 45° or more, such as 60° or more, such as 75° or more and including 80° or more. For example, the device may be tilted to a second angular position that ranges from 1° to 90° with respect to an axis orthogonal to the ground, such as from 5° to 85°, such as from 10° to 80°, such as from 15° to 75°, such as from 20° to 70° and including from 3° to 60°. In other embodiments, the device is tilted to a second angular position that is 5° or more with respect to the first angular position, such as 10° or more, such as 15° or more, such as 25° or more, such as 30° or more, such as 45° or more, such as 60° or more, such as 75° or more and including 80° or more. For example, the device may be tilted to a second angular position that 1° to 90° with respect to the first angular position, such as from 5° to 85°, such as from 10° to 80°, such as from 15° to 75°, such as from 20° to 70° and including from 3° to 60°.

Mixing the remaining portion of the first fraction with the second fraction may be repeated as desired, such as 2 or more times, such as 3 or more times, such as 4 or more times, such as 5 or more times and including 10 or more times. After the remaining portion of first fraction and the second fraction are sufficiently mixed as desired (e.g., adequately mixed platelet rich plasma is produced), the mixture may be collected by any convenient liquid collection protocol, such as with a syringe with or without a needle, a manual or mechanically operated serological pipette as well as with an automated liquid collection system (e.g., a computer-controlled collection apparatus).

In certain embodiments, the cap positioned at the proximal end of the container includes a single port and the single port is connected to a conduit that fluidically couples the single port in the cap to the proximal end of the buoy. In these embodiments, collecting one or more components of a separated multicomponent sample after centrifugation includes the steps of: 1) positioning the container at a first angle with respect to an axis orthogonal to the ground; 2) removing a portion of the first fraction of the separated multicomponent sample through the conduit; 3) rotating the container by a second angle along the longitudinal axis of the container; 4) aspirating the remaining portion of the first fraction through the conduit; 5) mixing the remaining portion of the first fraction with a second fraction within the buoy to produce a mixture of the first fraction and second fraction and 6) removing the mixture of the first fraction and the second fraction from the container through the conduit.

In these embodiments, removing a portion of the first fraction through the conduit includes removal of 10% or more of the first fraction, such as 15% or more, such as 25% or more, such as 50% or more, such as 75% or more and including removing 90% or more of the first fraction. Depending on the position of the single port in the cap of the container, the container is positioned at a first angle that is sufficient to allow for removal of the desired amount of the first fraction through the single port, such as at an angle that ranges from 10 degrees to 60 degrees relative to an axis orthogonal to the ground, such as from 15 degrees to 55 degrees, such as from 20 degrees to 50 degrees, such as from 25 degrees to 45 degrees and including positioning the container at an angle which ranges from 30 degrees to 40 degrees relative to an axis orthogonal to the ground.

In some embodiments, positioning the container at the first angle includes placing the container into an adjustable titter stand and adjusting the container to the desired angle (e.g., an angle ranging from 10 degrees to 60 degrees relative to an axis orthogonal to the ground). For example, the container may be placed into the adjustable tilter stand and the container may be adjusted to the desired angle while visually monitoring the position of the conduit opening with respect to the first fraction.

A portion of the first fraction of the separated multicomponent sample is removed through the single port at the first angle. For example, 10% or more of the first fraction may be removed at the first angle, such as 15% or more, such as 25% or more, such as 50% or more, such as 75% or more and including removing 90% or more of the first fraction through the single port at the first angle. For example, where the sample is whole blood, methods may include removing 10% or more of the platelet poor plasma through the single port at the first angle, such as 15% or more, such as 25% or more, such as 50% or more, such as 75% or more and including removing 90% or more of the platelet poor plasma.

In some embodiments, after removing a portion of the first fraction through the single port, the container is rotated by a second angle along the longitudinal axis of the container and a second portion of the first fraction is aspirated through the single port. The second angle may vary depending on the amount of the first fraction that remains in the container and the position of the single port on the cap of the container and may range from 90 degrees to 180 degrees, such as from 100 degrees to 170 degrees, such as from 110 degrees to 160 degrees, such as from 120 degrees to 150 degrees and including from 130 degrees to 140 degrees. In certain instances, the container is rotated 180 degrees along the longitudinal axis of the container and the second portion of the first fraction is aspirated through the single port.

In other embodiments, after removing a portion of the first fraction through the single port, the container is tilted to a second angular position with respect to the axis orthogonal to the ground and the remaining portion of the first fraction of the biological sample is aspirated through the single port. As discussed above, the container may be tilted to any suitable angular position, depending on the position of the port in the cap of the container and the volume of the biological sample and may be 5° or more with respect to an axis orthogonal to the ground, such as 10° or more, such as 15° or more, such as 25° or more, such as 30° or more, such as 45° or more, such as 60° or more, such as 75° or more and including 80° or more. For example, the device may be tilted to a second angular position that ranges from 1° to 90° with respect to an axis orthogonal to the ground, such as from 5° to 85°, such as from 10° to 80°, such as from 15° to 75°, such as from 20° to 70° and including from 3° to 60°. In other embodiments, the device is tilted to a second angular position that is 5° or more with respect to the first angular position, such as 10° or more, such as 15° or more, such as 25° or more, such as 30° or more, such as 45° or more, such as 60° or more, such as 75° or more and including 80° or more. For example, the device may be tilted to a second angular position that ranges from 1° to 90° with respect to the first angular position, such as from 5° to 85°, such as from 10° to 80°, such as from 15° to 75°, such as from 20° to 70° and including from 3° to 60°.

Any suitable protocol may be used to position the container at the first and second angles, including but not limited to a manual support (e.g., stand) or with a manual, mechanical or automated actuator. In certain embodiments, the container is positioned at the first and second angles using a tilter stand which positions the container at one or more fixed angles (e.g., 20 degrees relative to an axis orthogonal to the ground) or may be an adjustable tilter stand where the user can adjust the first and second angles as desired. In some instances, collection of each portion of the first fraction as described above is carried out by maintaining the container at the first and second angle by hand.

The second portion of the first fraction is mixed with a second fraction of the multicomponent sample at the buoy surface. For example, the second portion of the first fraction and the second fraction are mixed on the concave outer surface of the proximal end of the buoy. In another example, the second portion of the first fraction and the second fraction are mixed on the surface of the centrifuge activated valve at the base of the concave outer surface of the buoy proximal end. In yet another example, where the buoy includes a channel above the centrifuge activated valve (extending between a first orifice and second orifice, as described above), the second portion of the first fraction and the second fraction may be mixed within the channel in the buoy. In certain instances, the sample is whole blood and the second portion of the first fraction is platelet poor plasma and the second fraction is buffy coat that collects on the surface of the buoy (such as in the channel when present or at the base of the concave outer surface of the buoy proximal end when a channel is not present in the buoy). In these embodiments, methods include aspirating the second portion of the platelet poor plasma at the second angle through the single port in the container cap and reintroducing the second portion of the platelet poor plasma into the container to mix with the buffy coat and produce platelet rich plasma at the buoy.

FIGS. 6A-B illustrate an example of methods for separating components of a multi-component liquid sample (e.g., whole blood) according to certain embodiments. FIG. 6A depicts device 600 having buoy 601 positioned inside of container 602. At the upper edge of the buoy proximal end is positioned a port 603a connecting to conduit 603. At the base of the concave outer surface of the buoy proximal end is a first orifice 604 with ball and spring check valve 605. Device 600 also includes a cap 609 positioned at the proximal end of the container. Multi-component liquid sample (e.g., blood) is introduced into the container with a syringe or other suitable dispensing protocol through port 609b in the cap with gas vent 609a in an open or closed position. After removing device 600 from the centrifuge, a first fraction 610 fills the upper portion of container 602. The container is positioned at an angle (e.g., 20 degrees with respect to an axis orthogonal to the ground) and a portion of the first fraction 610 is removed by aspirating through the conduit which is in fluid communication with the first fraction through the port 603a. After the amount of first fraction that can be removed through port 603*a* (i.e., the level of first fraction falls below the level of port 603*a*), a remaining portion of the first fluid remains in the container at the surface of the buoy proximal end (FIG. 6B).

In certain embodiments, to remove the remaining portion of the first fraction, the container is rotated 180 degrees along the longitudinal axis of the container such that the remaining portion of the first fraction is again in fluid communication with port 603*a*. As described above, the remaining portion of the first fraction may be aspirated through the conduit and reinjected to mix the remaining portion of the first fraction (e.g., platelet poor plasma) with a second fraction (e.g., buffy coat) which collects at the buoy proximal end.

Figure 7D:
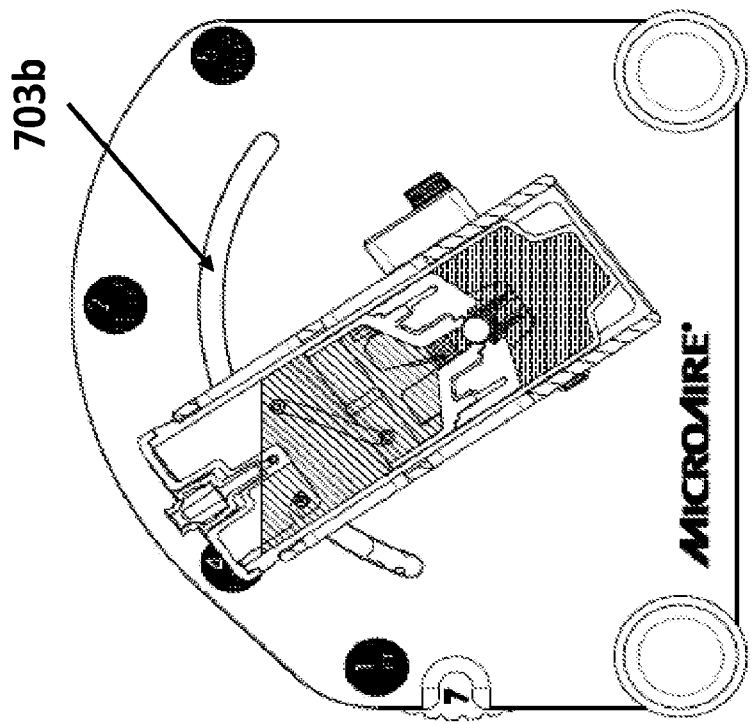
FIG. 7D illustrates step-by-step methods for separating components of a multi-component liquid sample according to certain embodiments. The receptacle is pivoted to a first angular position.

FIGS. 7A-7H illustrate step-by-step methods for separating components of a multi-component liquid sample (e.g., whole blood) according to certain embodiments. FIG. 7A depicts device 700 having a buoy 701 positioned inside of container 702. Buoy 701 includes one or more sealed chambers 707. At the base of the proximal end of buoy 701 is a first orifice 706 having a deflector plate 707 in fluid communication with channel 709 and second orifice 710. Second orifice 710 is sealed by ball and spring valve 715 in the closed position. Device 700 also includes a cap 703 positioned at the proximal end of the container. The proximal end of buoy 701 is in fluid communication with a single port 704 in lid 703 through conduit 705. Multi-component liquid sample 711 (e.g., blood) is introduced into the container with a syringe or other suitable dispensing protocol through port 704 in lid 703.

After centrifugation for a sufficient duration and to a desired relative centrifugal force (as described above), the sample is separated into fractions, such as into a first fraction 711*a*, a second fraction 711*b* and a third fraction 711*c*. For example, where the sample is whole blood, first fraction 711*a* may be platelet poor plasma, second fraction 711*b* may be buffy coat and third fraction 711*c* may be packed red blood cells. As shown here, second fraction 711*b* (e.g., buffy coat) collects within channel 708 in response to the opening of valve 715 during centrifugation.

Figure 7C:
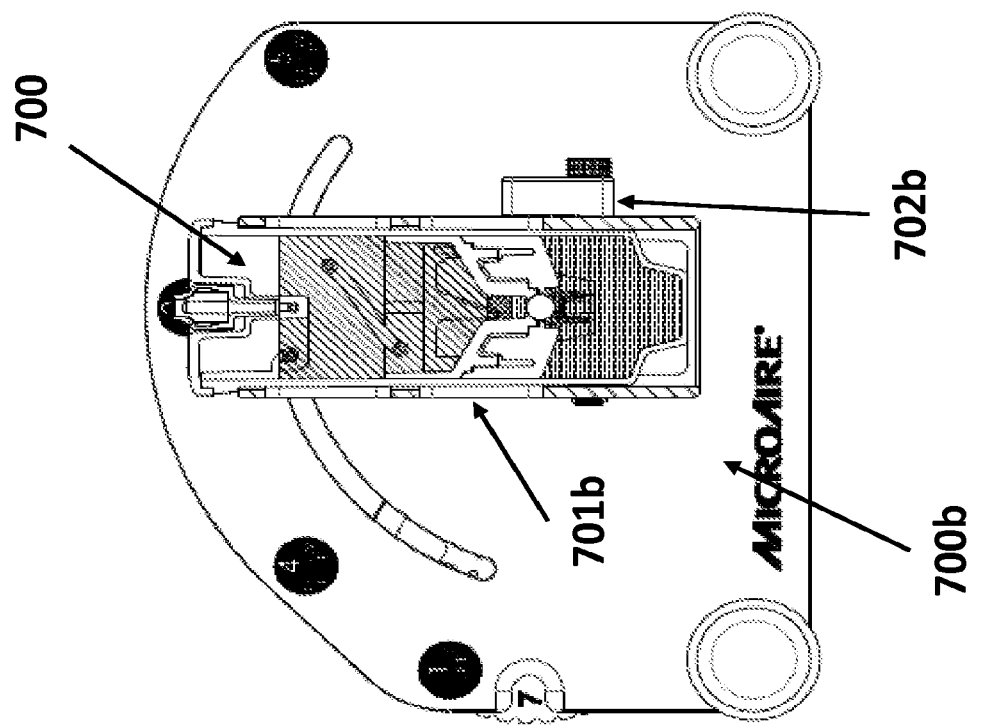
FIG. 7C illustrates step-by-step methods for separating components of a multi-component liquid sample according to certain embodiments. The device is first placed into a receptacle of a tilter stand.
Figure 7F:
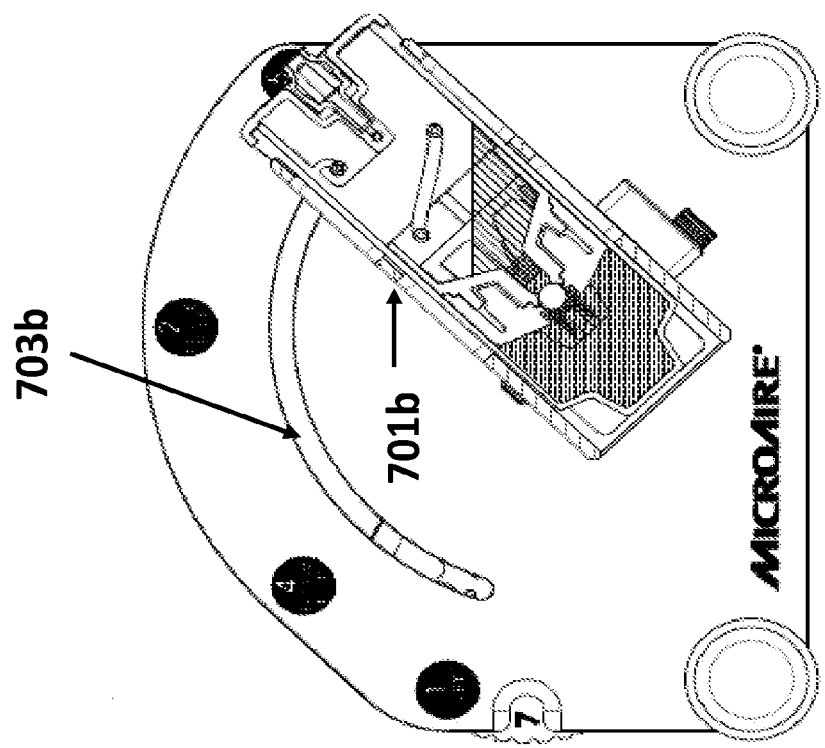
FIG. 7F illustrates step-by-step methods for separating components of a multi-component liquid sample according to certain embodiments. The receptacle is pivoted to a second angular position.
Figure 7E:
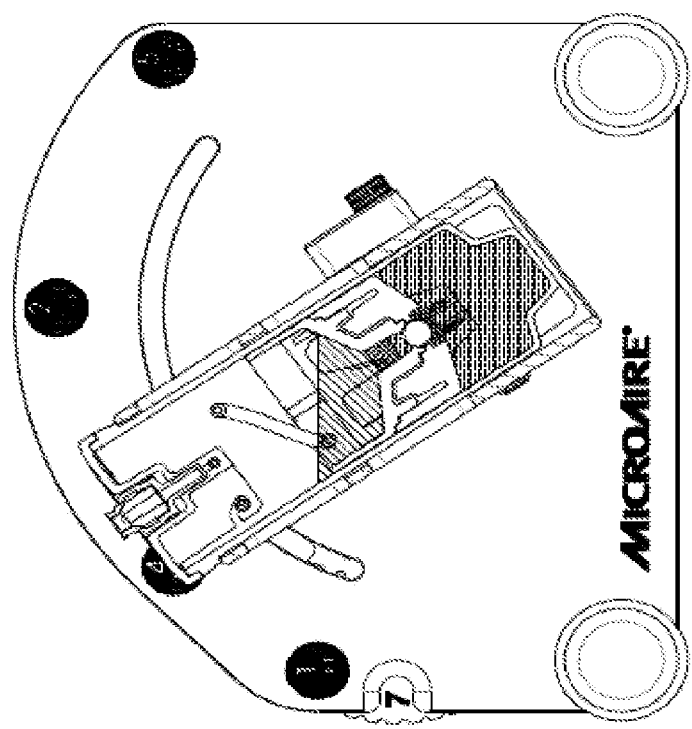
FIG. 7E illustrates step-by-step methods for separating components of a multi-component liquid sample according to certain embodiments. The device comprising the remaining portion of the first fraction after a portion of a first fraction of the sample is aspirated.
Figure 7H:
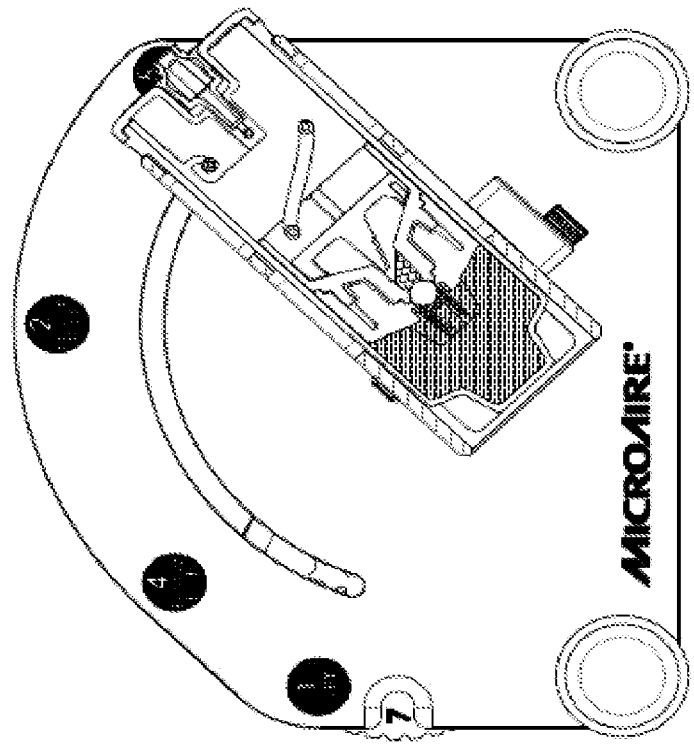
FIG. 7H illustrates step-by-step methods for separating components of a multi-component liquid sample according to certain embodiments. The mixture is removed from the container.
Figure 7G:
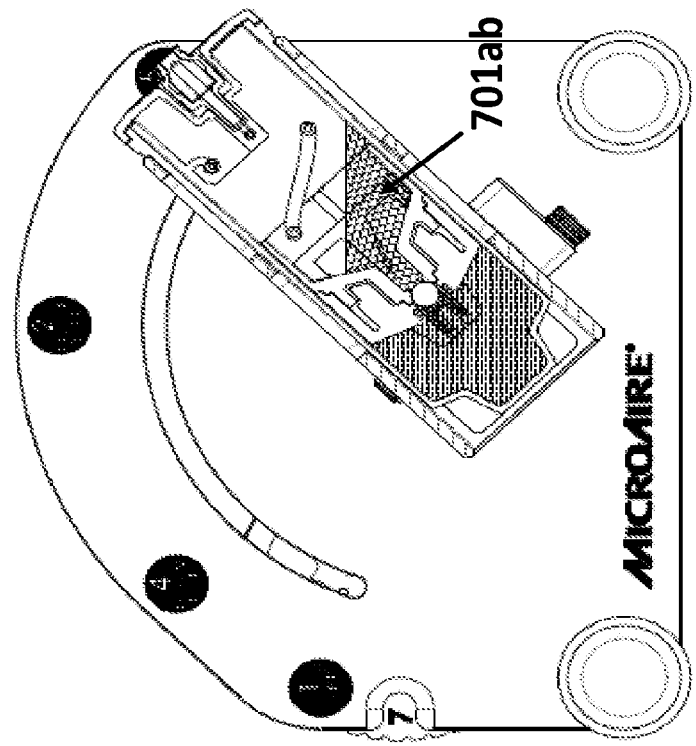
FIG. 7G illustrates step-by-step methods for separating components of a multi-component liquid sample according to certain embodiments. The remaining portion of the first fraction is aspirated and reintroduced back into the device to mix with a second fraction.

After centrifugation is complete, the desired components of the sample are collected. To collect the desired components, device 700 is first placed into receptacle 701*b* of tilter stand 700*b* (described in greater detail below), aligned and clamped with locking lever 702*b* (FIG. 7C). Next, receptacle 701*b* is pivoted along groove 703*b* of the tilter stand to a first angular position (FIG. 7D). A portion of a first fraction of the sample (711*a*) is aspirated through port 704 (via conduit 705) from the proximal end of buoy 701. After aspirating a portion of the first fraction, the remaining portion of the first fraction remains in the device above the proximal end of the buoy (FIG. 7E). Next, receptacle 701*b* is pivoted along groove 703*b* of the tilter stand to a second angular position (FIG. 7F). The remaining portion of the first fraction that remains above the proximal end of the buoy is aspirated through port 704 (via conduit 705) at the second angular position and reintroduced back into the device to mix with second fraction 711*b* at the top of the centrifuge activated valve to produce a mixture of the first fraction and second fraction 711*ab* (e.g., platelet rich plasma) (FIG. 7G). This mixture is then removed from the container through port 704 (FIG. 7H).

Figure 8:
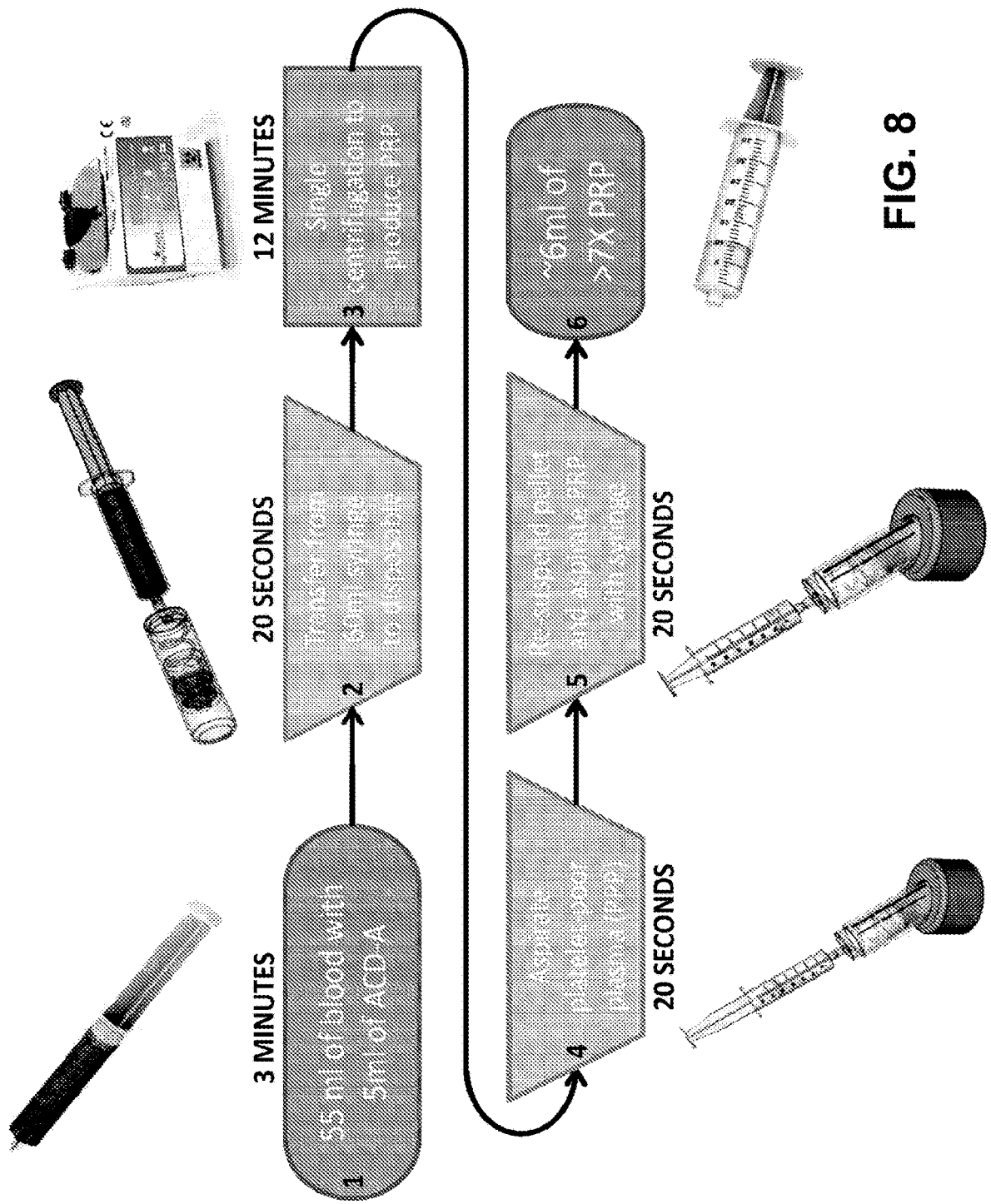
FIG. 8 depicts an example flow diagram of separating components of a biological sample according to certain embodiments.

FIG. 8 graphically illustrates an example of separating components of a blood sample according to certain embodiments. In step 1, an amount of blood (55 mL with 5 mL of anticoagulant) is obtained or drawn into a syringe. The blood sample is transferred from a syringe into one or more of the subject devices as described above through a port in the cap (step 2). As described above, the sample is subjected to a force of centrifugation by placing into a centrifuge (step 3). After removing the device from the centrifuge, a portion of the platelet poor plasma is removed with an aspirating syringe (step 4). At step 5, the remaining portion of the platelet poor plasma is aspirated into a syringe and reinjected to rinse and mix the platelet poor plasma with the buffy coat which collects on the buoy (step 5). After sufficient mixing of the remaining portion of platelet poor plasma with buffy coat, the mixture (platelet rich plasma) is removed by aspirating into a syringe (step 6).

Systems for Separating by Centrifugation

Aspects of the present disclosure also include systems for practicing the subject methods. As discussed above, methods for separating components according to embodiments of the present disclosure include introducing a multi-component liquid sample (e.g., blood) into a container of one or more of the subject separation devices described above, subjecting the sample to a force of centrifugation to produce two or more fractions in the sample, each fraction having a component from the sample of a different density and collecting one or more components of the sample. In embodiments, systems are configured to apply a force of centrifugation to the sample in the subject devices for a duration sufficient to fractionate the components of the sample into two or more fractions (e.g., layers), each fraction containing components of different density. Components of the sample are separated such that each component has a higher concentration in a particular fraction (e.g., bottom layer, upper layer, middle layer, etc.) as compared to the sample before being subjected to the force of centrifugation. In other words, components of the multi-component liquid sample are fractionated in a manner sufficient to enrich the components into particular layers within the liquid sample.

In some embodiments, systems include one or more of the subject devices described above and a support for positioning the container at an angle with respect to the axis orthogonal to the ground. For instance, the support may be configured to position and maintain the container at an angle that is 20 degrees or more with respect to the axis orthogonal to the ground, such as 30 degrees or more, such as 45 degrees or more and including being configured to position and maintain the container at an angle that is 60 degrees with respect to the axis orthogonal to the ground as 60 degrees or more. As such, the container may be positioned at an angle that is sufficient to allow for removal of the desired amount of the first fraction through the conduit, such at an angle of 20 degrees or more relative to an axis orthogonal to the ground, such as 25 degrees or more, such as 30 degrees or more, such as 35 degrees or more, such as 45 degrees or more and including positioning the container at an angle that is 60 degrees or more relative to an axis orthogonal to the ground.

The support may be any suitable support protocol, including but not limited to a manual support (e.g., stand) or with a manual, mechanical or automated actuator. In some embodiments, systems may include a platform with a hinge or latch at a proximal edge of the container where the actuator positions the support at an angle by raising the distal edge of the container. In other embodiments, the support protocol is a tilter stand configured to receive the device into a receptacle and to position the device at any desired angular position. In other embodiments, the actuator may be a lift column that is coupled to the bottom of the container and positioning of the container by the actuator at an angle includes adjusting a pivot or rocker. In some instances, actuation of the container to the desired angle is carried out manually (i.e., positioning of the container by hand).

In other instances, the actuator is a mechanical actuation device, such as for example a mechanical lead screw assembly or a mechanically operated geared translation device. In yet other embodiments, the actuator is a motor-driven displacement device, such as a motor actuated displacement stage, motor driven leadscrew assembly, motor-operated geared actuation device employing a stepper motor, servo motor, brushless electric motor, brushed DC motor, microstep drive motor, high resolution stepper motor, among other types of motors.

In some embodiments, the support includes a fastener for holding the device in the support in place. For example, fasteners may include, but are not limited to hook and loop fastener, a latch, a notch, a groove, a pin, a tether, a hinge, Velcro, non-permanent adhesive, a threaded screw, a dowel or a combination thereof.

Figure 9B:
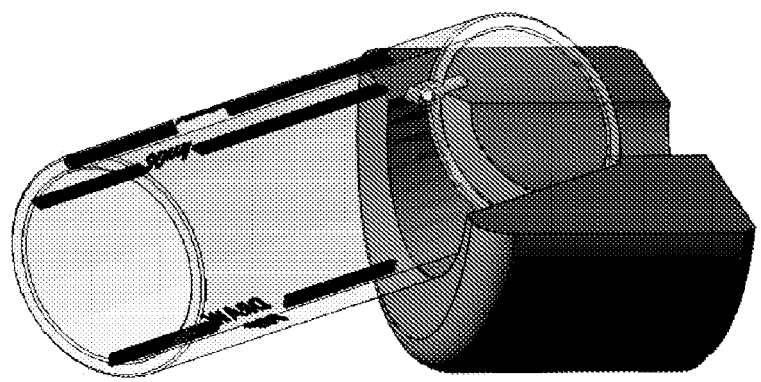
FIG. 9B illustrates an example of a support for positioning one or more of the subject devices described above at an angle according to certain embodiments.
Figure 9A:
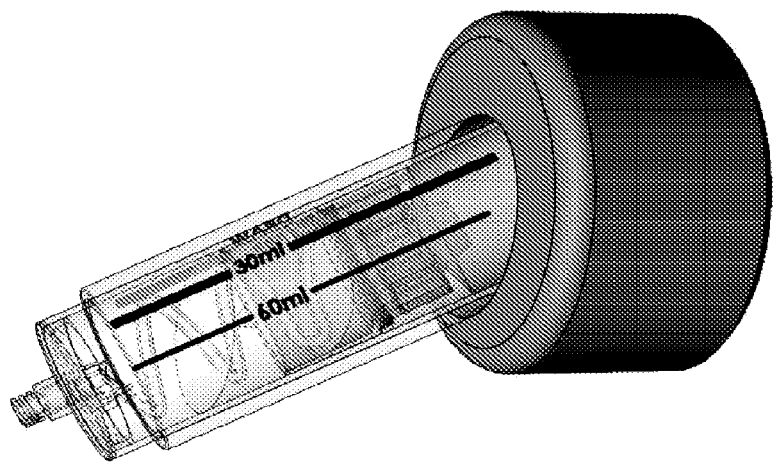
FIG. 9A illustrates an example of a support for positioning one or more of the subject devices described above at an angle according to certain embodiments. The device is positioned in the support with the distal end in the support cradle with access to the inlet/outlet port.

FIGS. 9A-9B illustrate an example of a support for positioning one or more of the subject devices described above at an angle with respect to the axis orthogonal to the ground, where the angle may vary, ranging in some instances from 5 to 85°, such as 10 to 75°, including 15 to 50°, e.g., 15 to 40°, such as 15 to 30°, e.g., 20 to 25°. As shown in FIG. 9A, the device is positioned in the support with the distal end in the support cradle with access to the inlet/outlet port. FIG. 9B illustrates that the container of the subject device may be locked in place with a fastener, such as a pin, dowel or other fasteners (as described above).

Figure 10B:
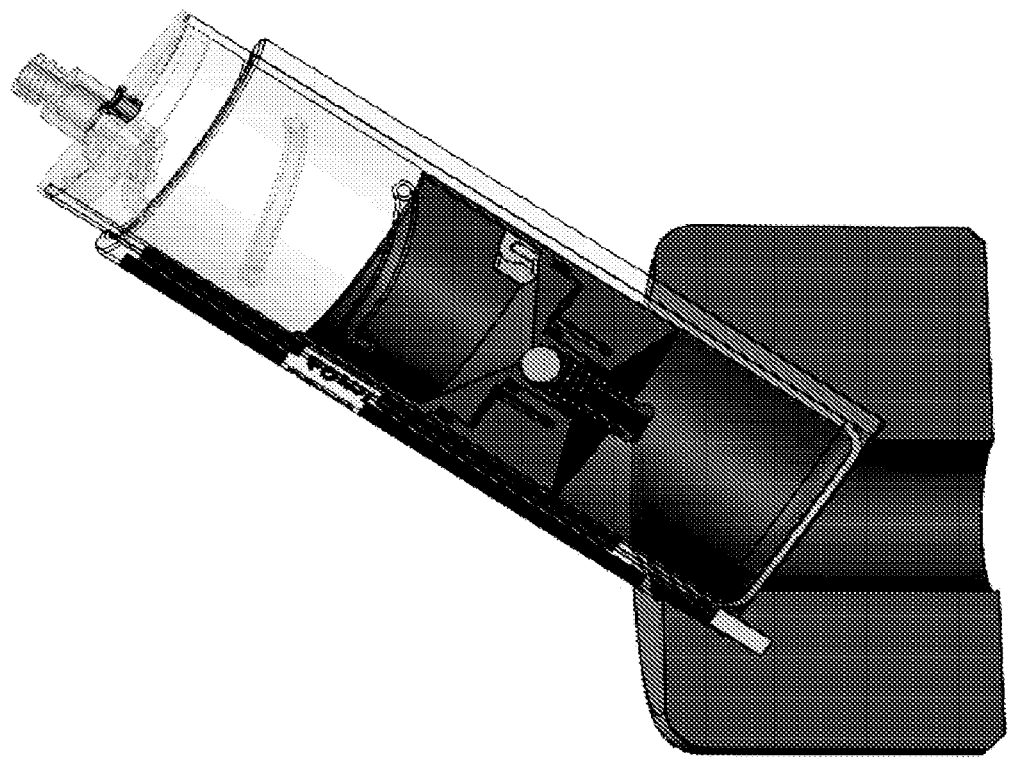
FIG. 10B illustrates an example of placing one or more of the subject devices at an angle in a support to collect one or more components of a separated multi-component liquid according to certain embodiments. An exploded view of the device where the buoy port is at the lowest possible position (e.g., the concave outer surface of the buoy proximal end slopes downward) which facilitates removal of the separated components of the multi-component liquid.
Figure 10A:
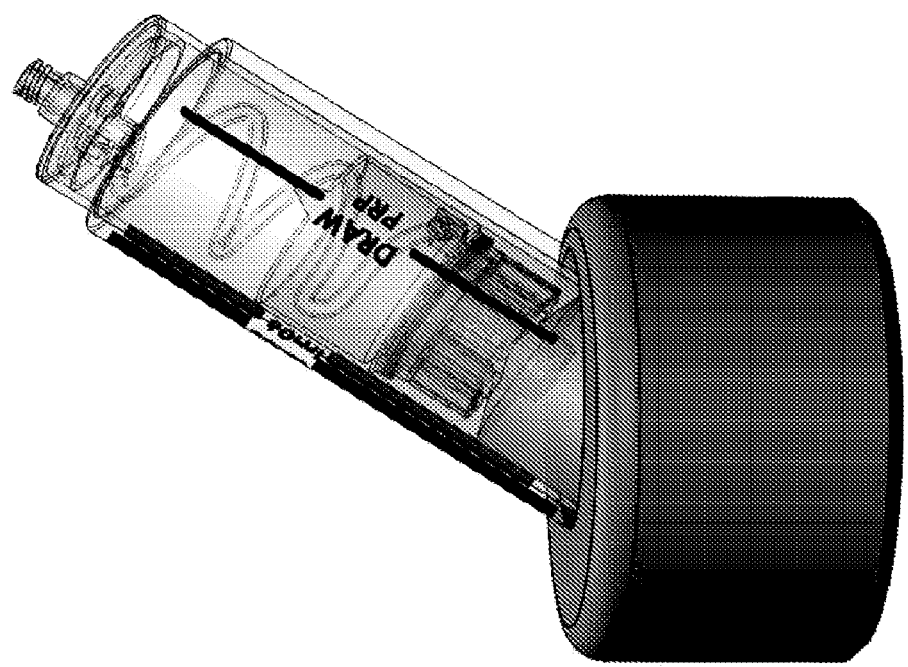
FIG. 10A illustrates an example of placing one or more of the subject devices at an angle in a support to collect one or more components of a separated multi-component liquid according to certain embodiments. The device is positioned at an angle with the distal portion of the container inserted into the support with access to inlet/outlet port. In this embodiment, the angular position indicator on the side of the device is lined up with a mark on the support.

FIGS. 10A-10B illustrate an example of placing one or more of the subject devices at an angle in a support to collect one or more components of a separated multi-component liquid according to another embodiment. As shown in FIG. 10A, the device is positioned in the device at an angle with the distal portion of the container inserted into the support with access to inlet/outlet port. In this embodiment, the angular position indicator on the side of the device is lined up with a mark on the support. FIG. 10B depicts an exploded view of the device where the buoy port is at the lowest possible position (e.g., the concave outer surface of the buoy proximal end slopes downward) which facilitates removal of the separated components of the multi-component liquid.

Figure 11C:
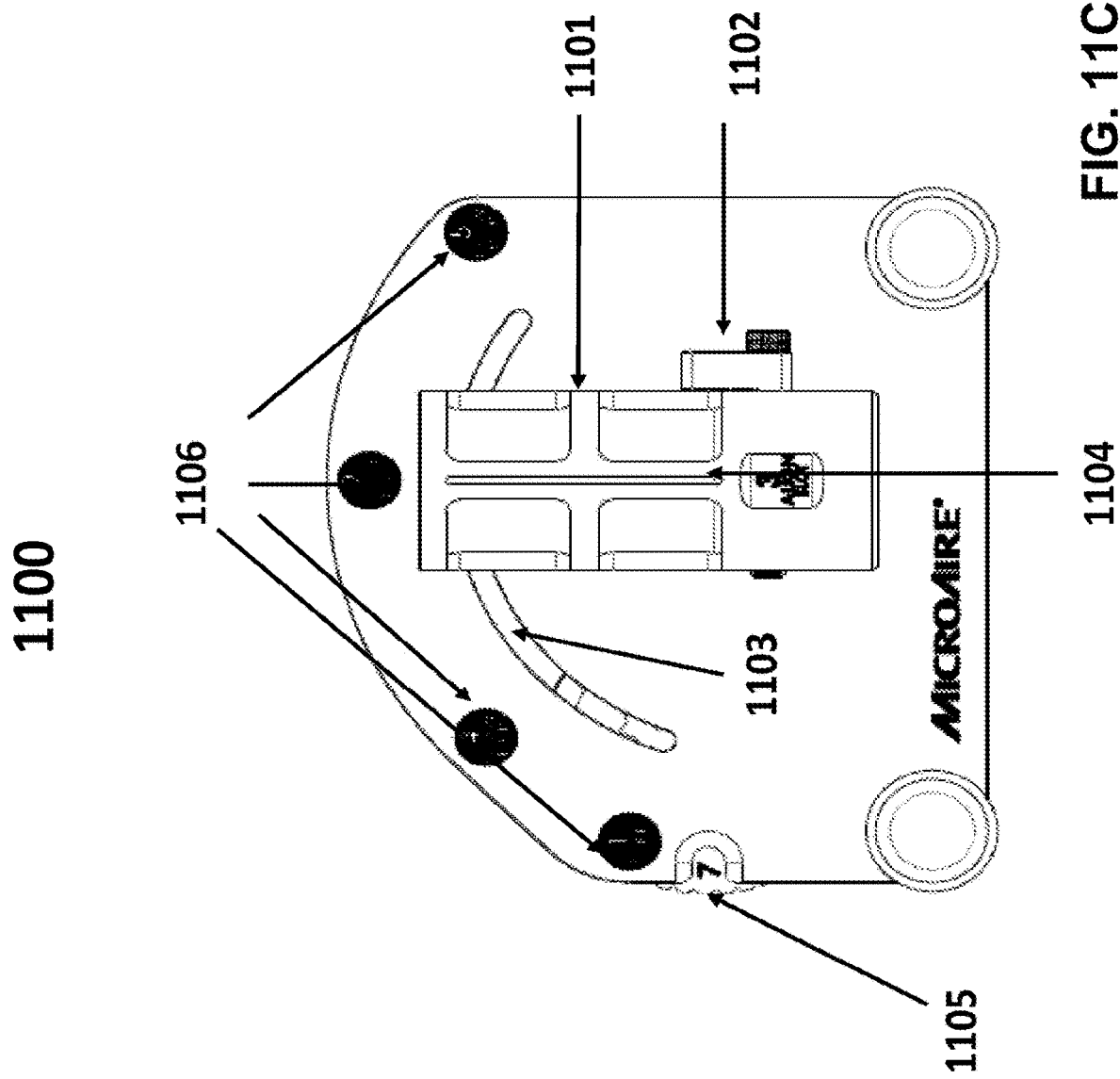
FIG. 11C depicts an adjustable tilter stand for positioning the device at a desired angle to remove one (or a portion) or more fractions after centrifugation according to certain embodiments. The tilter stand from a front-facing perspective.

FIGS. 11A-11C depict an adjustable tilter stand for positioning the device at a desired angle to remove one (or a portion) or more fractions after centrifugation according to certain embodiments as described above. FIGS. 11A and 11B show two different three-dimensional perspectives of the tilter stand. Tilter stand 1100 includes a receptacle 1101 for holding and pivoting one of the subject devices. FIGS. 11A and 11B depict the receptacle at a first angle (90 degrees) with respect to an axis orthogonal to the ground. The device may be secured in receptacle 1101 with locking lever 1102. Tilter stand 1100 includes groove 1103 configured to position receptacle 1101 at a plurality of angular positions. In certain embodiments, groove 1103 includes one or more notches for positioning receptacle 1101 at discreet positions (i.e., discreet angles with respect to an axis orthogonal to the ground). In other embodiments, receptacle 1101 may be moved continuously along groove 1103 and secured at any desired angular position, such as with a pin or screw. Tilter stand 1100 also includes a selector wheel 1105 which may be used to set one or more predetermined positions of the receptacle at a desired angle as receptacle 1101 is pivoted along groove 1103. Receptacle 1101 also includes a visual alignment slot 1104 to ensure proper placement of the device within receptacle 1101. The periphery of tilter stand 1100 may also include one or more labels 1106 for predetermined positions for pivoting and securing receptacle 1101 along groove 1103 to collect one or more fractions from the subject devices (as described in greater detail below).

FIG. 11C depicts tilter stand 1100 from a front-facing perspective. Tilter stand 1100 includes receptacle 1101 for holding and pivoting one of the subject devices. Devices placed in receptacle 1101 may be secured with locking lever 1102. Devices positioned in receptacle 1101 are pivoted to the desired angular position along groove 1103. FIG. 11C also shows selector wheel 1105 to set one or more predetermined positions of the receptacle at a desired angle. Receptacle 1101 in FIG. 11C also depicts visual alignment slot 1104. One or more labels 1106 for pivoting and securing receptacle 1101 at predetermined angular positions to collect one or more fractions from the subject devices may be included, in certain embodiments, along the periphery of tilter stand 1100.

In addition to one or more of the subject separation devices described above, systems of interest may also include a centrifuge for applying a force of centrifugation to the sample. The term "centrifuge" is used herein in its conventional sense to refer to an apparatus for rotating one or more of the subject separation devices about a rotation axis to apply a centrifugal force to the components of the sample in the device container. Any convenient centrifuge protocol may be employed, including but not limited to fixed-angle centrifuges, swinging bucket centrifuges, ultracentrifuges, solid bowl centrifuges, conical centrifuges, among other types of centrifuges. In certain embodiments, the centrifuge is a centrifuge with a horizontal rotor. In other embodiments, the centrifuge is a centrifuge with a fixed angle rotor. For example, the centrifuge may be certain instances a Horizon Model 755VES centrifuge (Drucker Co., Port Matilda Pa.) having a horizontal rotor or fixed angle rotor and brushless DC motor.

As described above, the subject centrifuges may be configured to apply a force of centrifugation which varies, depending on the type of sample, size of separation device and desired separation of sample components. In embodiments, centrifuges of interest may apply a force of centrifugation which ranges (in relative centrifugal force, RCF) from 1 g to 50,000 g, such as from 2 g to 45,000 g, such as from 3 g to 40,000 g, such as from 5 g to 35,000 g, such as from 10 g to 25,000 g, such as from 100 g to 20,000 g, such as from 500 g to 15,000 g and including from 1000 g to 10,000 g. Accordingly, centrifuges of interest may be configured to operate at rotation speeds which vary widely, such as from $1 \times 10^3$ revolutions per minute (rpm) to $1000 \times 10^3$ rpm, such as from $2 \times 10^3$ rpm to $900 \times 10^3$ rpm, such as from $3 \times 10^3$ rpm to $800 \times 10^3$ rpm, such as from $4 \times 10^3$ rpm to $700 \times 10^3$ rpm, such as from $5 \times 10^3$ rpm to $600 \times 10^3$ rpm, such as from $10 \times 10^3$ rpm to $500 \times 10^3$ rpm and including from $25 \times 10^3$ rpm to $100 \times 10^3$ rpm.

The centrifuge may also be a temperature-controlled centrifuge, where the temperature of the sample in the subject devices may be maintained or changed (e.g., increased or decreased) as desired. For example, the centrifuge may be configured to maintain the temperature of the sample in the subject devices from −80° C. to 100° C., such as from −75° C. to 75° C., such as from −50° C. to 50° C., such as from −25° C. to 25° C., such as from −10° C. to 10° C., and including from 0° C. to 25° C.

Centrifuges of interest may also be configured with monitoring protocols for assessing the sample during centrifugation. For example, the centrifuge may include a viewing window to visually observe centrifugation or may include one or more sensors, such as laser scatter sensors, fluorescence sensors, phosphorescence sensors, chemiluminescence sensors, diffuse reflectance sensors, infrared sensors, among other sensing protocols.

In certain embodiments, systems of interest further include computer-controlled systems for practicing the subject methods, where the systems may include one or more computers for automation or semi-automation of a system for practicing methods described herein. In these embodiments, systems may include a computer having a computer readable storage medium with a computer program stored thereon, where the computer program when loaded on the computer includes algorithm for controlling a liquid dispensing device to introduce a multi-component liquid sample (e.g., blood) into a container of one or more of the subject separation devices, algorithm for subjecting the sample to a force of centrifugation to produce two or more fractions in the sample and algorithm for controlling a liquid collection device to collect one or more separated components of the sample. In certain embodiments, the computer program may also include algorithm for providing a blood sample from a sample source to the liquid dispensing device. For example, where the sample is a whole blood sample, the computer processor may also include algorithm for transferring the whole blood sample from a blood collection tube into the container of one or more of the subject separation devices.

In embodiments, the computer-controlled system includes an input module and a processing module. In some embodiments, the subject systems may include an input module such that parameters or information about: 1) each sample including the type of sample (e.g., whole blood, a blood derivative, citrated blood etc.), viscosity of the liquid sample, sample volume and number of separated fractions expected from the sample; 2) components from the sample that are of interest; 3) desired speed of the centrifuge for subjecting the sample to a force of centrifugation; 4) the temperature of the centrifuge and 5) the number of centrifugation intervals, etc. may be inputted into the computer. The processing module includes memory having a plurality of instructions for performing certain steps of the subject methods, such as introducing the multi-component sample into the container of the subject separation devices, applying a force of centrifugation as well as instructions for collecting the separated fractions from the sample.

The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

Computer systems of interest may include a display and operator input device. Operator input devices may, for example, be a keyboard, mouse, or the like. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid state storage devices (including magnetic or optical disks or tape or RAM, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; portable flash drive; and hybrids of these categories such as magnetic/optical storage media.

The processor may also have access to a communication channel to communicate with a user at a remote location. By remote location is meant the user is not directly in contact with the system and relays input information to an input manager from an external device, such as a computer connected to a Wide Area Network ("WAN"), telephone network, satellite network, or any other suitable communication channel, including a mobile telephone (e.g., smartphone) or tablet device.

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g., over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Windows XP, Windows 7, Windows 8, iOS, Sun Solaris, Linux, OS/400, Compaq Tru64 Unix, SGI IRIX, Siemens Reliant Unix, and others.

Kits

Aspects of the invention further include kits, where kits include one or more of the subject separation devices having a container and a buoy configured to be displaced along a longitudinal axis within the container as described herein. In some instances, the kits can include one or more additional components (e.g., buffers, water, solvent etc.). In some instances, the kits may further include a sample collection device, e.g., blood collection device such as an evacuated blood collection tube, needle, syringe, pipette, tourniquet, etc. as desired.

The various assay components of the kits may be present in separate containers, or some or all of them may be pre-combined. For example, in some instances, one or more components of the kit, e.g., the separation device, containers, buoys, are present in a sealed pouch, e.g., a sterile foil pouch or envelope.

In addition to the above components, the subject kits may further include (in certain embodiments) instructions for assembling the subject kit components as well as for practicing the methods for separating components of a multi-component liquid sample as described herein. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

Utility

The subject devices, methods and systems find use in a variety of applications where it is desirable to separate components of a multi-component liquid sample. Embodiments of the present disclosure also find use in purifying components of a biological sample, such as whole blood and bone marrow aspirate where it is desirable to obtain isolated components of blood (e.g., white blood cells, stem cells, red blood cells, platelets, plasma, etc.) In some embodiments, the present disclosure finds use in preparing blood products having therapeutic applications, such as platelet rich plasma. Embodiments also find use in the preparation of samples from multi-component liquid where only certain components are desired, such as for laboratory assays, diagnostic tests or for other research applications.

In addition, applications of the present disclosure also find use where components (e.g., cells, proteins, polysaccharides or other large macromolecular compound) prepared from a biological sample may be desired for laboratory testing or for use in therapy. For example, the subject devices and methods facilitate obtaining blood products that may be used to treat wounds, accelerate tissue growth or other ailments, such as fistulas.

Notwithstanding the appended clauses, the disclosure set forth herein is also defined by the following clauses:

1. A device for separating components of a multi-component liquid, the device comprising:
   a container comprising a distal end and a proximal end; and
   a buoy configured to be displaced along a longitudinal axis within the container, wherein the buoy comprises one or more sealed chambers.

2. The device according to clause 1, wherein the buoy comprises a frustoconical shaped component.

3. The device according to clause 2, wherein the buoy comprises a cylindrical proximal portion and frustoconical distal portion.

4. The device according to clause 2, wherein the proximal end of the buoy comprises a concave outer surface.

7. The device according to clause 1, wherein the buoy has a density from 1.01 g/mL to 1.2 g/mL.

8. The device according to clause 7, wherein the buoy has a density from 1.04 g/mL to 1.07 g/mL.

9. The device according to clause 7, wherein the buoy has a density from 1.045 g/mL to 1.060 g/mL.

10. The device according to clause 2, wherein the distal end of the buoy comprises a convex outer surface.

11. The device according to clause 2, wherein the distal end of the buoy comprises a concave outer surface.

11. The device according to clause 4, wherein the buoy comprises:
    an orifice at the base of the concave outer surface; and
    a centrifuge activated valve comprising an open position and a closed position, wherein the valve is configured in the closed position to fluidically seal the orifice at the base of the concave outer surface.
12. The device according to clause 11, wherein the centrifuge activated valve is an umbrella valve.
13. The device according to clause 11, wherein the centrifuge activated valve is a check valve.
14. The device according to clause 13, wherein the centrifuge activated valve is selected from the group consisting of a ball check valve, a diaphragm check valve, a lift check valve and a tilted disc check valve.
15. The device according to clause 11, wherein the centrifuge activated valve comprises a ball and spring.
16. The device according to clause 15, wherein the ball comprises metal.
17. The device according to clause 15, wherein the ball comprises stainless steel metal.
18. The device according to clause 4, wherein the buoy comprises:
    a first orifice at the base of the concave outer surface;
    a second orifice at a position distal along the longitudinal axis of the buoy to the first orifice; and
    a channel that extends from the first orifice to the second orifice;
    a centrifuge activated valve comprising an open position and a closed position, wherein the valve is configured in the closed position to fluidically seal the channel.
19. The device according to clause 18, wherein the centrifuge activated valve is positioned at the first orifice.
20. The device according to clause 18, wherein the centrifuge activated valve is positioned at the second orifice.
21. The device according to clause 18, wherein the centrifuge activated valve is positioned within the channel between the first orifice and the second orifice.
22. The device according to clause 18, wherein the centrifuge activated valve is an umbrella valve.
23. The device according to clause 18, wherein the centrifuge activated valve is a check valve.
24. The device according to clause 23, wherein the check valve is selected from the group consisting of a ball check valve, a diaphragm check valve, a lift check valve and a tilted disc check valve.
25. The device according to clause 18, wherein the centrifuge activated valve comprises a ball and spring.
26. The device according to clause 25, wherein the ball comprises stainless steel.
27. The device according to clause 1, wherein the container further comprises a cap positioned at the proximal end comprising an inlet into the cavity of the container.
28. The device according to clause 27, wherein the cap forms a fluidic seal with the internal walls of the container.
29. The device according to clause 27, wherein the cap further comprises a vent port.
30. The device according to clause 1, further comprising a conduit that extends from the inlet to the proximal end of the buoy.
31. The device according to clause 30, wherein the conduit is connected to the proximal end of the buoy at a position adjacent to the inner wall of the container.
32. The device according to clause 30, wherein the conduit is releasably attached to one or more of the inlet and the proximal end of the buoy.
33. The device according to clause 30, wherein the conduit is integrated with one or more of the inlet or the proximal end of the buoy.
34. The device according to clause 30, wherein the conduit is releasably attached to the inlet and integrated with the proximal end of the buoy.
35. The device according to clause 30, wherein the conduit is flexible.
36. The device according to clause 35, wherein the conduit is coiled.
37. The device according to clause 1, wherein the sealed chambers contain a vacuum, a fluidic composition or a combination thereof.
38. The device according to clause 37, wherein one or more sealed chambers contain a vacuum.
39. The device according to clause 37, wherein one or more sealed chambers contain a fluidic composition.
40. The device according to clause 39, wherein the fluidic composition comprises a gaseous composition.
41. The device according to clause 40, wherein the gaseous composition comprises a gas selected from the group consisting of air, carbon dioxide, oxygen, nitrogen, hydrogen, helium, argon, xenon or a combination thereof.
42. The device according to clause 37, wherein the fluidic composition comprises a liquid composition.
43. The device according to clause 42, wherein the fluidic composition comprises an alcohol.
44. The device according to clause 37, wherein one or more sealed chambers contain a vacuum and one or more sealed chambers contain a fluidic composition.
45. The device according to clause 1, wherein the one or more sealed chambers comprises 25% or more of the total volume of the buoy.
46. The device according to clause 45, wherein the one or more sealed chambers comprises 50% or more of the total volume of the buoy.
47. The device according to clause 1, wherein the buoy comprises a polymer selected from the group consisting of polycarbonate, polycarbonate alloys, polyethylene, polypropylene, polytetrafluoroethylene (PTFE), polyvinylidene fluoride (PVDF), ethyl vinyl acetate (EVA), polyurethane, polyethersulfone, copolymers and combinations thereof.
48. The device according to clause 47, wherein the buoy comprises polycarbonate.
49. The device according to any of the preceding claims, wherein the multi-component liquid comprises a biological fluid.
50. The device according to clause 49, wherein the biological fluid is selected from the group consisting of whole blood or a derivative thereof, bone marrow aspirate or a derivative thereof, stromal vascular fractions or a derivative thereof or any combination thereof.
51. The device according to clause 50, wherein the biological fluid is whole blood or a derivative thereof.
52. The device according to clause 50, wherein the biological fluid is bone marrow aspirate or a derivative thereof.
53. The device according to clause 50, wherein the biological fluid is a stromal vascular fraction or a derivative thereof.
54. The device according to clause 50, wherein the biological fluid comprises two or more of:
    whole blood or a derivative thereof;
    bone marrow aspirate or a derivative thereof; and
    stromal vascular fractions or a derivative thereof.
55. The device according to clause 54, wherein the biological fluid comprises whole blood or a derivative thereof, bone marrow aspirate or a derivative thereof and stromal vascular fractions or a derivative thereof.

56. A device for separating components of a multi-component liquid, the device comprising:
   a container comprising a buoy according to any of the preceding claims; and
   a multi-component liquid present in the device.

57. The device according to clause 56, wherein the multi-component liquid comprises a biological fluid.

58. The device according to clause 57, wherein the biological fluid is selected from the group consisting of whole blood or a derivative thereof, bone marrow aspirate or a derivative thereof, stromal vascular fractions or a derivative thereof or any combination thereof.

59. The device according to clause 58, wherein the biological fluid is whole blood or a derivative thereof.

60. The device according to clause 58, wherein the biological fluid is bone marrow aspirate or a derivative thereof.

61. The device according to clause 58, wherein the biological fluid is a stromal vascular fraction or a derivative thereof.

62. The device according to clause 58, wherein the biological fluid comprises two or more of:
   whole blood or a derivative thereof;
   bone marrow aspirate or a derivative thereof; and
   stromal vascular fractions or a derivative thereof.

63. The device according to clause 62, wherein the biological fluid comprises whole blood or a derivative thereof, bone marrow aspirate or a derivative thereof and stromal vascular fractions or a derivative thereof.

64. A method comprising:
   introducing a blood sample into a device comprising:
      a container comprising a distal end and a proximal end; and
      a buoy configured to be displaced along a longitudinal axis within the container, wherein the buoy comprises one or more sealed chambers comprising a fluidic composition;
   subjecting the blood sample to a force of centrifugation to produce two or more fractions in the blood sample;
   collecting one or more components of the blood sample.

65. The method according to clause 64, wherein collecting one or more components of the blood sample comprises:
   removing a portion of a first fraction of the blood sample;
   mixing the remaining portion of the first fraction with a second fraction within the buoy to produce a mixture of the first fraction and the second fraction; and
   removing the mixture from the container.

66. The method according to clause 65, wherein the first fraction comprises platelet poor plasma.

67. The method according to clause 65, wherein the second fraction comprises platelets and white blood cells.

68. The method according to clause 65, wherein 75% by volume or more of the first fraction is removed from the blood sample.

69. The method according to clause 68, wherein 90% by volume or more of the first fraction is removed from the blood sample.

70. The method according to clause 65, wherein mixing the remaining portion of the first fraction with the second fraction comprises:
   aspirating the remaining portion of the first fraction and the second fraction into a syringe; and
   reinjecting the first fraction and the second fraction within the buoy to produce a mixture of the first fraction and the second fraction.

71. The method according to clause 64, wherein the buoy comprises a frustoconical shape.

72. The method according to clause 71, wherein the buoy comprises:
   a proximal end having a concave outer surface;
   an orifice at the base of the concave outer surface; and
   a centrifuge activated valve comprising an open position and a closed position, wherein the valve is configured in the closed position to fluidically seal the orifice at the base of the concave outer surface.

73. The method according to clause 72, wherein the centrifuge activated valve is an umbrella valve.

74. The method according to clause 72, wherein the centrifuge activated valve is a check valve.

75. The method according to clause 72, wherein the centrifuge activated valve comprises a ball and spring.

76. The method according to clause 72, wherein subjecting the blood sample to a force of centrifugation is sufficient to switch the centrifuge activated valve to an open position.

77. The method according to clause 76, wherein subjecting the blood sample to a force of centrifugation comprises subjecting the blood sample to a first force of centrifugation when the centrifuge activated valve is in an open position and subjecting the blood sample to a second force of centrifugation when the centrifuge activated valve is in a closed position.

78. The method according to clause 76, wherein subjecting the blood sample to a force of centrifugation is sufficient to collect a fraction of the blood sample on the concave outer surface of the buoy.

79. The method according to clause 78, wherein subjecting the blood sample to a force of centrifugation is sufficient to collect a fraction of the blood sample adjacent to the orifice at the base of the concave outer surface.

80. The method according to clause 64, wherein the buoy comprises:
   a first orifice at the base of the concave outer surface;
   a second orifice at a position distal along the longitudinal axis of the buoy to the first orifice; and a channel that extends from the first orifice to the second orifice;
   a centrifuge activated valve comprising an open position and a closed position, wherein the valve is configured in the closed position to fluidically seal the channel.

81. The method according to clause 80, wherein the centrifuge activated valve is positioned at the first orifice.

82. The method according to clause 80, wherein the centrifuge activated valve is positioned at the second orifice.

83. The method according to clause 80, wherein the centrifuge activated valve is positioned within the channel between the first orifice and the second orifice.

84. The method according to clause 80, wherein the centrifuge activated valve is an umbrella valve.

85. The method according to clause 80, wherein the centrifuge activated valve is a check valve.

86. The method according to clause 85, wherein the check valve comprises a ball and spring.

87. The method according to clause 80, wherein subjecting the blood sample to a force of centrifugation is sufficient to switch the centrifuge activated valve to an open position.

88. The method according to clause 87, wherein subjecting the blood sample to a force of centrifugation comprises subjecting the blood sample to a first force of centrifugation when the centrifuge activated valve is in an open position and subjecting the blood sample to a second force of centrifugation when the centrifuge activated valve is in a closed position.

89. The method according to clause 87, wherein subjecting the blood sample to a force of centrifugation is sufficient to collect a fraction of the blood sample in the channel.

90. The method according to clause 89, wherein subjecting the blood sample to a force of centrifugation is sufficient to collect a fraction of the blood sample in the channel adjacent to the first orifice.

91. The method according to clause 89, wherein subjecting the blood sample to a force of centrifugation is sufficient to collect a fraction of the blood sample in the channel adjacent to the second orifice.

92. The method according to clause 89, wherein subjecting the blood sample to a force of centrifugation is sufficient to collect a fraction of the blood sample on the concave outer surface of the buoy.

93. The method according to clause 87, wherein subjecting the blood sample to a force of centrifugation is sufficient to collect a fraction of the blood sample on the concave outer surface of the buoy adjacent to the first orifice.

94. The method according to clause 64, wherein collecting one or more components of the biological sample comprises:
positioning the device at a first angle with respect to an axis orthogonal to the ground;
removing a portion of a first fraction of the biological sample;
rotating the device by a second angle along the longitudinal axis of the device;
aspirating the remaining portion of the first fraction of the biological sample through the conduit;
mixing the remaining portion of the first fraction with a second fraction within the buoy to produce a mixture of the first fraction and second fraction; and
removing the mixture from the container.

95. The method according to clause 64, wherein collecting one or more components of the biological sample comprises:
positioning the device at a first angular position with respect to an axis orthogonal to the ground;
removing a portion of a first fraction of the biological sample;
tilting the device to a second angular position with respect to the axis orthogonal to the ground;
aspirating the remaining portion of the first fraction of the biological sample;
mixing the remaining portion of the first fraction with a second fraction within the buoy to produce a mixture of the first fraction and the second fraction; and
removing the mixture from the container.

96. The method according to clause 95, wherein the second angular position is from 5° to 20° with respect to the first angular position of the device.

97. The method according to clause 95, wherein the second angular position is 10° with respect to the first angular position.

98. The method according to clause 64, wherein the container comprises:
a cap positioned at the proximal end comprising an inlet into the cavity of the container; and
a conduit that connects the inlet to the proximal end of the buoy.

99. The method according to clause 98, wherein the conduit is connected to the proximal end of the buoy at a position adjacent to the inner wall of the container.

100. The method according to clause 99, wherein collecting one or more components of the blood sample comprises:
positioning the container at a first angle with respect to an axis orthogonal to the ground;
removing a portion of a first fraction of the blood sample through the conduit;
rotating the container by a second angle along the longitudinal axis of the container;
aspirating the remaining portion of the first fraction of the blood sample through the conduit;
mixing the remaining portion of the first fraction with a second fraction within the buoy to produce a mixture of the first fraction and second fraction; and
removing the mixture from the container.

101. The method according to clause 99, wherein collecting one or more components of the blood sample comprises:
positioning the device at a first angular position with respect to an axis orthogonal to the ground;
removing a portion of a first fraction of the blood sample through the conduit;
tilting the device to a second angular position with respect to the axis orthogonal to the ground;
aspirating the remaining portion of the first fraction of the blood sample through the conduit;
mixing the remaining portion of the first fraction with a second fraction within the buoy to produce a mixture of the first fraction and the second fraction; and
removing the mixture from the container.

102. The method according to clause 101, wherein the second angular position is from 5° to 20° with respect to the first angular position of the device.

103. The method according to clause 101, wherein the second angular position is 10° with respect to the first angular position.

104. The method according to any of clauses 100-101, wherein the first fraction comprises platelet poor plasma.

105. The method according to any of clauses 100-101, wherein the second fraction comprises platelets and white blood cells.

106. The method according to any of clauses 100-101, wherein 75% by volume or more of the first fraction is removed from the blood sample.

107. The method according to any of clauses 100-101, wherein 90% by volume or more of the first fraction is removed from the blood sample.

108. A method comprising: introducing a biological sample into a device comprising:
a container comprising a distal end and a proximal end; and
a buoy configured to be displaced along a longitudinal axis within the container, wherein the buoy comprises one or more sealed chambers comprising a fluidic composition;
subjecting the biological sample to a force of centrifugation to produce two or more fractions in the blood sample;
collecting one or more components of the biological sample.

109. The method according to clause 108, wherein collecting one or more components of the blood biological comprises:
removing a portion of a first fraction of the biological sample;
mixing the remaining portion of the first fraction with a second fraction within the buoy to produce a mixture of the first fraction and the second fraction; and
removing the mixture from the container.

110. The method according to clause 109, wherein the first fraction comprises platelet poor plasma.

111. The method according to clause 109, wherein the second fraction comprises platelets and white blood cells.

112. The method according to clause 109, wherein 75% by volume or more of the first fraction is removed from the biological sample.

113. The method according to clause 109, wherein 90% by volume or more of the first fraction is removed from the biological sample.

114. The method according to clause 109, wherein mixing the remaining portion of the first fraction with the second fraction comprises:
   aspirating the remaining portion of the first fraction and the second fraction into a syringe; and
   reinjecting the first fraction and the second fraction within the buoy to produce a mixture of the first fraction and the second fraction.

115. The method according to clause 108, wherein the buoy comprises a frustoconical shape.

116. The method according to clause 115, wherein the buoy comprises:
   a proximal end having a concave outer surface;
   an orifice at the base of the concave outer surface; and
   a centrifuge activated valve comprising an open position and a closed position, wherein the valve is configured in the closed position to fluidically seal the orifice at the base of the concave outer surface.

117. The method according to clause 116, wherein the centrifuge activated valve is an umbrella valve.

118. The method according to clause 116, wherein the centrifuge activated valve is a check valve.

119. The method according to clause 116, wherein the centrifuge activated valve comprises a ball and spring.

120. The method according to clause 116, wherein subjecting the biological sample to a force of centrifugation is sufficient to switch the centrifuge activated valve to an open position.

121. The method according to clause 120, wherein subjecting the biological sample to a force of centrifugation comprises subjecting the biological sample to a first force of centrifugation when the centrifuge activated valve is in an open position and subjecting the biological sample to a second force of centrifugation when the centrifuge activated valve is in a closed position.

122. The method according to clause 116, wherein subjecting the biological sample to a force of centrifugation is sufficient to collect a fraction of the biological sample on the concave outer surface of the buoy.

123. The method according to clause 122, wherein subjecting the biological sample to a force of centrifugation is sufficient to collect a fraction of the biological sample adjacent to the orifice at the base of the concave outer surface.

124. The method according to clause 116, wherein the buoy comprises:
   a first orifice at the base of the concave outer surface;
   a second orifice at a position distal along the longitudinal axis of the buoy to the first orifice; and a channel that extends from the first orifice to the second orifice;
   a centrifuge activated valve comprising an open position and a closed position, wherein the valve is configured in the closed position to fluidically seal the channel.

125. The method according to clause 124, wherein the centrifuge activated valve is positioned at the first orifice.

126. The method according to clause 124, wherein the centrifuge activated valve is positioned at the second orifice.

127. The method according to clause 124, wherein the centrifuge activated valve is positioned within the channel between the first orifice and the second orifice.

128. The method according to clause 124, wherein the centrifuge activated valve is an umbrella valve.

129. The method according to clause 124, wherein the centrifuge activated valve is a check valve.

130. The method according to clause 129, wherein the check valve comprises a ball and spring.

131. The method according to clause 124, wherein subjecting the biological sample to a force of centrifugation is sufficient to switch the centrifuge activated valve to an open position.

132. The method according to clause 131, wherein subjecting the biological sample to a force of centrifugation comprises subjecting the biological sample to a first force of centrifugation when the centrifuge activated valve is in an open position and subjecting the biological sample to a second force of centrifugation when the centrifuge activated valve is in a closed position.

133. The method according to clause 131, wherein subjecting the biological sample to a force of centrifugation is sufficient to collect a fraction of the biological sample in the channel.

134. The method according to clause 133, wherein subjecting the biological sample to a force of centrifugation is sufficient to collect a fraction of the biological sample in the channel adjacent to the first orifice.

135. The method according to clause 133, wherein subjecting the biological sample to a force of centrifugation is sufficient to collect a fraction of the biological sample in the channel adjacent to the second orifice.

136. The method according to clause 133, wherein subjecting the biological sample to a force of centrifugation is sufficient to collect a fraction of the biological sample on the concave outer surface of the buoy.

137. The method according to clause 133, wherein subjecting the biological sample to a force of centrifugation is sufficient to collect a fraction of the biological sample on the concave outer surface of the buoy adjacent to the first orifice.

138. The method according to clause 116, wherein collecting one or more components of the biological sample comprises:
   positioning the device at a first angle with respect to an axis orthogonal to the ground;
   removing a portion of a first fraction of the biological sample;
   rotating the device by a second angle along the longitudinal axis of the device;
   aspirating the remaining portion of the first fraction of the biological sample through the conduit;
   mixing the remaining portion of the first fraction with a second fraction within the buoy to produce a mixture of the first fraction and second fraction; and
   removing the mixture from the container.

139. The method according to clause 116, wherein collecting one or more components of the biological sample comprises:
   positioning the device at a first angular position with respect to an axis orthogonal to the ground;
   removing a portion of a first fraction of the biological sample;
   tilting the device to a second angular position with respect to the axis orthogonal to the ground;
   aspirating the remaining portion of the first fraction of the biological sample;
   mixing the remaining portion of the first fraction with a second fraction within the buoy to produce a mixture of the first fraction and the second fraction; and
   removing the mixture from the container.

140. The method according to clause 139, wherein the second angular position is from 5° to 20° with respect to the first angular position of the device.

141. The method according to clause 139, wherein the second angular position is 10° with respect to the first angular position.

142. The method according to clause 116, wherein the container comprises:
a cap positioned at the proximal end comprising an inlet into the cavity of the container; and a conduit that connects the inlet to the proximal end of the buoy.
143. The method according to clause 142, wherein the conduit is connected to the proximal end of the buoy at a position adjacent to the inner wall of the container.
144. The method according to clause 143, wherein collecting one or more components of the biological sample comprises:
positioning the container at a first angle with respect to an axis orthogonal to the ground;
removing a portion of a first fraction of the biological sample through the conduit;
rotating the container by a second angle along the longitudinal axis of the container;
aspirating the remaining portion of the first fraction of the biological sample through the conduit;
mixing the remaining portion of the first fraction with a second fraction within the buoy to produce a mixture of the first fraction and second fraction; and
removing the mixture from the container.
145. The method according to clause 143, wherein collecting one or more components of the biological sample comprises:
positioning the device at a first angular position with respect to an axis orthogonal to the ground;
removing a portion of a first fraction of the biological sample through the conduit;
tilting the device to a second angular position with respect to the axis orthogonal to the ground;
aspirating the remaining portion of the first fraction of the biological sample through the conduit;
mixing the remaining portion of the first fraction with a second fraction within the buoy to produce a mixture of the first fraction and the second fraction; and
removing the mixture from the container.
146. The method according to clause 145, wherein the second angular position is from 5° to 20° with respect to the first angular position of the device.
147. The method according to clause 145, wherein the second angular position is 10° with respect to the first angular position.
148. The method according to clause 147, wherein the first fraction comprises platelet poor plasma.
149. The method according to clause 147, wherein the second fraction comprises platelets and white blood cells.
150. The method according to clause 147, wherein 75% by volume or more of the first fraction is removed from the biological sample.
151. The method according to clause 147, wherein 90% by volume or more of the first fraction is removed from the biological sample.
152. The method according to any of clauses 116-151, wherein the biological sample is selected from the group consisting of whole blood, bone marrow aspirate, stromal vascular fraction and a combination thereof.
153. The method according to any of clauses 116-151, wherein the biological sample is whole blood.
154. The method according to any of clauses 116-151, wherein the biological sample is bone marrow aspirate.
155. The method according to any of clauses 116-151, wherein the biological sample is stromal vascular fraction.

156. A method comprising:
introducing a multicomponent liquid sample into a device comprising:
a container comprising a distal end and a proximal end; and
a buoy configured to be displaced along a longitudinal axis within the container, wherein the buoy comprises one or more sealed chambers comprising a fluidic composition;
subjecting the multicomponent liquid sample to a force of centrifugation to produce two or more fractions in the multicomponent liquid sample;
collecting one or more components from the separated fractions.
157. The method according to clause 156, wherein the buoy comprises a frustoconical shape.
158. The method according to clause 157, wherein the buoy comprises:
a proximal end having a concave outer surface;
an orifice at the base of the concave outer surface; and
a centrifuge activated valve comprising an open position and a closed position, wherein the valve is configured in the closed position to fluidically seal the orifice at the base of the concave outer surface.
159. The method according to clause 158, wherein the centrifuge activated valve comprises a ball and spring.
160. The method according to clause 158, wherein subjecting the multicomponent liquid sample to a force of centrifugation is sufficient to switch the centrifuge activated valve to an open position.
161. The method according to clause 158, wherein subjecting the multicomponent liquid sample to a force of centrifugation is sufficient to collect a fraction on the concave outer surface of the buoy.
162. The method according to clause 161, wherein subjecting the multicomponent liquid sample to a force of centrifugation is sufficient to collect a fraction adjacent to the orifice at the base of the concave outer surface.
163. The method according to clause 158, wherein the buoy comprises:
a first orifice at the base of the concave outer surface;
a second orifice at a position distal along the longitudinal axis of the buoy to the first orifice; and
a channel that extends from the first orifice to the second orifice;
a centrifuge activated valve comprising an open position and a closed position, wherein the valve is configured in the closed position to fluidically seal the channel.
164. The method according to clause 163, wherein the centrifuge activated valve is positioned at the first orifice.
165. The method according to clause 163, wherein the centrifuge activated valve is positioned at the second orifice.
166. The method according to clause 163, wherein the centrifuge activated valve is positioned within the channel between the first orifice and the second orifice.
167. The method according to clause 163, wherein the centrifuge activated valve is an umbrella valve.
168. The method according to clause 163, wherein the centrifuge activated valve is a check valve.
169. The method according to clause 168, wherein the check valve comprises a ball and spring.
170. The method according to clause 163, wherein subjecting the multicomponent liquid sample to a force of centrifugation is sufficient to switch the centrifuge activated valve to an open position.
171. The method according to clause 170, wherein subjecting the multicomponent liquid sample to a force of centrifugation comprises subjecting the blood sample to a first force of centrifugation when the centrifuge activated valve is in an open position and subjecting the multicomponent liquid sample to a second force of centrifugation when the centrifuge activated valve is in a closed position.

172. The method according to clause 170, wherein subjecting the multicomponent liquid sample to a force of centrifugation is sufficient to collect a fraction in the channel.

173. The method according to clause 172, wherein subjecting the multicomponent liquid sample to a force of centrifugation is sufficient to collect a fraction in the channel adjacent to the first orifice.

174. The method according to clause 172, wherein subjecting the multicomponent liquid sample to a force of centrifugation is sufficient to collect a fraction in the channel adjacent to the second orifice.

175. The method according to clause 174, wherein subjecting the multicomponent liquid sample to a force of centrifugation is sufficient to collect a fraction on the concave outer surface of the buoy.

176. The method according to clause 174, wherein subjecting the multicomponent liquid sample to a force of centrifugation is sufficient to collect a fraction on the concave outer surface of the buoy adjacent to the first orifice.

177. The method according to clause 156, wherein collecting one or more components of the multicomponent sample comprises:
    positioning the container at a first angle with respect to an axis orthogonal to the ground;
    removing a portion of a first fraction;
    positioning the container at a second angle with respect to an axis orthogonal to the ground;
    aspirating the remaining portion of the first fraction;
    mixing the remaining portion of the first fraction with a second fraction within the buoy to produce a mixture of the first fraction and second fraction; and
    removing the mixture from the container.

178. The method according to clause 156, wherein collecting one or more components of the multicomponent sample comprises:
    positioning the device at a first angular position with respect to an axis orthogonal to the ground;
    removing a portion of a first fraction of the sample;
    tilting the device to a second angular position with respect to the axis orthogonal to the ground;
    aspirating the remaining portion of the first fraction of the sample;
    mixing the remaining portion of the first fraction with a second fraction within the buoy to produce a mixture of the first fraction and the second fraction; and
    removing the mixture from the container.

179. The method according to clause 178, wherein the second angular position is from 5° to 20° with respect to the first angular position of the device.

180. The method according to clause 178, wherein the second angular position is 10° with respect to the first angular position.

181. The method according to clause 156, wherein the container comprises:
    a cap positioned at the proximal end comprising an inlet into the cavity of the container; and
    a conduit that connects the inlet to the proximal end of the buoy.

182. The method according to clause 181, wherein the conduit is connected to the proximal end of the buoy at a position adjacent to the inner wall of the container.

183. The method according to clause 181, wherein the cap comprises a single inlet into the cavity of the container.

184. The method according to clause 181, wherein the conduit further comprises a stream modulator.

185. The method according to clause 184, wherein the stream modulator is configured to adjust a rate of fluid output from the conduit.

186. The method according to clause 184, wherein the stream modulator is configured to adjust a shape fluid output from the conduit.

187. The method according to clause 184, wherein the stream modulator is configured to adjust the cross-sectional dimensions of fluid output from the conduit.

188. The method according to clause 156, wherein collecting one or more components of the multicomponent sample comprises:
    positioning the container at a first angle with respect to an axis orthogonal to the ground;
    removing a portion of a first fraction through the conduit;
    positioning the container at a second angle with respect to an axis orthogonal to the ground;
    aspirating the remaining portion of the first fraction through the conduit;
    mixing the remaining portion of the first fraction with a second fraction within the buoy to produce a mixture of the first fraction and second fraction; and
    removing the mixture from the container.

189. The method according to clause 156, wherein collecting one or more components of the multicomponent sample comprises:
    positioning the device at a first angular position with respect to an axis orthogonal to the ground;
    removing a portion of a first fraction through the conduit;
    tilting the device to a second angular position with respect to the axis orthogonal to the ground;
    aspirating the remaining portion of the first fraction through the conduit;
    mixing the remaining portion of the first fraction with a second fraction within the buoy to produce a mixture of the first fraction and the second fraction; and
    removing the mixture from the container.

190. The method according to clause 189, wherein the second angular position is from 5° to 20° with respect to the first angular position of the device.

191. The method according to clause 189, wherein the second angular position is 10° with respect to the first angular position.

192. A system comprising:
    a device for separating components of a multi-component liquid comprising:
    a container comprising a distal end and a proximal end, wherein the container comprises a cap positioned at the proximal end comprising an inlet into the cavity of the container; and
    a buoy configured to be displaced along a longitudinal axis within the container, wherein the buoy comprises one or more sealed chambers; and
    a support for positioning the container at an angle with respect to an axis orthogonal to the ground.

193. The system according to clause 192, wherein the container further comprises a cap positioned at the proximal end comprising an inlet into the cavity of the container.

194. The system according to clause 193, wherein the cap comprises a single inlet into the cavity of the container.

195. The system according to clause 193, wherein the cap forms a fluidic seal with the internal walls of the container.

196. The system according to clause 193, wherein the cap further comprises a vent port.

197. The system according to clause 192, further comprising a conduit that extends from the inlet to the proximal end of the buoy.

198. The system according to clause 197, wherein the conduit is connected to the proximal end of the buoy at a position adjacent to the inner wall of the container.

199. The system according to clause 197, wherein the conduit is releasably attached to one or more of the inlet and the proximal end of the buoy.

200. The system according to clause 197, wherein the conduit is integrated with one or more of the inlet or the proximal end of the buoy.

201. The system according to clause 197, wherein the conduit is releasably attached to the inlet and integrated with the proximal end of the buoy.

202. The system according to clause 197, wherein the conduit is flexible.

203. The system according to clause 202, wherein the conduit is coiled.

204. The system according to clause 197, wherein the conduit further comprises a stream modulator.

205. The system according to clause 204, wherein the stream modulator is configured to adjust a rate of fluid output from the conduit.

206. The system according to clause 204, wherein the stream modulator is configured to adjust a shape fluid output from the conduit.

207. The system according to clause 204, wherein the stream modulator is configured to adjust the cross-sectional dimensions of fluid output from the conduit.

208. The system according to clause 192, wherein the support is configured to position the container at an angle that is 10 degrees or more with respect to an axis orthogonal to the ground.

209. The system according to clause 192, wherein the support is adjustable to position the container at an angle that is from 10 degrees to 90 degrees with respect to an axis orthogonal to the ground.

210. The system according to clause 209, wherein the support further comprises an actuator to adjust the position of the container when positioned in the support.

211. The system according to clause 210, wherein the actuator is mechanical.

212. The system according to clause 210, wherein the actuator is motor-powered.

213. The system according to clause 192, wherein the support is configured for positioning the container at a second angle.

214. The system according to clause 213, wherein the support is configured for rotating the container an angle of 45 degrees or more along a longitudinal axis of the container.

215. The system according to clause 213, wherein the support is configured to rotate the container an angle of 180 degrees or more along a longitudinal axis of the container.

215. The system according to clause 192, wherein the buoy comprises a frustoconical shaped component.

216. The system according to clause 215, wherein the buoy comprises a cylindrical proximal portion and frustoconical distal portion.

217. The system according to clause 215, wherein the proximal end of the buoy comprises a concave outer surface.

218. The system according to clause 192, wherein the sealed chambers contain a vacuum, a fluidic composition or a combination thereof 219. The system according to clause 192, wherein one or more sealed chambers contain a vacuum.

220. The system according to clause 192, wherein one or more sealed chambers contain a fluidic composition.

221. The system according to clause 192, wherein the fluidic composition comprises a gaseous composition.

222. The system according to clause 192, wherein the gaseous composition comprises a gas selected from the group consisting of air, carbon dioxide, oxygen, nitrogen, hydrogen, helium, argon, xenon or a combination thereof 223. The system according to clause 192, wherein the fluidic composition comprises a liquid composition.

224. The system according to clause 192, wherein the fluidic composition comprises an alcohol.

225. The system according to clause 192, wherein one or more sealed chambers contain a vacuum and one or more sealed chambers contain a fluidic composition.

226. The system according to clause 192, wherein the buoy comprises:
 an orifice at the base of the concave outer surface; and
 a centrifuge activated valve comprising an open position and a closed position, wherein the valve is configured in the closed position to fluidically seal the orifice at the base of the concave outer surface.

227. The system according to clause 226, wherein the centrifuge activated valve is an umbrella valve.

228. The system according to clause 226, wherein the centrifuge activated valve is a check valve.

229. The system according to clause 228, wherein the check valve is selected from the group consisting of a ball check valve, a diaphragm check valve, a lift check valve and a tilted disc check valve.

230. The system according to clause 226, wherein the centrifuge activated valve comprises a ball and spring.

231. The system according to clause 230, wherein the ball comprises stainless steel.

232. The system according to clause 192, wherein the buoy comprises:
 a first orifice at the base of the concave outer surface;
 a second orifice at a position distal along the longitudinal axis of the buoy to the first orifice; and
 a channel that extends from the first orifice to the second orifice;
 a centrifuge activated valve comprising an open position and a closed position, wherein the valve is configured in the closed position to fluidically seal the channel.

233. The system according to clause 232, wherein the centrifuge activated valve is positioned at the first orifice.

234. The system according to clause 232, wherein the centrifuge activated valve is positioned at the second orifice.

235. The system according to clause 232, wherein the centrifuge activated valve is positioned within the channel between the first orifice and the second orifice.

236. The system according to clause 235, wherein the centrifuge activated valve is an umbrella valve.

237. The system according to clause 232, wherein the centrifuge activated valve is a check valve.

238. The system according to clause 237, wherein the check valve is selected from the group consisting of a ball check valve, a diaphragm check valve, a lift check valve and a tilted disc check valve.

239. The system according to clause 237, wherein the centrifuge activated valve comprises a ball and spring.

240. The system according to clause 239, wherein the ball comprises stainless steel.

241. The system according to clause 192, wherein the gaseous composition comprises a compound selected from the group consisting of air, carbon dioxide, oxygen, nitrogen, hydrogen, helium, argon, xenon or a combination thereof.

242. The system according to clause 241, wherein the gaseous composition comprises air.

243. The system according to clause 192, wherein the one or more sealed chambers comprises 25% or more of the total volume of the buoy.

244. The system according to clause 243, wherein the one or more sealed chambers comprises 50% or more of the total volume of the buoy.

245. The system according to clause 192, wherein the buoy comprises a polymer selected from the group consisting of polycarbonate, polycarbonate alloys, polyethylene, polypropylene, polytetrafluoroethylene (PTFE), polyvinylidene fluoride (PVDF), ethyl vinyl acetate (EVA), polyurethane, polyethersulfone, copolymers and combinations thereof.

246. The system according to clause 245, wherein the buoy comprises polycarbonate.

247. The system according to any of the preceding clause, wherein the multi-component liquid is a biological sample or a derivative thereof.

248. The method according to clause 247, wherein the biological sample is selected from the group consisting of whole blood, bone marrow aspirate, stromal vascular fraction and a combination thereof.

249. The method according to any of the preceding clauses, wherein the biological sample is whole blood.

250. The method according to any of the preceding clauses, wherein the biological sample is bone marrow aspirate.

251. The method according to any of the preceding clauses, wherein the biological sample is stromal vascular fraction.

252. A system comprising:
  a centrifuge;
  a device for separating components of blood, the device comprising:
    a container comprising a distal end and a proximal end; and
    a buoy configured to be displaced along a longitudinal axis within the container, wherein the buoy comprises one or more sealed chambers.

253. The system according to clause 252, wherein the centrifuge is a fixed angle centrifuge.

254. The system according to clause 252, wherein the centrifuge is a swinging bucket centrifuge.

255. The system according to clause 252, wherein the proximal end of the buoy comprises a concave outer surface.

256. The system according to clause 255, wherein the buoy comprises:
  an orifice at the base of the concave outer surface; and
  a centrifuge activated valve comprising an open position and a closed position, wherein the valve is configured in the closed position to fluidically seal the orifice at the base of the concave outer surface.

257. The system according to clause 256, wherein the centrifuge activated valve is an umbrella valve.

258. The system according to clause 256, wherein the centrifuge activated valve is a check valve.

259. The system according to clause 257, wherein the check valve is selected from the group consisting of a ball check valve, a diaphragm check valve, a lift check valve and a tilted disc check valve.

260. The system according to clause 259, wherein the centrifuge activated valve comprises a ball and spring.

261. The system according to clause 260, wherein the ball comprises stainless steel.

262. The system according to clause 252, wherein the buoy comprises:
  a first orifice at the base of the concave outer surface;
  a second orifice at a position distal along the longitudinal axis of the buoy to the first orifice; and
  a channel that extends from the first orifice to the second orifice;
  a centrifuge activated valve comprising an open position and a closed position, wherein the valve is configured in the closed position to fluidically seal the channel.

263. The system according to clause 262, wherein the centrifuge activated valve is positioned at the first orifice.

264. The system according to clause 262, wherein the centrifuge activated valve is positioned at the second orifice.

265. The system according to clause 262, wherein the centrifuge activated valve is positioned within the channel between the first orifice and the second orifice.

266. The system according to clause 262, wherein the centrifuge activated valve is an umbrella valve.

267. The system according to clause 262, wherein the centrifuge activated valve is a check valve.

268. The system according to clause 267, wherein the check valve is selected from the group consisting of a ball check valve, a diaphragm check valve, a lift check valve and a tilted disc check valve.

269. The system according to clause 267, wherein the centrifuge activated valve comprises a ball and spring.

270. The system according to clause 269, wherein the ball comprises stainless steel.

271. The system according to clause 252, wherein the container further comprises a cap positioned at the proximal end comprising an inlet into the cavity of the container.

272. The system according to clause 271, wherein the cap comprises a single inlet into the cavity of the container.

273. The system according to clause 271, wherein the cap forms a fluidic seal with the internal walls of the container.

274. The system according to clause 271, wherein the cap further comprises a vent port.

275. The system according to clause 271, further comprising a conduit that extends from the inlet to the proximal end of the buoy.

276. The system according to clause 275, wherein the conduit is connected to the proximal end of the buoy at a position adjacent to the inner wall of the container.

277. The system according to clause 276, wherein the conduit is releasably attached to one or more of the inlet and the proximal end of the buoy.

278. The system according to clause 276, wherein the conduit is integrated with one or more of the inlet or the proximal end of the buoy.

279. The system according to clause 276, wherein the conduit is releasably attached to the inlet and integrated with the proximal end of the buoy.

280. The system according to claim 276, wherein the conduit is flexible.

281. The system according to claim 276, wherein the conduit is coiled.

282. The system according to clause 275, wherein the conduit further comprises a stream modulator.

283. The system according to clause 282, wherein the stream modulator is configured to adjust a rate of fluid output from the conduit.

284. The system according to clause 282, wherein the stream modulator is configured to adjust a shape fluid output from the conduit.

285. The system according to clause 282, wherein the stream modulator is configured to adjust the cross-sectional dimensions of fluid output from the conduit.
286. The system according to clause 252, wherein the sealed chambers contain a vacuum, a fluidic composition or a combination thereof.
287. The system according to clause 286, wherein one or more sealed chambers contain a vacuum.
288. The system according to clause 286, wherein one or more sealed chambers contain a fluidic composition.
289. The system according to clause 288, wherein the fluidic composition comprises a gaseous composition.
290. The system according to clause 289, wherein the gaseous composition comprises a compound selected from the group consisting of air, carbon dioxide, oxygen, nitrogen, hydrogen, helium, argon, xenon or a combination thereof.
291. The system according to clause 290, wherein the gaseous composition comprises air.
292. The system according to clause 288, wherein the fluidic composition comprises a liquid composition.
293. The system according to clause 292, wherein the fluidic composition comprises an alcohol.
294. The system according to clause 252, wherein one or more sealed chambers contain a vacuum and one or more sealed chambers contain a fluidic composition.
295. The system according to clause 252, wherein the one or more sealed chambers comprises 25% or more of the total volume of the buoy.
296. The system according to clause 252, wherein the one or more sealed chambers comprises 50% or more of the total volume of the buoy.
297. The system according to clause 252, wherein the buoy comprises a polymer selected from the group consisting of polycarbonate, polycarbonate alloys, polyethylene, polypropylene, polytetrafluoroethylene (PTFE), polyvinylidene fluoride (PVDF), ethyl vinyl acetate (EVA), polyurethane, polyethersulfone, copolymers and combinations thereof
160. The system according to clause 159, wherein the buoy comprises polycarbonate.
298. A kit comprising:
   a device for separating components of a multi-component liquid, the device comprising: a container comprising a distal end and a proximal end; and a buoy configured to be displaced along a longitudinal axis within the container, wherein the buoy comprises one or more sealed chambers comprising a fluidic composition; and
   a container housing the device.
299. The kit according to clause 298, wherein the container comprises a pouch.
300. The kit according to clause 298, further comprising a syringe.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:
1. A method comprising:
   introducing a biological sample into a device for separating components of a multi-component liquid, the device comprising:
   a container comprising a distal end and a proximal end; and
   a buoy having a distal end and a proximal end and is configured to be displaced along a longitudinal axis within the container, wherein the buoy comprises:
      one or more chambers containing a vacuum or a fluid and sealed from fluidic communication with an outside environment of the buoy;
      a concave first outer surface at the proximal end of the buoy, the first surface comprising a first orifice at the base of the concave outer surface, wherein the buoy does not comprise a valve at the first orifice;
      a second outer surface at the distal end of the buoy comprising a second orifice at a position distal along the longitudinal axis of the buoy to the first orifice, the first orifice in fluid communication with the second orifice through a channel extending from the first orifice to the second orifice; and
      a centrifuge activated ball and spring valve at the second orifice comprising an open position and a closed position;
      wherein the valve is configured to be in the closed position to fluidically seal the second orifice without centrifugation, wherein the valve is configured to continuously be in the open position during centrifugation in response to an applied force of centrifugation, and wherein the ball of the valve is configured to compress in response to the applied force of centrifugation in the open position;
   subjecting the biological sample to a force of centrifugation to produce two or more fractions in the biological sample; and
   collecting one or more fractions or portions of fractions of the biological sample.
2. The method according to claim 1, wherein collecting one or more components of the biological sample comprises:
   removing a portion of a first fraction of the biological sample;
   mixing the remaining portion of the first fraction with a second fraction within the buoy to produce a mixture of the first fraction and the second fraction; and
   removing the mixture from the container.
3. The method according to claim 1, wherein collecting one or more components of the biological sample comprises:
   positioning the device at a first angle with respect to an axis orthogonal to the ground;
   removing a portion of a first fraction of the biological sample;

rotating the device by a second angle along the longitudinal axis of the container;
aspirating the remaining portion of the first fraction of the biological sample;
mixing the remaining portion of the first fraction with a second fraction within the buoy to produce a mixture of the first fraction and second fraction; and
removing the mixture from the container.

4. The method according to claim 3, wherein the first angle is 10 degrees or more with respect to an axis orthogonal to the ground.

5. The method according to claim 3, wherein the first angle is 10 degrees to 90 degrees with respect to an axis orthogonal to the ground.

6. The method according to claim 3, wherein the second angle is 45 degrees or more along the longitudinal axis of the container.

7. The method according to claim 3, wherein the second angle is 180 degrees or more along the longitudinal axis of the container.

8. The method according to claim 3, wherein the device is positioned at the first angle and the second angle using a support configured for positioning the device at the first angle and second angle.

9. The method according to claim 1, wherein collecting one or more components of the biological sample comprises:
positioning the device at a first angular position with respect to an axis orthogonal to the ground;
removing a portion of a first fraction of the biological sample;
tilting the device to a second angular position with respect to the axis orthogonal to the ground;
aspirating the remaining portion of the first fraction of the biological sample;
mixing the remaining portion of the first fraction with a second fraction within the buoy to produce a mixture of the first fraction and the second fraction; and
removing the mixture from the container.

10. The method according to claim 1, wherein the biological fluid is selected from the group consisting of whole blood or a derivative thereof, bone marrow aspirate or a derivative thereof, stromal vascular fractions or a derivative thereof or any combination thereof.

11. The method according to claim 1, wherein the biological fluid is whole blood or a derivative thereof.

12. The method according to claim 11, wherein a first fraction comprises platelet poor plasma and a second fraction comprises platelets and white blood cells.

13. The method according to claim 11, wherein 75% to 95% by volume of a first fraction is removed from the whole blood sample.

14. The method according to claim 11, wherein subjecting the whole blood sample to a force of centrifugation is sufficient to switch the centrifuge activated valve to an open position.

15. The method according to claim 14, wherein subjecting the blood sample to a force of centrifugation comprises subjecting the blood sample to a first force of centrifugation when the centrifuge activated valve is in an open position and subjecting the blood sample to a second force of centrifugation when the centrifuge activated valve is in a closed position.

16. The method according to claim 14, wherein subjecting the blood sample to a force of centrifugation is sufficient to collect a fraction of the blood sample in the channel.

17. The method according to claim 16, wherein subjecting the blood sample to a force of centrifugation is sufficient to collect a fraction of the blood sample in the channel adjacent to the first orifice.

18. The method according to claim 16, wherein subjecting the blood sample to a force of centrifugation is sufficient to collect a fraction of the blood sample in the channel adjacent to the second orifice.

19. The method according to claim 16, wherein subjecting the blood sample to a force of centrifugation is sufficient to collect a fraction of the blood sample on the concave outer surface of the buoy.

20. A system comprising:
(a) a device for separating components of a multi-component liquid, the device comprising:
a container comprising a distal end and a proximal end; and
a buoy having a distal end and a proximal end and is configured to be displaced along a longitudinal axis within the container, wherein the buoy comprises:
one or more chambers containing a vacuum or a fluid and sealed from fluidic communication with an outside environment of the buoy;
a concave first outer surface at the proximal end of the buoy, the first surface comprising a first orifice at the base of the concave outer surface, wherein the buoy does not comprise a valve at the first orifice;
a second outer surface at the distal end of the buoy comprising a second orifice at a position distal along the longitudinal axis of the buoy to the first orifice, the first orifice in fluid communication with the second orifice through a channel extending from the first orifice to the second orifice; and
a centrifuge activated ball and spring valve at the second orifice comprising an open position and a closed position;
wherein the valve is configured to be in the closed position to fluidically seal the second orifice without centrifugation, wherein the valve is configured to continuously be in the open position during centrifugation in response to a force of centrifugation, and wherein the ball of the valve is configured to compress in response to the applied force of centrifugation in the open position;
(b) a support for positioning the container at an angle with respect to an axis orthogonal to the ground; or
(c) a centrifuge.

21. The system according to claim 20, wherein the system comprises the device for separating components of the multi-component liquid and the support.

22. The system according to claim 21, wherein the support is adjustable to position the container at an angle that is from 10 degrees to 90 degrees with respect to an axis orthogonal to the ground.

23. The system according to claim 22, wherein the support further comprises an actuator to adjust the position of the container when positioned in the support.

24. The system according to claim 22, wherein the system comprises the device for separating components of the multi-component liquid and the centrifuge.

* * * * *